US008795318B2

(12) United States Patent
Hallisey et al.

(10) Patent No.: US 8,795,318 B2
(45) Date of Patent: Aug. 5, 2014

(54) PERCUTANEOUS RETRIEVABLE VASCULAR FILTER

(75) Inventors: Michael J. Hallisey, Wethersfield, CT (US); Jeremy W. Snow, South Jordan, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 69 days.

(21) Appl. No.: 12/722,484

(22) Filed: Mar. 11, 2010

(65) Prior Publication Data

US 2011/0137335 A1 Jun. 9, 2011

Related U.S. Application Data

(63) Continuation-in-part of application No. 12/203,515, filed on Sep. 3, 2008, now Pat. No. 8,062,328, and a continuation-in-part of application No. PCT/US2010/023100, filed on Feb. 3, 2010.

(60) Provisional application No. 60/967,704, filed on Sep. 7, 2007, provisional application No. 61/180,041, filed on May 20, 2009, provisional application No. 61/263,712, filed on Nov. 23, 2009, provisional application No. 61/149,482, filed on Feb. 3, 2009, provisional application No. 61/180,041, filed on May 20, 2009.

(51) Int. Cl.
*A61M 29/00* (2006.01)

(52) U.S. Cl.
USPC ........................................ 606/200

(58) Field of Classification Search
USPC .................. 606/108, 159, 200; 604/104–107; 623/1.11
See application file for complete search history.

(56) References Cited

U.S. PATENT DOCUMENTS

| 4,132,650 A | 1/1979 | Kirsch et al. |
| 4,494,531 A | 1/1985 | Gianturco |
| 4,619,246 A | 10/1986 | Molgaard-Nielsen |
| 4,832,055 A | 5/1989 | Palestrant |
| 4,900,312 A | 2/1990 | Nadeau |

(Continued)

FOREIGN PATENT DOCUMENTS

| EP | 1987800 | 4/2008 |
| JP | 61/41444 | 5/1994 |

(Continued)

OTHER PUBLICATIONS

U.S. Appl. No. 13/204,462, filed Aug. 5, 2011, Snow.

(Continued)

*Primary Examiner* — David Eastwood
(74) *Attorney, Agent, or Firm* — Stoel Rives LLP

(57) ABSTRACT

Retrievable vena cava filters for the temporary or permanent prevention of Pulmonary embolism (PE) are disclosed. A filter in accordance with the present invention has a tube-within-tube structure with overlapping semi-spheres. The semi-spheres comprise a plurality of expandable legs. The first tube may have a plurality of slots allowing for deployment of a first or second sets of expandable legs on the second tube. The free end of each leg in the first set of expandable legs may be oriented in a direction the same as or opposite to the free end of each leg in the second set. The filter may also be formed from a single tube. In certain embodiments, the filter of the present invention can be retrieved from either end.

16 Claims, 57 Drawing Sheets

(56) References Cited

U.S. PATENT DOCUMENTS

| | | | |
|---|---|---|---|
| 5,133,733 A | 7/1992 | Rasmussen et al. | |
| 5,234,458 A * | 8/1993 | Metais | 606/200 |
| 5,242,462 A | 9/1993 | El-Nounou et al. | |
| 5,312,479 A | 5/1994 | Weinstein et al. | |
| 5,324,304 A | 6/1994 | Rasmussen | |
| 5,370,657 A | 12/1994 | Irie | |
| 5,375,612 A | 12/1994 | Cottenceau et al. | |
| 5,437,655 A | 8/1995 | Bartholomew | |
| 5,484,474 A | 1/1996 | Weinstein et al. | |
| 5,601,568 A | 2/1997 | Chevillon et al. | |
| 5,626,605 A | 5/1997 | Irie | |
| 5,634,942 A | 6/1997 | Chevillon et al. | |
| 5,669,933 A | 9/1997 | Simon | |
| 5,709,704 A | 1/1998 | Nott et al. | |
| 5,795,322 A | 8/1998 | Boudewijn | |
| 5,810,874 A | 9/1998 | Lefebvre | |
| 5,836,968 A | 11/1998 | Simon et al. | |
| 5,836,969 A | 11/1998 | Kim | |
| 5,853,420 A | 12/1998 | Chevillon et al. | |
| 5,879,381 A | 3/1999 | Moriuchi | |
| 5,954,741 A | 9/1999 | Fox | |
| 5,976,172 A | 11/1999 | Homsma et al. | |
| 5,984,947 A | 11/1999 | Smith | |
| 6,007,558 A | 12/1999 | Ravenscroft et al. | |
| 6,013,093 A | 1/2000 | Nott et al. | |
| 6,059,825 A | 5/2000 | Hobbs | |
| 6,099,549 A | 8/2000 | Bosma et al. | |
| 6,117,165 A | 9/2000 | Becker | |
| 6,156,055 A | 12/2000 | Ravenscroft | |
| 6,193,739 B1 | 2/2001 | Chevillon et al. | |
| 6,214,025 B1 | 4/2001 | Thistle et al. | |
| 6,241,746 B1 | 6/2001 | Bosma et al. | |
| 6,258,026 B1 | 7/2001 | Ravenscroft et al. | |
| 6,267,777 B1 | 7/2001 | Bosma et al. | |
| 6,273,900 B1 | 8/2001 | Nott et al. | |
| 6,273,901 B1 | 8/2001 | Whitcher et al. | |
| 6,306,141 B1 | 10/2001 | Jervis | |
| 6,328,719 B1 | 12/2001 | Holtermann et al. | |
| 6,347,711 B1 | 2/2002 | Goebel et al. | |
| 6,391,045 B1 | 5/2002 | Kim | |
| 6,428,559 B1 | 8/2002 | Johnson | |
| 6,436,121 B1 | 8/2002 | Blom | |
| 6,443,972 B1 * | 9/2002 | Bosma et al. | 606/200 |
| 6,461,370 B1 | 10/2002 | Gray et al. | |
| 6,468,290 B1 | 10/2002 | Weldon et al. | |
| 6,485,501 B1 | 11/2002 | Green | |
| 6,506,205 B2 | 1/2003 | Goldberg et al. | |
| 6,511,496 B1 | 1/2003 | Huter et al. | |
| 6,527,962 B1 | 3/2003 | Nadal | |
| 6,540,722 B1 * | 4/2003 | Boyle et al. | 604/106 |
| 6,540,768 B1 | 4/2003 | Diaz et al. | |
| 6,589,266 B2 | 7/2003 | Whitcher et al. | |
| 6,596,011 B2 | 7/2003 | Johnson et al. | |
| 6,620,183 B2 | 9/2003 | DiMatteo | |
| 6,623,506 B2 | 9/2003 | McGuckin, Jr. et al. | |
| 6,656,203 B2 | 12/2003 | Roth et al. | |
| 6,660,021 B1 | 12/2003 | Palmer et al. | |
| 6,726,701 B2 | 4/2004 | Gilson | |
| 6,783,538 B2 | 8/2004 | McGuckin, Jr. et al. | |
| 6,793,665 B2 | 9/2004 | McGuckin, Jr. et al. | |
| 6,932,831 B2 | 8/2005 | Forber | |
| 6,939,361 B1 | 9/2005 | Kleshinski | |
| 6,958,074 B2 | 10/2005 | Russell | |
| 6,989,021 B2 | 1/2006 | Bosma | |
| 6,991,641 B2 | 1/2006 | Diaz et al. | |
| 7,147,649 B2 | 12/2006 | Thomas | |
| 7,179,275 B2 | 2/2007 | McGuckin | |
| 7,261,731 B2 | 8/2007 | Patel | |
| 7,279,000 B2 | 10/2007 | Cartier et al. | |
| 7,314,477 B1 | 1/2008 | Ravenscroft et al. | |
| 7,323,002 B2 | 1/2008 | Johnson et al. | |
| 7,329,227 B2 | 2/2008 | Schramm | |
| 7,329,269 B2 | 2/2008 | Shapiro et al. | |
| 7,338,512 B2 | 3/2008 | McGuckin, Jr. et al. | |
| 7,344,549 B2 | 3/2008 | Boyle et al. | |
| 7,399,308 B2 | 7/2008 | Borillo et al. | |
| 7,534,251 B2 | 5/2009 | WasDyke | |
| 7,544,202 B2 | 6/2009 | Cartier et al. | |
| 7,582,100 B2 | 9/2009 | Johnson | |
| 7,625,390 B2 | 12/2009 | Hendriksen et al. | |
| 7,699,865 B2 | 4/2010 | Johnson et al. | |
| 7,699,867 B2 | 4/2010 | Hendriksen et al. | |
| 7,704,266 B2 | 4/2010 | Thinnes, Jr. et al. | |
| 7,704,267 B2 | 4/2010 | Tessmer | |
| 7,736,383 B2 | 6/2010 | Bressler et al. | |
| 7,749,246 B2 | 7/2010 | McGuckin et al. | |
| 7,763,045 B2 | 7/2010 | Osborne | |
| 7,771,452 B2 | 8/2010 | Pal et al. | |
| 7,780,694 B2 | 8/2010 | Palmer et al. | |
| 7,794,473 B2 | 9/2010 | Tessmer et al. | |
| 7,803,171 B1 | 9/2010 | Uflacker | |
| 7,862,577 B2 | 1/2011 | Gray et al. | |
| 7,887,561 B2 | 2/2011 | McGuckin, Jr. et al. | |
| 7,909,847 B2 | 3/2011 | McGuckin, Jr. et al. | |
| 7,931,664 B2 | 4/2011 | Gray et al. | |
| 7,959,647 B2 | 6/2011 | Palmer | |
| 7,967,838 B2 | 6/2011 | Chanduszko et al. | |
| 7,972,353 B2 | 7/2011 | Hendriksen et al. | |
| 7,976,562 B2 | 7/2011 | Bressler et al. | |
| 7,996,993 B2 | 8/2011 | Gray et al. | |
| 8,025,675 B2 | 9/2011 | Shirley et al. | |
| 8,029,529 B1 | 10/2011 | Chanduszko | |
| 8,043,322 B2 | 10/2011 | Hendriksen et al. | |
| 8,057,506 B2 | 11/2011 | Gilson et al. | |
| 8,057,507 B2 | 11/2011 | Horan et al. | |
| 8,062,326 B2 | 11/2011 | McGuckin, Jr. et al. | |
| 8,062,327 B2 | 11/2011 | Chanduszko et al. | |
| 8,062,328 B2 | 11/2011 | Hallisey | |
| 8,092,484 B2 | 1/2012 | Kashkarov et al. | |
| 8,092,485 B2 | 1/2012 | Lapid | |
| 8,100,936 B2 | 1/2012 | McGuckin, Jr. et al. | |
| 8,105,349 B2 | 1/2012 | Hendriksen et al. | |
| 8,118,828 B2 | 2/2012 | Cartier et al. | |
| 8,133,251 B2 | 3/2012 | Ravenscroft et al. | |
| 8,133,252 B2 | 3/2012 | Davis et al. | |
| 8,162,972 B2 | 4/2012 | McGuckin, Jr. et al. | |
| 8,167,901 B2 | 5/2012 | Hendriksen et al. | |
| 8,211,140 B2 | 7/2012 | McGunkin, Jr. et al. | |
| 8,246,648 B2 | 8/2012 | Tekulve | |
| 8,246,650 B2 | 8/2012 | Osborne | |
| 8,246,651 B2 | 8/2012 | Hendriksen et al. | |
| 8,252,017 B2 | 8/2012 | Paul, Jr. et al. | |
| 8,252,019 B2 | 8/2012 | Fleming, III | |
| 8,267,954 B2 | 9/2012 | Decant, Jr. et al. | |
| 8,282,668 B2 | 10/2012 | McGuckin, Jr. et al. | |
| 8,317,818 B2 | 11/2012 | Kashkarov et al. | |
| 8,333,785 B2 | 12/2012 | Chanduszko et al. | |
| 8,353,926 B2 | 1/2013 | Silver | |
| 8,366,736 B2 | 2/2013 | Thinnes, Jr. et al. | |
| 8,383,926 B2 | 2/2013 | Plissonnier et al. | |
| 2001/0000799 A1 | 5/2001 | Wessman et al. | |
| 2001/0039432 A1 | 11/2001 | Whitcher et al. | |
| 2002/0058911 A1 * | 5/2002 | Gilson et al. | 604/96.01 |
| 2002/0062134 A1 | 5/2002 | Barbut et al. | |
| 2002/0111647 A1 * | 8/2002 | Khairkhahan et al. | 606/200 |
| 2003/0109897 A1 | 6/2003 | Walak et al. | |
| 2004/0087999 A1 * | 5/2004 | Bosma et al. | 606/200 |
| 2004/0116959 A1 | 6/2004 | McGuckin | |
| 2004/0220610 A1 * | 11/2004 | Kreidler et al. | 606/200 |
| 2005/0004596 A1 * | 1/2005 | McGuckin et al. | 606/200 |
| 2005/0015111 A1 * | 1/2005 | McGuckin et al. | 606/200 |
| 2005/0080447 A1 | 4/2005 | McGuckin, Jr. et al. | |
| 2005/0222604 A1 | 10/2005 | Schaeffer | |
| 2005/0267515 A1 | 12/2005 | Oliva et al. | |
| 2005/0288704 A1 | 12/2005 | Cartier et al. | |
| 2005/0288705 A1 | 12/2005 | Gilson | |
| 2006/0009799 A1 | 1/2006 | Kleshinski et al. | |
| 2006/0041271 A1 | 2/2006 | Bosma et al. | |
| 2006/0079928 A1 | 4/2006 | Cartier | |
| 2006/0079930 A1 | 4/2006 | McGuckin et al. | |
| 2006/0100659 A1 | 5/2006 | Dinh et al. | |
| 2006/0106417 A1 | 5/2006 | Tessmer | |
| 2006/0206138 A1 | 9/2006 | Eidenschink | |
| 2007/0005095 A1 | 1/2007 | Osborne | |

(56) References Cited

U.S. PATENT DOCUMENTS

| | | | |
|---|---|---|---|
| 2007/0141107 | A1 | 6/2007 | Kutryk |
| 2007/0162048 | A1 | 7/2007 | Quinn et al. |
| 2007/0167974 | A1 | 7/2007 | Cully et al. |
| 2007/0173885 | A1 | 7/2007 | Cartier |
| 2007/0191932 | A1 | 8/2007 | Kutryk |
| 2007/0198050 | A1 | 8/2007 | Ravenscroft |
| 2008/0027481 | A1 | 1/2008 | Gilson |
| 2008/0033479 | A1 | 2/2008 | Silver |
| 2008/0097518 | A1 | 4/2008 | Thinnes |
| 2008/0234722 | A1 | 9/2008 | Bonnette et al. |
| 2008/0275487 | A1* | 11/2008 | Fleming ..................... 606/200 |
| 2008/0275492 | A1* | 11/2008 | Farmiga ..................... 606/200 |
| 2009/0043332 | A1 | 2/2009 | Sullivan et al. |
| 2009/0198270 | A1 | 8/2009 | McGuckin, Jr. et al. |
| 2009/0254117 | A1 | 10/2009 | Pakter |
| 2009/0299403 | A1 | 12/2009 | Chanduszko et al. |
| 2009/0299404 | A1 | 12/2009 | Chanduszko et al. |
| 2009/0306703 | A1 | 12/2009 | Kashkarov et al. |
| 2010/0049238 | A1 | 2/2010 | Simpson |
| 2010/0174310 | A1 | 7/2010 | Tessmer |
| 2010/0185229 | A1 | 7/2010 | Horan et al. |
| 2010/0185230 | A1 | 7/2010 | Horan et al. |
| 2010/0198252 | A1 | 8/2010 | Beyer et al. |
| 2010/0318115 | A1 | 12/2010 | Chanduszko et al. |
| 2011/0040321 | A1 | 2/2011 | Cartier |
| 2011/0106133 | A1 | 5/2011 | O'Connell et al. |
| 2011/0166593 | A1 | 7/2011 | Paul, Jr. |
| 2011/0202086 | A1 | 8/2011 | Bates |
| 2011/0208233 | A1 | 8/2011 | McGuckin, Jr. et al. |
| 2012/0089173 | A1 | 4/2012 | Tekulve |
| 2012/0109181 | A1 | 5/2012 | Hallisey |
| 2012/0130418 | A1 | 5/2012 | Jenson et al. |
| 2012/0184985 | A1 | 7/2012 | Ravenscroft et al. |
| 2012/0245622 | A1 | 9/2012 | McGuckin, Jr. et al. |
| 2013/0018387 | A1 | 1/2013 | Diamant |

FOREIGN PATENT DOCUMENTS

| | | |
|---|---|---|
| JP | 2008/154276 | 7/2008 |
| WO | WO02/071977 | 9/2002 |
| WO | WO2007/084431 | 7/2007 |
| WO | WO2009/032834 | 3/2009 |
| WO | WO2010091118 | 8/2010 |

OTHER PUBLICATIONS

U.S. Appl. No. 13/204,492, filed Aug. 5, 2011, Snow.
U.S. Appl. No. 13/203,515, filed Sep. 3, 2008, Hallisey.
Boothroyd et al., 'Product Design for Manufacture and Assembly.' 1994, p. 64.
International Preliminary Report for Application No. PCT/US08/75102 dated Mar. 9, 2010.
International Publication and Written Opinion for Application No. PCT/US08/75102 dated Mar. 12, 2009.
Cipolla et al., 'Complications of Vena Cava Filters: A Comprehensive Clinical Review.' OPUS 12 Scientist 2008; vol. 2, No. 2: 11-24.
Katsamouris et al. 'Inferior Vena Cava Filters: In Vitro Comparison of Clot Trapping and Flow Dynamics.' Radiology 1988; 166:361-366.
Prince et al., 'The diameter of the inferior Vena Cava and It's Implications for the Use of Vena Caval Filters.' Radiology 1983; 149:687-689.
Simon et al., 'Comparative Evaluation of Clinically Available Inferior Vena Cava Filters with an In Vitro Physiologic Simulation of the Vena Cava.' Radiology 1993; 189:769-774.
Lorch et al., 'In Vitro Studies of Temporary Vena Cava Filters.' CardioVascular and Interventional Radiology 1998; 21:146-150.
Neuerburg et al., 'New Retrievable Percutaneous Vena Cava Filter: Experimental In Vitro and In Vivo Evaluation.' CardioVascular and Interventional Radiology 1993: 16:224-229.
Reekers et al., 'Evaluation of the Retrievability of the OptEase IVC Filter in an Animal Model.' J Vasc Interv Radiol 2004; 15:261-267.
Kinney, 'Update on Inferior Vena Cava Filters.' J Vasc Intery Radiol 2003; 14:425-440.
Bruckheimer et al., 'In Vitro Evaluation of a Retrievable Low-Profile Nitinol Vena Cava Filter.' J Vasc Interv Radiol 2003; 14:469-474.
Brountzos et al., 'A New Optional Vena Cava Filter: Retrieval at 12 Weeks in an Animal Model.' J Vasc Interv Radiol 2003; 14:763-772.
Ray et al., 'Outcomes with Retrievable Inferior Vena Cava Filters: A Multicenter Study.' J Vasc Interv Radiol 2006; 17:1595-1604.
Kaufman et al., 'Guidelines for the Use of Retrievable and Convertible Vena Cava Filters: Report from the Society of Interventional Radiology Mulitdisciplinary consensus conference.' J Vasc Interv Radiol 2006; 17:449-459.
Kolbeck et al., 'Optional Inferior Vena Cava Filter Retrieval with Retained Thrombus: An In Vitro Model.' J Vasc Interv Radiol 2006; 17:685-691.
Lorch et al., 'Current Practice of Temporary Vena Cava Filter Insertion: A Multicenter Registry.' JVIR 2000; 11:83-88.
Rousseau et al., 'The 6-F Nitinol TrapEase Inferior Vena Cava Filter: Results of a Prospective Multicenter Trial.' J Vasc Interv Radiol 2001; 12:299-304.
Stoneham et al., 'Temporary Inferior Vena Cava Filters: In Vitro Comparison with Permanent IVC Filters.' JVIR 1995; 6:731-736.
Crochet et al., 'Evaluation of the LGM Vena Cava-Tech Infrarenal Vena Cava Filter in and Ovine Venous Thromboembolism Model.' J Vasc Interv Radiol 2001; 12:739-745.
Kaufman, 'Guidelines for the Use of Optional Retrievable Vena Cava Filters.' European Respiratory Disease 2007; 31-34.
Epstein et al., 'Experience with the Amplatz Retrievable Vena Cava Filter.' Radiology 1989; 172:105-110.
Inferior Vena Cava Filter, ISI Interventional & Surgical Innovations LLC. Product Brochure, Copyright 2008.
The Clot Stopper (online). Retrieved from the internet <URL:http://www.americanheritage.com/people/articles/web/20060715-pulmonary-embolism-blood-clot-lazar-greenfield-garman-kimmel-surgery-medical-doctor-surgeon.shtml>.
Simon Nitinol Filter, Versatile and Dependable Performance. Bard Peripheral Vascular (online). Retrieved from the internet <URL:http://www.bardpv.com_vascular/product.php?p=23>.
Aegisy Vena Cava Filter. Shenzhen Lifetech Scientific Inc. (online). Retrieved from the internet <URL:http://www.lifetechmed.com/english/product/product6.htm>.
Safe Flo Vena Cava Filter (online). Retrieved from the internet <URL:www.rafaelmedical.com>.
Aegisy Vena Cava Filter Product Description (online). Retrieved from the internet <URL:http://www.lifetechclinic.com/upload/article/vena/instruction_for_use.htm>.
Design History (online). Retrieved from the internet <URL:http://www.lifetechclinic.com/upload/article/vena/vena_cava_filter.htm>.
Crux Biomedical, Inc. Inferior Vena Cava Filter System Instructions for Use, IFU P/N 0001 Rev.B, DCO# 0027, Effective Date Feb. 2, 2007.
Smouse, 'Next Generation Filters: Are There Improvements Over the Existing Filters?', Powerpoint Presentation. University of Illinois College of Medicine at Peoria.
Kaufman, 'Vena Cava Filters as a Risk Factor for VTE'. Powerpoint Presentation at the SIR Foundation Jun. 2007 IVC Filter Research Consensus Panel.
Rectenwald, 'Are All IVC' s the Same.' Powerpoint Presentation at the SIR Foundation Jun. 2007 IVC Filter Research Consensus Panel.
Rogers, 'Vena Cava Filter Outcomes.' Powerpoint Presentation at the SIR Foundation Jun. 2007 IVC Filter Research Consensus Panel.
SIR Foundation Research Consensus Panel for the Development of a Research Agenda in Inferior Vena Cava Filters, Jun. 12, 2007—Herndon, VA. Powerpoint Presentation at the SIR Foundation Jun. 2007 IVC Filter Research Consensus Panel.
TrapEase Vena Cava Filter User's Instruction. Cordis Corp.
Corriere et al., 'Vena Cava Filters: An Update.' Future Cardiol 2006: 2(6): 695-707.
Mohan, C. et al. 'Comparative Efficacy and Complications of Vena Caval Filters.' J Vasc Surg 1995; 21:235-246.
Linsenmaier, U. et al., 'Indications, Management, and Complications of Temporary Inferior Vena Cava Filters.' Cardiovascular Intervent, Radiol 1998; 21(6): 464-469.
Asch et al. Radiology 2002; 29:173-176.

(56) References Cited

OTHER PUBLICATIONS

Cunliffe et al., 'A Fatal Complication of a Vena Cava Filter Associated with Pulmonary Thromboembolism.' Am J Forensic Med Pathol 2008; 29:173-176.
Joels et al., 'Complications of Inferior Vena Cava Filters.' Am Surg 2003; 69:654-659.
Pulmonary Embolism (online). Retrieved from internet <URL:http//www.mayoclinic.com/health/pulmonary-embolism/DS00429/DSECTION=complications>.
Cordis TrapEase Permanent Vena Cava Filter with the VisEase Angiographic Vessel Dilator (on line). Retrieved from <URL:http//www.mitek.com/home.jhtml?loc=USENG&page=viewcontent&contentid=09008b9880ffdcbf&nodekey=1Prod_Info/Type/Endovascular_Disease_Management/Vena_Cava_Filters&parentid=fc0de00100001215>.
Decousus et al., 'A Clinical Trial of Vena Caval Filters in the Prevention of Pulmonary Embolism in Patients with Proximal Deep-Vein Thrombosis.' The New England Journal of Medicine, Feb. 12, 1998; vol. 338, No. 7.
Notice of Allowance for U.S. Appl. No. 12/203,515, dated Jul. 13, 2011.
U.S. Appl. No. 13/774,598, filed Feb. 22, 2013, Snow.
Office Action dated Mar. 29, 2013 for U.S. Appl. No. 13/204,462.
Office Action dated Mar. 29, 2013 for U.S. Appl. No. 13/204,492.
International Search Report and Written Opinion dated Jan. 30, 2013 for PCT/US2012/047004.
International Search Report and Written Opinion dated Jan. 30, 2013 for PCT/US2012/047023.
International Search and Written Opinion dated Jun. 13, 2013 for PCT/US2013/027427.
Office Action dated Oct. 17, 2013 for U.S. Appl. No. 13/204,492.
Notice of Allowance dated Feb. 14, 2014 for U.S. Appl. No. 13/204,492.
Notice of Allowance dated Feb. 12, 2014 for U.S. Appl. No. 13/204,462.
Office Action dated Apr. 10, 2014 for U.S. Appl. No. 13/286,653.

\* cited by examiner (a)

(b)

(c)

(d)

(e)

(f)

(g)

(h)

(i)

(j)

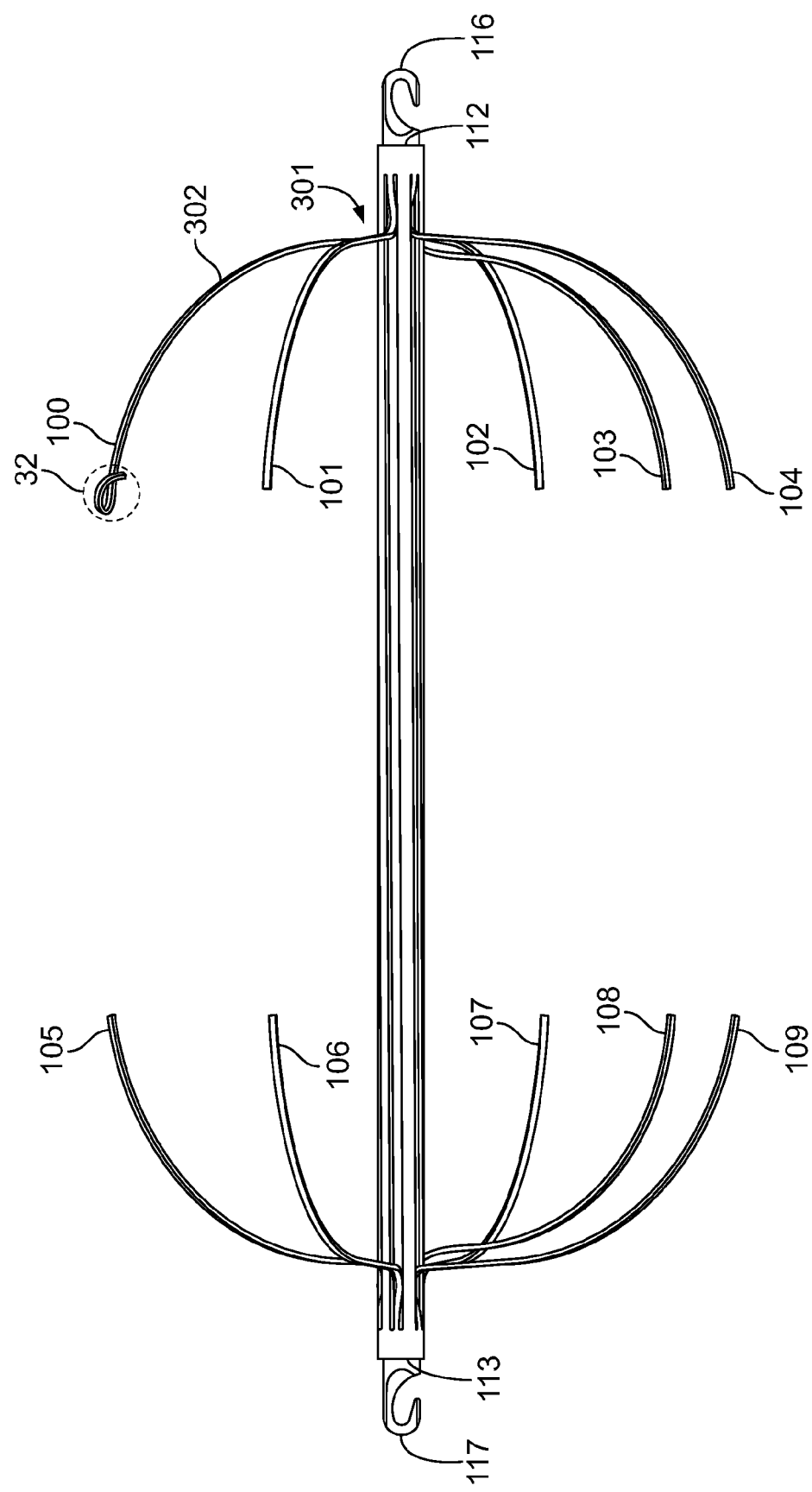

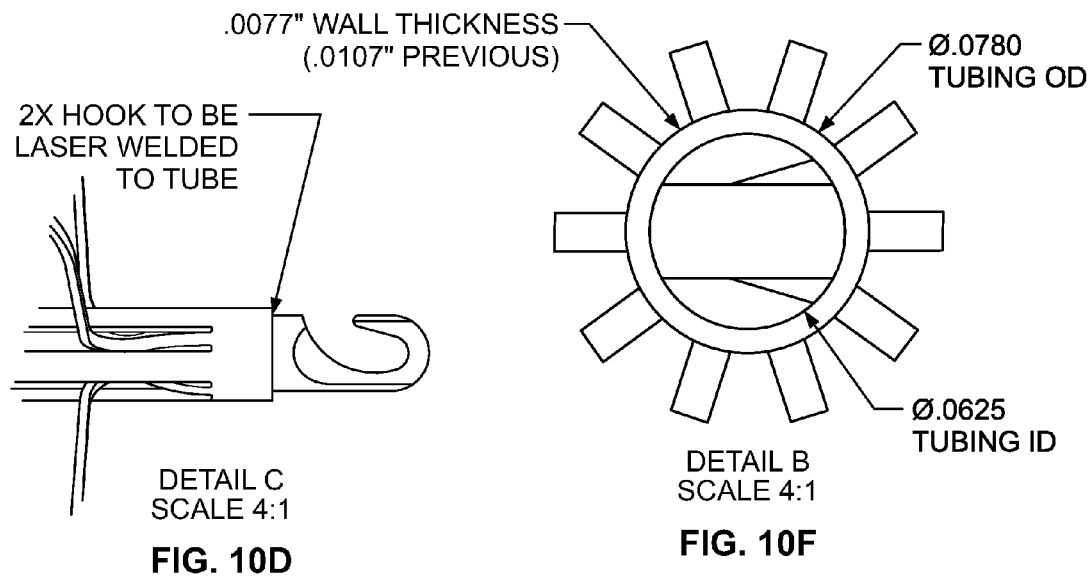
FIG. 10D
FIG. 10F
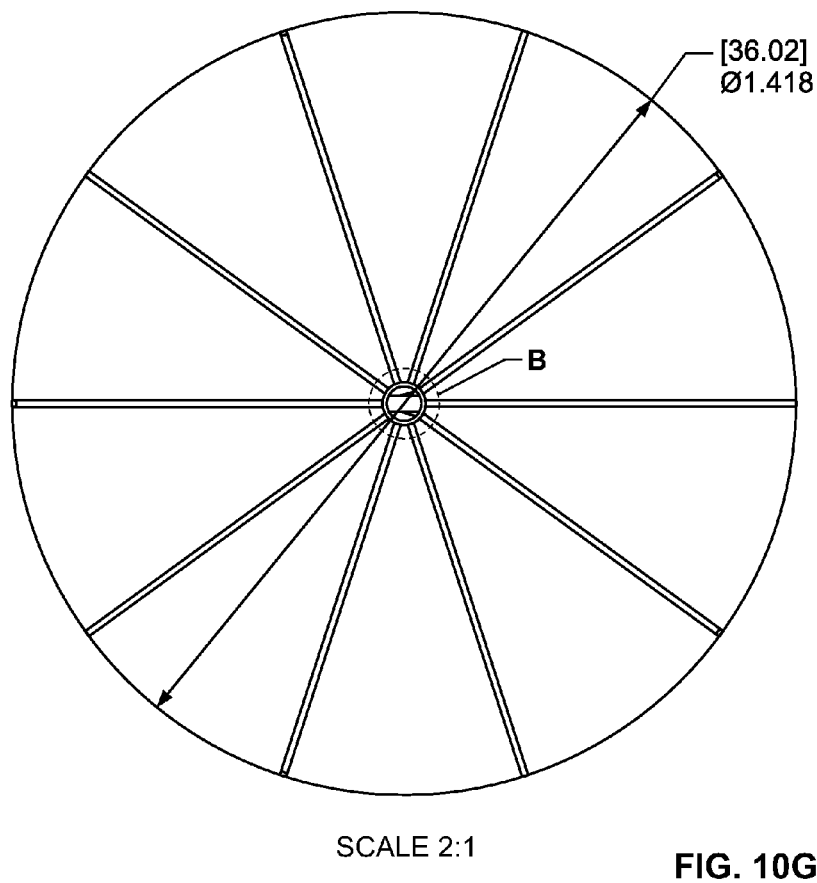
FIG. 10G

SCALE 1:1

PERCUTANEOUS RETRIEVABLE VASCULAR FILTER

CROSS REFERENCE TO RELATED APPLICATION

This application claims the benefit under 35 U.S.C. §119(e) of the U.S. Provisional Application Nos. 61/180,041 (filed on May 20, 2009) and 61/263,712 (filed Nov. 23, 2009). This application is a continuation-in-part of U.S. application Ser. No. 12/203,515, filed on Sep. 3, 2008, which claims the benefit under 35 U.S.C. §119(e) of the U.S. Provisional Application No. 60/967,704, filed on Sep. 7, 2007. This application also claims priority to PCT/US2010/023100, filed on Feb. 3, 2010, which claims priority to U.S. Provisional Application Nos. 61/149,482 (filed on Feb. 3, 2009) and 61/180,041 (filed on May 20, 2009).

FIELD OF THE INVENTION

The present invention relates to filters within a vessel. In particular, the present invention relates to retrievable vena cava filters which may be permanent or retrievable.

BACKGROUND OF THE INVENTION

Pulmonary embolism (PE) is a common health problem and a leading cause of death in all age groups. Most pulmonary emboli result from deep vein thrombosis (DVT) in the lower extremities or pelvis. The blood clots that form in another part of the body can migrate through the veins back to the heart and into the lungs, leading to a pulmonary infarct by depriving the blood and oxygen supply to a portion of the lung. An important risk factor for the development of DVT is venostasis; common scenarios include bedridden trauma patients and passengers on long airplane flights. Other causes of DVT are hypercoagulability and vessel wall inflammation. Corriere M, et al. Vena cava filters: an update. *Future Cardiol.* 2(6): 695-707 (2006).

Untreated PE is associated with a high mortality rate, generally held to be about 30%, with 11% of patients dying within the first hour. Patients with recurrent PE are at much higher risk. However, when the condition is promptly treated, the survival rate increases significantly. Pulmonary embolism [on-line]. Retrieved on Jul. 11, 2008 from http://www.mayoclinic.com/health/pulmonary-embolism/DS00429/DSECTION=complications. Anticoagulant therapy, such as heparin and warfarin, is the first line of treatment for PE. For patients in whom anticoagulation is contraindicated or inadequate, such as trauma and cancer patients, vena cava filters, including inferior vena cava (IVC) filters, provide alternative protection from PE. Corriere M, et al. Vena cava filters: an update. *Future Cardiol.* 2(6): 695-707 (2006). Vena cava filters are typically metal devices deployed under fluoroscopic guidance into the vena cava to prevent blood clots from migrating to the lungs. An IVC filter is usually placed below the level of the renal veins with the tip above the outflow of the renal veins. When the blood clot is captured in the top of the filter, it is then washed and lysed by the influx of the blood flow.

While some vena cava filters are permanently placed in the patient, there are potential complications associated with long-term filter implantation, including thrombotic occlusion of the vena cava, filter migration, filter fragmentation and filter embolization. Mohan C, et al. Comparative efficacy and complications of vena caval filters. *J. Vasc. Surg.* 21:235-246 (1995). See also U.S. Pat. No. 7,261,731. Nonpermanent filters, including temporary and retrievable filters, are recommended for patients having a limited period of risk for PE or the contraindication to anticoagulation. These types of filters are also recommended in adolescent and young-adult patients with normal life expectancy. Linsenmaier U et al. Indications, management, and complications of temporary inferior vena cava filters. *Cardiovasc. Intervent. Radiol.* 21(6): 464-469 (1998). Some temporary vena cava filters are attached to a wire or catheter, which is either exteriorized or secured subcutaneously for filter removal. The peripheral tether causes a certain degree of patient immobility and increases the risk of infection. Murray A, et al. *Radiology* 225:835-844 (2002).

In U.S. Pat. No. 6,391,045, a vena cava filter is disclosed that comprises a set of helical filter-wires joined at a central region and terminating in free ends constructed to engage the vessel wall. A major mid-portion of the length of the free-ended wires are generally helical forming shape. Anchoring is accomplished by a separate assembly formed of struts and anchoring devices. A trapezoid supporting strut assembly and other means for providing linear engagement with the wall of the vena cava are also disclosed. U.S. Pat. No. 6,059,825 discloses a retrievable vena cava filter formed of a single high-memory wire. The wire has a coiled cylindrical portion and a coiled conical portion. The coils of the cylindrical portion have a sufficiently large diameter contact the walls of the inferior vena cava with sufficient force to hold the coils in place against the inferior vena cava. The conical portion of the wire has a segment that aids in the removing of the filter from the vena. The vena cava filter of U.S. Pat. No. 5,954,741 features an inflatable balloon at or near the distal end of an elongate flexible multiple-lumen core or stem. The balloon is deflated prior to insertion; it is inflated to become a filter when properly positioned in the vein, and finally it is deflated for removal purposes.

In the U.S.A., there are currently six FDA-approved permanent vena cava filters with different shapes, configurations, sizes and materials. They include the stainless steel Greenfield filter (Boston Scientific, Natick, Mass.), the Bird's Nest filter (Cook, Bloomington, Ind.), the Simon Nitinol Filter (Bard, Tempe, Ariz.), the TrapEase filter (Cordis, Miami Lakes, Fla.), the Vena-Tech filter (B. Braun Medical, Evanston, Ill.) and the G2 filter (Bard, Tempe, Ariz.). There are only two FDA-approved retrievable vena cava filters: the Günter-Tulip filter (Cook, Bloomington, Ind.) and the OptEase filter (Cordis, Miami Lakes, Fla.). Corriere M, et al. Vena cava filters: an update. *Future Cardiol.* 2(6): 695-707 (2006).

Retrievable vena cava filters are designed with specific features, so depending on the individual situation, they may either be left in the vessel permanently or be retrieved. While the versatility of retrievable filters makes them favorable options, in clinical practice, a large number of the retrievable filters are prone to migration and tilt. Filters have been reported to migrate to the heart, pulmonary vasculature, and distally, along with subsequent vascular perforation due to filter strut extrusion. Cunliffe C, et al. A fatal complication of a vena cava filter associated with pulmonary thromboembolism. *Am. J. Forensic. Med. Pathol.* 29: 173-176 (2008). Filter tilt seriously reduces the filtering efficiency. The tilt of greater than 14 degrees from the longitudinal axis is considered to be associated with the increased incidence of recurrent PE. Joels C, et al. Complications of inferior vena cava filters. *Am Surg.* 69:654-659 (2003). The migration or tilt further makes it difficult or impossible to retrieve the filter.

It is, therefore, desired to develop a retrievable vena cava filter that has high filtering capacity with no impedance to flow, is securely fixed on the vena cava wall (non-migrating and non-tilting), and can be easily retrieved. It is also advantageous to develop a retrievable filter than can be deployed at the patient's bedside without the need of fluoroscopy.

SUMMARY OF THE INVENTION

It is an object of the present invention to provide a filter comprising a first tube and a second tube. The first tube has a plurality of a first set of slots, a plurality of a second set of slots, and a plurality of a first set of expandable legs. Each leg of the first set has an end secured to the first tube and a free end. The second tube has a plurality of a second set of expandable legs and a plurality of a third set of expandable legs. Each leg of the second set has an end secured to the second tube and a free end. Each leg of the third set comprises an expandable segment and has both ends secured to the second tube. Each slot of the first set of slots is positioned at a radial position on the first tube allowing for deployment of each expandable leg of the second set. Each slot of the second set of slots is positioned at a radial position on the first tube allowing for deployment of the expandable segment in each leg of the third set, the slots being oriented parallel to the cylindrical axis of the first tube. The second tube's external diameter is less than the first tube's internal diameter. The second tube is inserted into the first tube such that the free end of each leg in the first set is oriented in a direction opposite to the free end of each leg in the second set. The filter may be encased in a catheter in an undeployed state. Each expandable leg of the first and second sets can be deployed and form a cage. The cage may form a sphere shape when the expandable legs of the first and second set are deployed; the expandable segment of each expandable leg in the third set may form a curvilinear shape when deployed; the barb on the end of free end may be inserted into a vessel wall when the filter is deployed. Each expandable leg of the first set and second set may have at least one barb on the free end. At least one end of the first tube and/or the second tube may have at least one notch.

Each of the expandable legs of the first and second sets may comprise memory metal. The expandable segment of the expandable legs of third set may comprise memory metal. The number of expandable legs in the first set and second set may range from about 2 to about 20, from about 4 to about 15, or from about 4 to about 10. In one embodiment, the number of expandable legs in the first set is four, A, B, C and D, the number of legs in the second set is four, E, F, G and H, and the number of legs in the third set is four, I, J, K and L. The expandable legs in the first set are secured at radial positions along the first tube's circumference ranging from about 0° to about 90° for A, about 90° to about 180° for B, about 180° to about 270° for C, and about 270° to about 360° for D. In another embodiment, the expandable legs in the second set are secured at radial positions along the second tube's circumference ranging from about 0° to about 90° for E, about 90° to about 180° for F, about 180° to about 270° for G, and about 270° to about 360° for H. The radial positions of the first set and second set of expandable legs may be symmetrical or asymmetrical.

The present invention provides for a method for retrieving the filter. The method comprises the steps of, inserting a catheter into a vessel where the filter is positioned on the vessel wall, pushing a snare through the catheter until the snare grabs the notch, pulling back on the snare to exert tension on the filter, pushing the catheter over the snare and each expandable leg of the third set until each expandable leg of the third set straightens, each expandable leg of the first set retracts from the vessel wall, and each expandable leg of the second set retracts from vessel wall, encompassing the expandable legs of the first, second and third sets in the catheter and, withdrawing the filter.

The present invention further provides for a filter comprising a tube having a plurality of a first set of expandable legs and a plurality of a second set of expandable legs. Each leg of the first set and the second set has an end secured to the tube and a free end. The free end of each leg in the first set is oriented in a direction opposite to the free end of each leg in the second set. At least one end of the filter has at least one notch. The filter may be encased in a catheter in an undeployed state. Each expandable leg of the first and second sets may be deployed, and may form a cage. Each expandable leg of the first set and second set may have at least one barb on the free end. The number of expandable legs in the first set and second set may range from about 2 to about 20, from about 4 to about 15, or from about 4 to about 10. In one embodiment, the number of expandable legs in the first set is five, and the number of legs in the second set is five. Each leg of the first and the second sets may be bent inward at the end closest to the tube.

The filter may be retrieved by a method comprising the steps of: inserting a catheter into a vessel where the filter is positioned on the vessel wall, pushing a snare through the catheter until the snare grabs the notch on the tube closest to the first set of expandable legs, pulling back on the snare to exert tension on the filter, pushing the catheter over each expandable leg of the first set until each expandable leg refracts from the vessel wall, continuing pushing the catheter over the second set of expandable legs until each expandable leg of the second set inverts and retracts from vessel wall, encompassing the expandable legs of the first and second sets in the catheter and, withdrawing the filter.

The present invention also provides a filter comprising a first tube and a second tube. The first tube has a plurality of a first set of expandable legs and a plurality of a first set of slots Each leg of the first set has an end secured to the first tube and a free end. The second tube has a plurality of a second set of expandable legs. Each leg of the second set has an end secured to the second tube and a free end. The free end of each leg in the first set is oriented in a direction opposite to the free end of each leg in the second set. Each slot of the first set on the first tube is positioned at a radial position allowing for deployment of each leg of the second set. The slots are oriented parallel to the cylindrical axis of the first tube. The second tube's external diameter is less than the first tube's internal diameter. The second tube is inserted into the first tube. There may be a cap at one end of the first tube. At least one end of the first tube may have at least one notch. The filter may be retrieved by a method comprising the steps of, inserting a catheter into a vessel where the filter is positioned on the vessel wall, pushing a snare through the catheter until the snare grabs the notch on the first tube, pushing a wire through the catheter and the inner space of the first tube until the wire reaches the second tube or pin, pulling back on the snare to exert tension on the filter, pushing the catheter over each expandable leg of the first set until each expandable leg of the first set refracts from the vessel wall, pushing the wire to push the second tube or pin away from the snare to exert tension on the second set of expandable legs until the second set of expandable legs retract from the vessel wall, encompassing the expandable legs of the first and second sets in the catheter and, withdrawing the filter.

The present invention provides for a filter comprising a first tube and a second tube. The first tube has a plurality of a first set of slots and a plurality of a second set of slots. The second tube has a plurality of a first set of expandable legs and a plurality of a second set of expandable legs. Each leg of the first set and the second set has an end secured to the second tube and a free end. The free end of each leg in the first set is oriented in a direction opposite to the free end of each leg in the second set. Each slot of the first set of slots on the first tube is positioned at a radial position allowing for deployment of each expandable leg of the first set. Each slot of the second set of slots on the first tube is positioned at a radial position allowing for deployment of each leg of the second set. The slots are oriented parallel to the cylindrical axis of the first tube. The second tube's external diameter is less than the first tube's internal diameter. The second tube is inserted into the first tube. At least one end of the first tube may have at least one notch. The filter may be retrieved by a method comprising the steps of, inserting a catheter into a vessel where the filter is positioned on the vessel wall, pushing a snare through the catheter and the inner space of the second tube until the snare grabs the notch on the first tube proximal to the second set of expandable legs, pulling back on the snare to exert tension on the filter, pushing the catheter over each expandable leg of the first set until each expandable leg retracts from the vessel wall, meanwhile, pulling back on the snare and the first tube to exert tension on the second set of expandable legs until each expandable leg of the second set retracts from vessel wall, encompassing the expandable legs of the first and second sets in the catheter and, withdrawing the filter.

The filter may alternatively be retrieved from the other end using a similar mechanism.

BRIEF DESCRIPTION OF THE DRAWINGS

FIG. 1b shows a side view of the filter in FIG. 1a.

FIG. 2a shows a side view of the first tube of the filter in FIG. 1a.

FIG. 2b shows a side view of the second tube of the filter in FIG. 1a.

FIG. 4b shows a side view of the filter in FIG. 4a.

FIG. 5a shows a side view of the first tube of the filter in FIG. 4a.

FIG. 5b shows a side view of the second tube of the filter in FIG. 4a.

FIG. 6b shows a side view of the filter in FIG. 6a.

FIG. 7a shows the side view of the first tube of the filter in FIG. 6a.

FIG. 7b shows the side view of the second tube of the filter in FIG. 6a.

FIG. 8b shows a side view of the filter in FIG. 8a.

FIG. 9b shows a side view of the filter in FIG. 9a.

FIG. 10b shows a side view of the filter in FIG. 10a.

FIG. 10c shows another side view of the filter in FIG. 10a.

FIG. 10d shows the details of one end of the filter including the hook.

FIG. 10e shows another perspective view of the filter in FIG. 10a.

FIG. 10f shows a partial perspective view of the filter in FIG. 10a as it would appear looking from 501 to 502.

FIG. 10g shows a perspective view of the filter in FIG. 10a as it would appear looking from 501 to 502.

FIG. 11b shows a side view of the filter in FIG. 11a.

FIG. 12 shows a side view of the first tube of the filter in FIG. 11a.

FIG. 13a shows a side view of the second tube of the filter in FIG. 11a.

FIG. 14b shows a side view of the filter in FIG. 14a.

FIG. 15 shows a side view of the first tube of the filter in FIG. 14a.

FIG. 16 shows a side view of the second tube of the filter in FIG. 14a.

FIG. 18 shows a side view of the second tube of the filter in FIG. 17a.

FIG. 19 shows a side view of the first tube of the filter in FIG. 17a.

FIG. 26b shows retrieval of the filter in FIG. 26a.

FIG. 27b shows another perspective view of the filter in FIG. 27a.

FIG. 29 shows retrieval of the filter shown in FIG. 11a.

FIG. 30 shows retrieval of the filter shown in FIG. 1a.

FIG. 32 shows retrieval of the filter shown in FIG. 6a.

FIG. 33 shows retrieval of the filter shown in FIG. 8a.

FIG. 34 shows retrieval of the filter shown in FIG. 9a.

DETAILED DESCRIPTION OF THE INVENTION

Figure 1A:
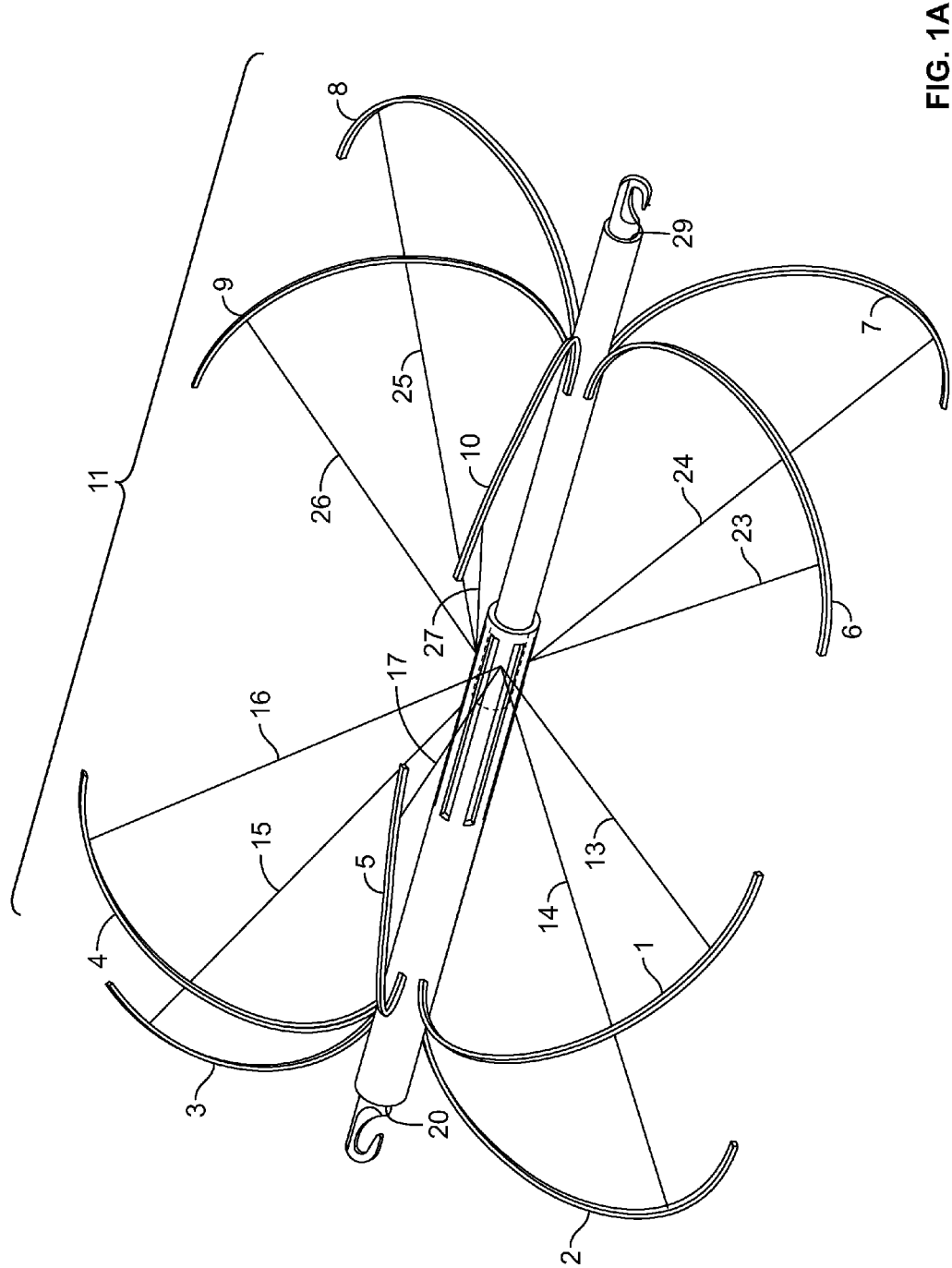
FIG. 1a shows a perspective view of one embodiment of the filter where there is a plurality of connectors attached to both sets of expandable legs.

The present invention provides a vena cava filter (the "filter") that may be permanent or retrievable and which may be used for the temporary or permanent prevention of pulmonary embolism (PE). The filter can be inserted into the body percutaneously through a vein such as the femoral vein or the jugular vein. The filter may have a tube-within-tube structure that can yield semispheres which may or may not overlap upon deployment. Together the semispheres form a cage. The filter may be formed of a single tube. The filter is positioned within the vena cava at or below the juncture of the renal vein. The semi-spheres or cages of the filter ensure stable and non-migrating vena cava filtration. Because the semi-spheres are collapsible, the filter can easily be retrieved from the vena cava. In certain embodiments, the filter can be retrieved from either end.

The filter may be formed from a first tube and a second tube. The first tube has a plurality of a first set of slots, a plurality of a second set of slots, and a plurality of a first set of expandable legs. The second tube has a plurality of a second set of expandable legs and a plurality of a third set of legs. Each leg of the first set has an end secured to the first tube and a free end. Each leg of the second set has an end secured to the second tube and a free end. The free end of each leg in the first set is oriented in a direction opposite to the free end of each leg in the second set. Each leg of the third set comprising an expandable segment and having both ends secured to the second tube. The first set of slots on the first tube is positioned at radial positions allowing for deployment of the second set of legs. The second set of slots on the first tube is positioned at radial positions allowing for deployment of the expandable segment in each leg of the third set. Each slot on the first tube is oriented parallel to the cylindrical axis of the first tube. The radial position of one set of expandable legs may be off-set from the radial position of a different set of expandable legs or may be the same. For example, the radial positions of the second set of expandable legs may be the same as or be off-set from the radial positions of the first set of expandable legs. The second tube's external diameter may be less than the first tube's internal diameter. The filter may be formed by inserting the second tube into the first tube. A cage may be formed comprising the expandable legs of the first and second sets. The cage may form a sphere shape when the expandable legs of the first and second sets are deployed. The free end of each leg in the first set may be oriented in a direction opposite to the free end of each leg in the second set. Alternatively, the free end of each leg in the first set may be oriented in a direction the same as the direction of the free end of each leg in the second set.

In one embodiment, the number of expandable legs in the first set is five, A, B, C, D and E, the number of legs in the second set is five, F, G, H, I and J, the number of legs in the third set is five, K, L, M, N and O. The expandable legs in the first set are secured at radial positions along the first tube's circumference ranging from about 0° to about 72° for A, about 72° to about 144° for B, about 144° to about 216° for C, about 216° to about 288° for D and about 288° to about 360° for E. In one embodiment, the radial positions of the first set of expandable legs are symmetrical, e.g., A is at 0°, B is at 72°, C is at 144°, D is at 216° and E is at 288°. The radial positions of the first set of expandable legs may also be asymmetrical. The expandable legs in the second set are secured at radial positions along the second tube's circumference ranging from about 0° to about 72° for F, about 72° to about 144° for G, about 144° to about 216° for H, about 216° to about 288° for 1 and about 288° to about 360° for J. The radial positions of the second set of expandable legs, F, G, H, I and J may be symmetrical or asymmetrical. The radial positions of the second set of expandable legs may be off-set from the radial position of the first set of expandable legs. For example, if the radial positions of the first set of expandable legs are 0° for A, 72° for B, 144° for C, 216° for D and 288° for E, and the second set of expandable legs are off-set 10° from the first set of expandable legs, then the second set of expandable legs are positioned at about 10° for F, about 82° for G, about 154° for H, about 226° for 1 and about 298° for J. The radial positions of the second set of expandable legs may be the same as or may differ from the first set of expandable legs symmetrically or asymmetrically.

In a further embodiment, at least one end of the first tube and/or the second tube has at least one notch. In a preferred embodiment, there is one notch at the end proximal to the expandable legs on each tube for retrieval of the filter from either end. Prior to insertion into the vena cava, the filter may be encased in a catheter. The free ends of each expandable leg may have at least one barb. The legs may have various shapes, including rectangular strips, wires, tubes, rods, threads, or any other desired structure. The legs may be straight, curved, tapered or have multiple angles. For example, the leg may be curved inward at its free end to reduce penetration into the vessel wall. The shapes, configurations or dimensions of various portions of each leg may vary or be the same. The shapes, configurations, dimensions or angles of different legs of the filter may be different or may be the same. The legs may be notched, barbed, hooked or in any structure that anchors the legs in the vessel wall without interfering with the retrieval of the filter. The number of legs in each set may be three, four, five or any other number that is able to ensure the stability of the filter when deployed and the efficient vena cava filtration. The number of expandable legs in each set may range from 2-20, from 4-15, from 4-10, or from 5-10. The number of legs in each set may be three, four, five, six or any other number that is able to ensure the stability of the filter when deployed and efficient vena cava filtration. There may be an equal or unequal number of legs in each of the first and second sets. The legs may be positioned symmetrically or asymmetrically at radial positions along the circumference of the tube. If the legs are positioned symmetrically, then the radial distance between each pair of legs, e.g., A-B and B-C is equal. The radial positions listed for the legs here are only provided for illustration purposes and the legs may be positioned by one of ordinary skill in the art without undue experimentation at any point along the circumference of the tube. For example, if there are 8 legs in the first expandable set, the positioning of the legs may be determined by dividing 360° by N where N is the number of legs. Where N=8, the legs may be positioned symmetrically at 45° intervals around the circumference of the tube. The expandable legs may then be positioned at off-set intervals on the circumference different from the 45° intervals, i.e., 0° (360°). 45°, 90°, 135°, 180°, 225°, 270°, 315°.

The present invention also provides a filter formed from a first tube and a second tube. The first tube has a plurality of a first set of slots, a plurality of a first set of expandable legs and a plurality of a first set of connectors. The second tube has a plurality of a second set of expandable legs and a plurality of a second set of connectors. Each leg of the first set has an end secured to the first tube and a free end. Each connector of the first set has an end attached to a leg of the first set and an end attached to the second tube. In one embodiment, there is at least one connector attached to each leg of the first or second set. In another embodiment, there is at least one leg of the first set without connectors attached. Each leg of the second set has an end secured to the second tube and a free end. Each connector of the second set has an end attached to a leg of the second set and an end attached to the first tube. The free end of each leg in the first set is oriented in a direction opposite to the free end of each leg in the second set. The first set of slots on the first tube is positioned at radial positions allowing for deployment of the first set of connectors. Each slot on the first tube is oriented parallel to the cylindrical axis of the first tube. The radial positions of the second set of expandable legs may be the same as or be off-set from the radial positions of the first set of expandable legs. In one embodiment, the radial positions of the second set of expandable legs are the same as the radial positions of the first set of expandable legs. The second tube's external diameter may be less than the first tube's internal diameter. The filter may be formed by inserting the second tube into the first tube. A cage may be formed comprising the expandable legs of the first and second sets. The cage may form a sphere shape when the expandable legs of the first and second sets are deployed.

The present invention further provides a filter comprising a first tube having a plurality of a first set of connectors and a second tube having a plurality of a first set of expandable legs and a plurality of a second set of expandable legs. Each leg of the first and the second set has an end secured to the second tube and a free end. The free end of each leg in the first set is oriented in a direction opposite to the free end of each leg in the second set. Each connector of the first set has an end secured to the first tube. In one embodiment, there is at least one connector attached to each leg of the first set. In another embodiment, there is at least one leg of the first set without connectors attached. The second tube's external diameter is less than the first tube's internal diameter. The filter may be formed by inserting the second tube into the first tube. The number of expandable legs in the first and second set may be the same or be different. The radial positions of the first and second sets of expandable legs may be the same or be different. In a preferred embodiment, the numbers of expandable legs of the first set and second set are the same. The redial positions of the first set of expandable legs are off-set from the radial positions of the second set of expandable legs. There is at least one notch at one end of the first tube for retrieval of the filter. A semi-sphere shape may be formed comprising the first or the second sets of expandable legs and the two semi-sphere shapes may overlap when the expandable legs of the first and second sets are deployed.

In a fourth embodiment, the present invention provides a filter comprising a first tube having a plurality of a first set of expandable legs and a plurality of a first set of slots, and a second tube having a plurality of a second set of expandable legs. Each leg of the first set has an end secured to the first tube and a free end, each leg of the second set has an end secured to the second tube and a free end. The free end of each leg in the first set is oriented in a direction opposite to the free end of each leg in the second set. Each slot of the first set on the first tube is positioned at a radial position allowing for deployment of each leg of the second set. The slots are oriented parallel to the cylindrical axis of the first tube. The radial positions of the second set of expandable legs may be the same as or be off-set from the radial positions of the first set of expandable legs. In one embodiment, the radial positions of the second set of expandable legs are off-set from the radial positions of the first set of expandable legs. The second tube's external diameter may be less than the first tube's internal diameter. There is at least one notch at one end of the first tube. There may be one cap at one end of the first tube. The filter may be formed by inserting the second tube into the first tube.

In a fifth embodiment, the present invention provides a filter comprising a tube having a plurality of a first set of expandable legs, a plurality of a second set of expandable legs and a plurality of a third set of expandable legs. Each leg of the first set, second set and third set has an end secured to the tube and a free end. The free end of each leg is oriented in the same direction. The number of expandable legs in the first, second and third set may be the same or be different. The radial positions of the first set, the second set and the third set of slots may be same or may be different. In a preferred embodiment, the number of expandable legs and the redial positions of the first, second and third set of expandable legs are the same. After deployment, the free end of each leg is oriented in the same direction pointing to the end of the tube distal to the first set of expandable legs. There is at least one notch at the end of the tube proximal to the first set of expandable legs for retrieval of the filter. A tree shape may be formed comprising the first, second and third sets of expandable legs when the expandable legs of the first, second and third sets are deployed. The filter may have two, three, four, or any other number of sets of legs that is able to ensure the stability of the filter when deployed and efficient vena cava filtration.

In a sixth embodiment, the present invention provides a filter comprising a tube having a plurality of a first set of expandable legs and a plurality of a second set of expandable legs. Each leg of the first set and the second set has an end secured to the tube and a free end. The free end of each leg in the first set is oriented in a direction opposite to the free end of each leg in the second set. Each leg of the first and the second sets is bent inward at the end closest to the tube for easy retrieval of the filter. Each leg of the first and second set may have at least one barb at its free end. The radial positions of the second set of expandable legs may be the same as or be off-set from the radial positions of the first set of expandable legs. A cage may be formed comprising the expandable legs of the first and second sets. The cage may form a sphere shape when the expandable legs of the first and second sets are deployed. At least one end of the tube has at least one notch for retrieval of the filter. The free end of each leg in the first set may be oriented in a direction opposite to the free end of each leg in the second set. Alternatively, the free end of each leg in the first set may be oriented in a direction the same as the direction of the free end of each leg in the second set.

In a seventh embodiment, the filter is formed from a first tube and a second tube. The first tube has a plurality of a first set of slots and a plurality of a second set of slots. The second tube has a plurality of a first set of expandable legs, and a plurality of a second set of expandable legs. Each leg of the first set and the second set has an end secured to the second tube and a free end. The free end of each leg in the first set is oriented in a direction opposite to the free end of each leg in the second set. The first set of slots on the first tube are positioned at radial positions allowing for deployment of the first set of expandable legs. The second set of slots on the first tube are positioned at radial positions allowing for the deployment of the second set of expendable legs. Each slot on the first tube is oriented parallel to the cylindrical axis of the first tube. The radial positions of the second set of expandable legs may be the same as or be off-set from the radial positions of the first set of expandable legs. In one embodiment, the radial positions of the second set of expandable legs are the same as the radial positions of the first set of expandable legs. The second tube's external diameter may be less than the first tube's internal diameter. The filter may be formed by inserting the second tube into the first tube. The diameter of the first tube may be the same as the diameter of the second tube or may be different. A cage may be formed comprising the expandable legs of the first and second sets. The cage may form a sphere shape when the expandable legs of the first and second sets are deployed.

In a seventh embodiment, the filter comprises a first tube having a plurality of a first set of slots and a plurality of a first set of expandable legs, and a second tube having a plurality of a second set of slots and a plurality of second set of expandable legs. Each leg of the first set has an end secured to the first tube and a free end. Each leg of the second set has an end secured to the second tube and a free end. The free end of each leg in the first set is oriented in a direction opposite to the free end of each leg in the second set. The first set of slots on the first tube are positioned at a radial position allowing for deployment of the second set of expandable legs on the second tube, the second set of slots on the second tube are positioned for the deployment of the first set of expendable legs on the first tube. Each slot is oriented parallel to the cylindrical axis of the tubes. The radial positions of the first set of slots are off-set from the radial positions of the first set of expandable legs on the first tube. The radial positions of the second set of slots are off-set from the radial positions of the second set of expandable legs on the second tube. The diameter of the first tube may be the same as the diameter of the second tube or may be different. The filter is formed by inserting the first set of expandable legs into the second tube, and the second set of expandable legs into the first tube, so that the first set of expandable legs on the first tube are deployed through the second set of slots on the second tube, and the second set of expandable legs on the second tube are deployed through the first set of slots on the first tube. After deployment, the free end of each leg in the first set is oriented in a direction opposite to the free end of each leg in the second set. At least one end of the first or second tube has at least one notch for retrieval of the filter. In a further embodiment of the present invention, one end of the first tube and/or one end of the second tube have at least one notch. In a preferred embodiment, there is one notch at one end of the first tube and one notch at one end of the second tube for retrieval of the filter from either end.

In one embodiment, the present filter comprises a plurality of a first set of expandable legs and a plurality of a second set of expandable legs. A plurality of legs divide the space within a vessel to capture clots of clinically meaningful dimensions that put patient at risk. The free end of each leg in the first set is oriented in a direction opposite to the free end of each leg in the second set. The opposing direction of the legs help to capture clinically meaningful clots. Alternatively, the free end of each leg in the first set may be oriented in a direction the same as the direction of the free end of each leg in the second set. The radial positions of the second set of expandable legs are off-set from the radial positions of the first set of expandable legs. The off-set orientation optimizes clot capture. The number of legs in each set may be four, five, six or any other suitable number. The legs are connected by a central positioning bar to provide discontinuous wall contact while optimizing clot capture. The two sets of legs optimize filtration while minimizing wall contact and maximizing clot capture. The lack of longitudinal connectors between legs of two sets provides discontinuous vessel wall contact, and reduces length of contact of the filter with the vessel wall. Either set of legs forms a curved shape, which may or may not be to degree of sphere. A leg may be curved inward at its free end to reduce penetration into cava wall. Force load is distributed over the length of leg contacting vessel wall (i.e., greater than single point contact). The force projected by curved legs is less than the force to penetrate cava wall. Interrupted legs provide minimal wall incorporation. The shape and length of the legs help maintain "pivot-free" from placement position (i.e., prevents relative re-positioning of filter) (self-centering filter). The width of the leg may be less than the width of the corresponding receiving slot in the outer tube. The positioning bar is a longitudinal bar which engages two sets of legs for positioning access for placement and retrieval. The positioning bar allows axial centering within the vessel, while preventing "axial tilt". The tolerance for inaccuracies in final deployment is less than acceptable clinical range (about 15° tolerance). The free end of the leg may have at least one barb, which serves as anchors and minimizes tissue disruption.

The entire deployment process of the filter can be controlled. The design of the filter provides tolerance for inaccuracies in final deployment in terms of clot trapping. Repositioning contact with device may be maintained. The filter may be retrieved through femoral removal.

In another embodiment, the filter has a tube-within-tube structure, where the inner tube slides within the outer tube. The elements of the inner tube can be manipulated by changing the relative position of the two tubes (i.e., the legs on the inner tube expand through slots in the outer tube when properly positioned). There is a closing mechanism on the inner tube. The closing mechanism is movable through slots in the outer tube, and, therefore, expands through slots to open legs on the inner tube and collapses within slots to close legs on the inner tube. The closing mechanism can be a set of legs which may form a curvilinear shape when deployed (e.g, formed in the shape of an egg beater). The closing mechanism may be a component formed in the shape of an L, a bicycle handle, a triangle, or any other suitable shape that facilitates the closing of at least one set of legs during retrieval of the filter. For example, when the closing mechanism is in the shape of a triangle, the triangle can be longer on one side and shorter on the other. During retrieval, as a catheter is pushed over the filter, the catheter first gets in touch with the taller side of the triangle, and continues to push the triangle forward and into the slots of the outer tube. The triangle is further driven down by the catheter into the outer tube, thereby closing the distal set of legs. The present filter comprises a plurality of a first set of expandable legs and a plurality of a second set of expandable legs. The free end of each leg in the first set is oriented in a direction opposite to the free end of each leg in the second set. The radial positions of the second set of expandable legs are off-set from the radial positions of the first set of expandable legs. The legs are connected by a central positioning bar with closing mechanism whose expanded diameter is greater than the expanded diameter of the set of legs located closest to the closing mechanism. Accordingly, the closing mechanism is located outside the proximal set of legs, and controls closing of the distal set of legs. This filter provides good clinical utility in deployment and retrieval through easy manipulation and repositioning control. During delivery, the tube may be pushed with a ratcheting system. A catheter covers both sets of legs in closed position during delivery. After filter is positioned in the vessel, the catheter is pulled back for leg opening. The catheter may have compression ring which is radiopaque. During retrieval, the closing mechanism on the inner tube collapses within slots to close legs on the inner tube. A catheter is advanced to engage proximal closing mechanism to collapse distal legs first; the catheter is then advanced to collapse proximal legs and continues over collapsed distal legs. A ratchet control mechanism may be used to control the catheter.

In a further embodiment, the filter comprises a plurality of a first set of expandable legs and a plurality of a second set of expandable legs. The free end of each leg in the first set is oriented in a direction opposite to the free end of each leg in the second set. The radial positions of the second set of expandable legs are off-set from the radial positions of the first set of expandable legs. The legs are connected by a central positioning bar. During delivery, the tube may be pushed with a ratcheting system; the catheter encasing the filter may be pulled back for distal delivery. The filter may be retrieved with a snare and a catheter. The snare extends from end of a tube, and is off axis (i.e., snare is not centered via the tube). The snare extends past distal legs and is pulled back to collapse distal legs. The catheter advances to collapse proximal legs and then extends over distal legs.

Figure 1B:
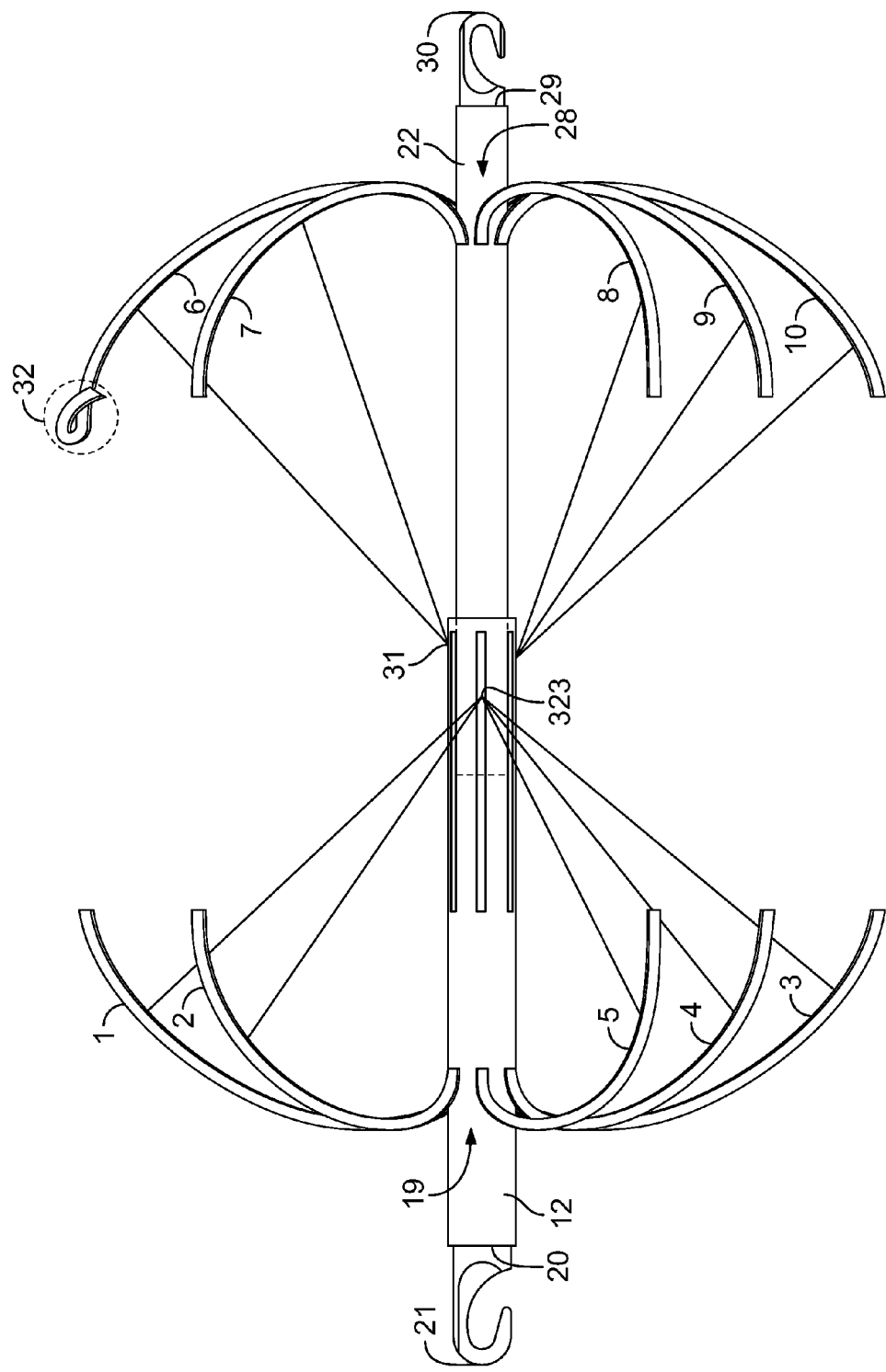

One embodiment of the assembled filter of the present invention is shown in FIGS. 1a, b and c. The filter comprises a first tube and a second tube that is inserted into the first tube. The external diameter of the second tube is smaller than the internal diameter of the first tube. The filter comprises a first set of expandable legs, 1, 2, 3, 4 and 5, a second set of expandable legs 6, 7, 8, 9 and 10, a first set of connectors 13, 14, 15, 16, 17 and a second set of connectors 23, 24, 25, 26, 27. The expandable legs of the first and second sets form a cage 11. The cage 11 may take the shape of a ball or sphere when deployed. Each of the first set of connectors 13, 14, 15, 16, 17 has an end attached to each of the first set of expandable legs 1, 2, 3, 4, 5 and the other end attached to the second tube 22 at point 323 (FIG. 1b). Each of the second set of connectors 23, 24, 25, 26, 27 has an end attached to each leg of the second set 6, 7, 8, 9, 10 and the other end attached to the first tube 12 at point 31 (FIG. 1b).

Figure 1C:
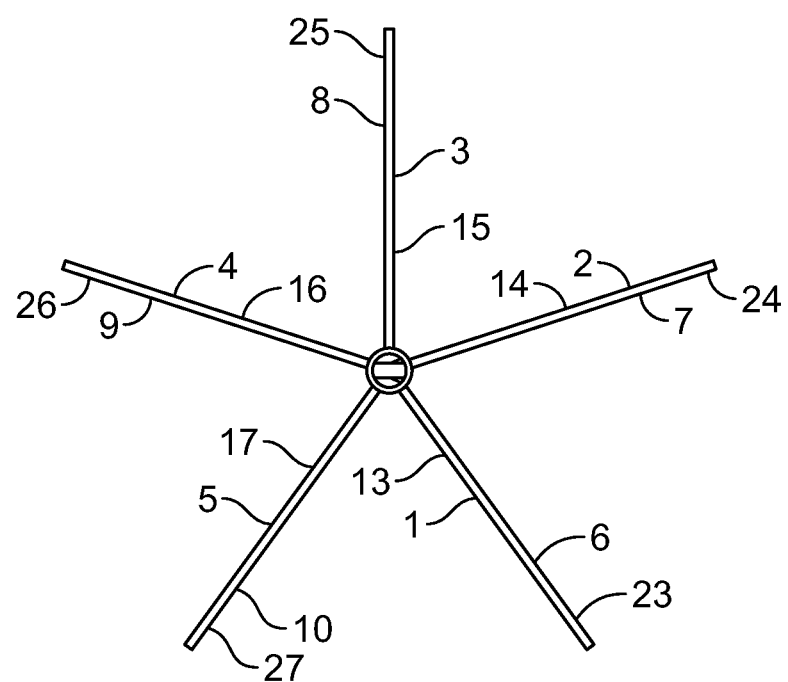
FIG. 1c shows a perspective view of the filter in FIG. 1a as it would appear looking from 20 to 29.
Figure 2A:
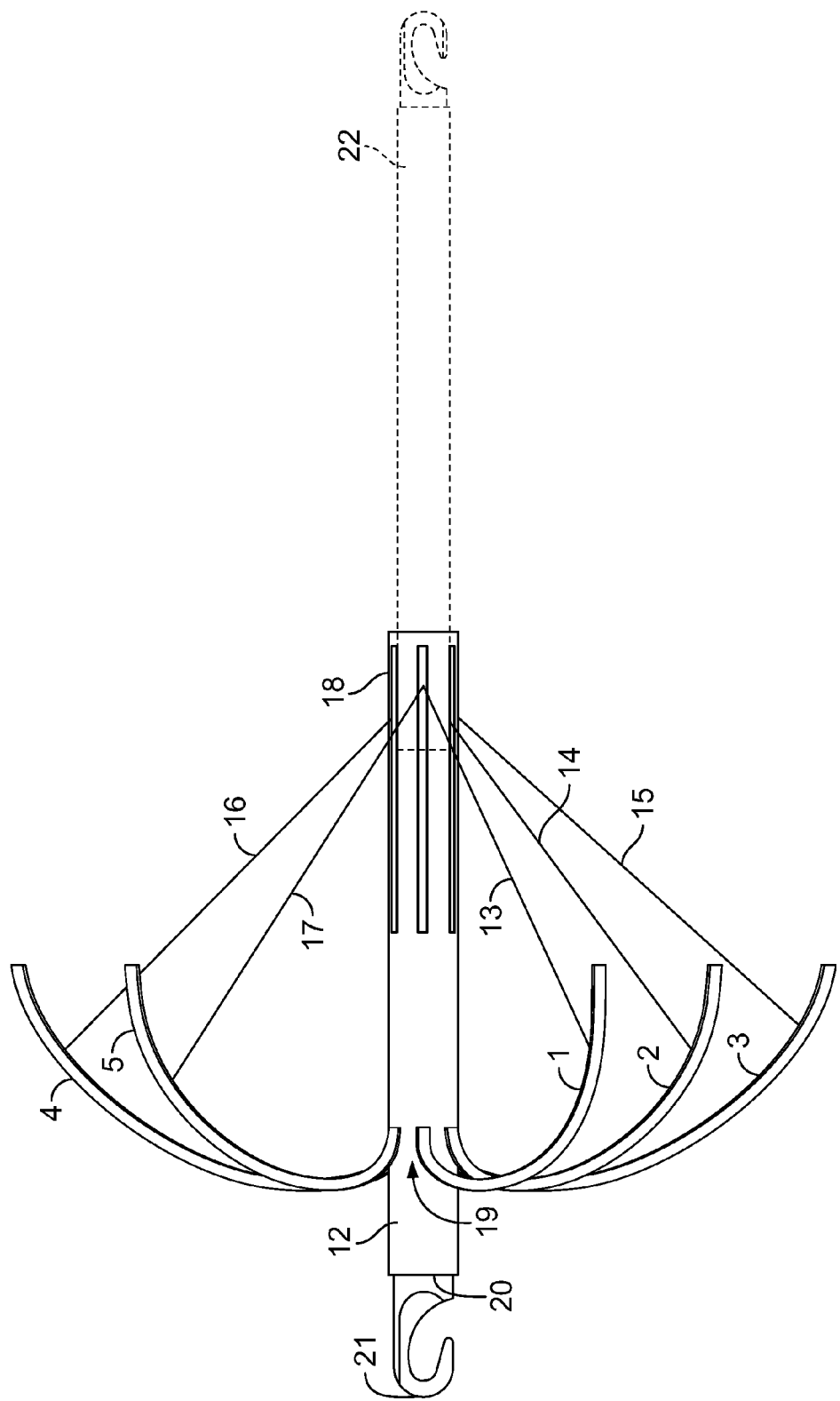

FIG. 2a shows a perspective view of the first tube of the filter in FIG. 1. The first tube 12 contains a plurality of a first set of expandable legs 1, 2, 3, 4, and 5, and a plurality of a first set of connectors 13, 14, 15, 16, 17 and a plurality of a first set of slots 18. The slots 18 are parallel to the cylindrical axis of the first tube 12. The first set of expandable legs 1, 2, 3, 4 and 5 are attached or secured at a point 19 which is proximal to end 20 on the first tube 12. Each slot of the first set 18 on the first tube 12 is positioned at a radial position allowing for deployment of the first set of connectors 13, 14, 15, 16, 17. There is one notch 21 at the end 20 of the first tube proximal to the first set of expandable legs.

The first set of slots 18 may start at a position from the ends 20 of the first tube from about 2 mm to about 15 mm, from about 4 mm to about 8 mm or from about 5 mm to about 7 mm or about 6 mm. Each slot may range in length from about 4 mm to about 35 mm, from about 10 mm to about 25 mm, from about 15 mm to about 20 mm, or about 17 mm.

Figure 2B:
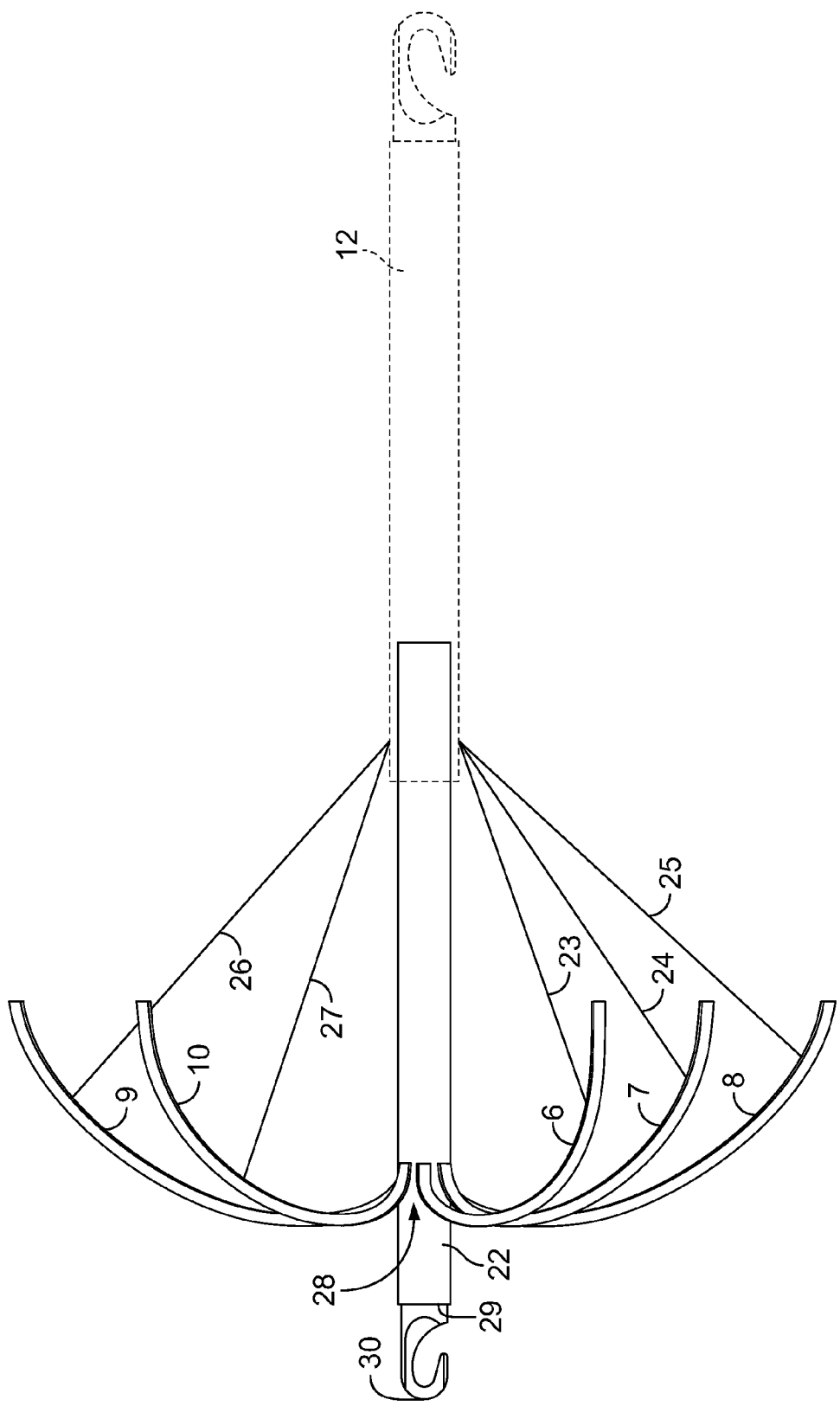

FIG. 2b shows a perspective view of the second tube of the filter in FIG. 1. The second tube 22 comprises a second set of expandable legs 6, 7, 8, 9 and 10 and a second set of connectors 23, 24, 25, 26, 27. The second set of expandable legs 6, 7, 8, 9, 10 is attached to the point 28 of the second tube proximal to the end 29. There is one notch 30 at the end 29 of the second tube 22.

The length from point 19 to 20 and the length from point 28 to 29 range from about 2 mm to about 10 mm, from 3 mm to about 8 mm, from about 4 mm to about 7 mm or about 6 mm. The length from point 19 to 20 and the length from point 28 to 29 may be the same or be different.

The first tube and the second tube may have a length of about 20 mm to about 70 mm, from about 30 mm to about 60 mm, from about 35 mm to about 50 mm or about 40 mm. The internal diameter of the first tube may range from about 1.0 mm to about 1.6 mm, from about 1.2 mm to about 1.6 mm, from about 1.4 mm to about 1.5 mm or about 1.45 mm. The thickness of the first tube may range from about 0.4 mm to about 0.8 mm, from about 0.5 mm to about 0.7 mm, from about 0.5 mm to about 0.6 mm, or about 0.58 mm. The thickness of the first tube may be constant or may vary from one end to the other end. Either end of the first tube may be straight or beveled. The external diameter of the second tube is less than the internal diameter of the first tube. The external diameter of the second tube may vary from about 0.5 mm to about 1.5 mm, from about 0.8 mm to about 1.5 mm, from about 1.2 mm to about 1.5 mm, from 1.4 mm to about 1.5 mm or about 1.45 mm, provided that the external diameter of the second is less than the internal diameter of the first tube. The thickness of the second tube may range from about 0.3 mm to about 0.6 mm, from about 0.4 mm to about 0.5 mm or from about 0.4 mm to about 0.45 mm. The filter of the present invention is assembled by inserting the second tube 22 into the first tube 12. All the expandable legs on the second tube are straight, i.e., not expanded, during insertion.

In this embodiment, as is apparent from FIG. 1c, the second set of expandable legs, 6, 7, 8, 9 and 10 are positioned at the same radial points along the circumference of the first and second tube after insertion of the second tube into the first tube as compared with the first set of expandable legs, 1, 2, 3, 4 and 5. The free ends of the first set of expandable legs 1, 2, 3, 4 and 5 are in a direction opposite to the free ends of the second set of expandable legs 6, 7, 8, 9 and 10. Each of the free ends of the first and the second set of expandable legs 1, 2, 3, 4, 5, and 6, 7, 8, 9, 10 may have a barb 32 (FIG. 1b).

The first and second sets of expandable legs may have a length of about 10 mm to about 30 mm, from about 15 mm to about 25 mm or about 20 mm. The expandable legs of each set may have a width ranging from 0.05 mm to about 1.5 mm, from about 0.1 mm to about 1.0 mm, from about 0.3 mm to about 0.8 mm or about 0.35 mm. The width of the first and second sets of expandable legs may be constant or vary. For example, in one embodiment, the width of the first and second set of expandable legs may taper or narrow from the point where it is secured to the barbed end. The expanded diameter of the first and second set of expandable legs may range from 10 mm to about 45 mm, from about 15 mm to about 40 mm, from about 20 mm to about 36 mm or about 30 mm.

The first and second sets of connectors may have a length ranging from about 5 mm to 40 mm, from about 10 mm to about 30 mm, or from about 15 mm to about 25 mm. The length from point 31 to 20 and from point 23 to 29 may be from 20 mm to about 70 mm, from about 30 mm to about 60 mm, from about 35 mm to about 50 mm or about 40 mm.

Figure 3:
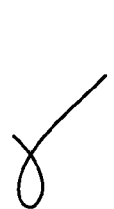
FIG. 3 shows various embodiments of the barb design.
Figure 3:
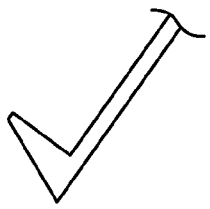
Figure 3:
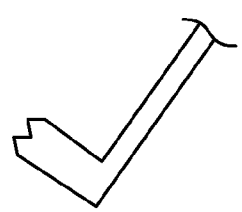
Figure 3:
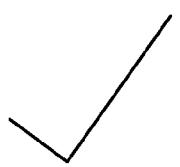
Figure 3:
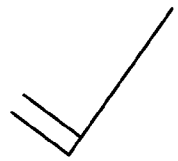
Figure 3:
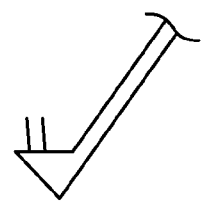
Figure 3:
Figure 3:
Figure 3:
Figure 3:

Each of the free ends of the first and the second sets of expandable legs may have at least one barb. The barbs may assume various designs and angles. For example, the angle between the barb and the free end of the leg where the barb is attached to may range from about 10 degrees to about 200 degrees, from about 40 degrees to about 200 degrees, from about 60 degrees to about 190 degrees, from about 90 degrees to about 180 degrees or from about 95 to about 105 degrees relative to a straight line set when the first set of expandable legs is in an undeployed position. The barbs can be any desired shape or configuration the examples of which are shown in FIG. 3. In one embodiment, the barb is made of a wire that is bent into desired shape. In another embodiment, the barb is made of a round tube or pin that is bent into desired shape. In a further embodiment, the barb has a convex shape allowing it to bend on itself when the filter is deployed. In certain embodiments, the barb curls on itself so that when the filter is retrieved, the barb pulls away from the vessel wall with minimum damage to the vessel. The shape, configuration, dimension, angle and penetration depth of the barbs may vary between legs and may be present on some or all of the first, second and/or the third set of expandable legs to ensure proper placement of the filter and smooth removal of the filter. In one embodiment, the angle of the barbs is set such that the barbs will not penetrate into the vessel wall until the internal vessel dimension of at least about 18 mm has been encountered by the filter. It will be appreciated that one of ordinary skill in the art could select both the shape of the barb and the angle by routine experimentation and that the shape of the cage formed by the first and second set of expandable legs can be constrained to meet this requirement.

Figure 4A:
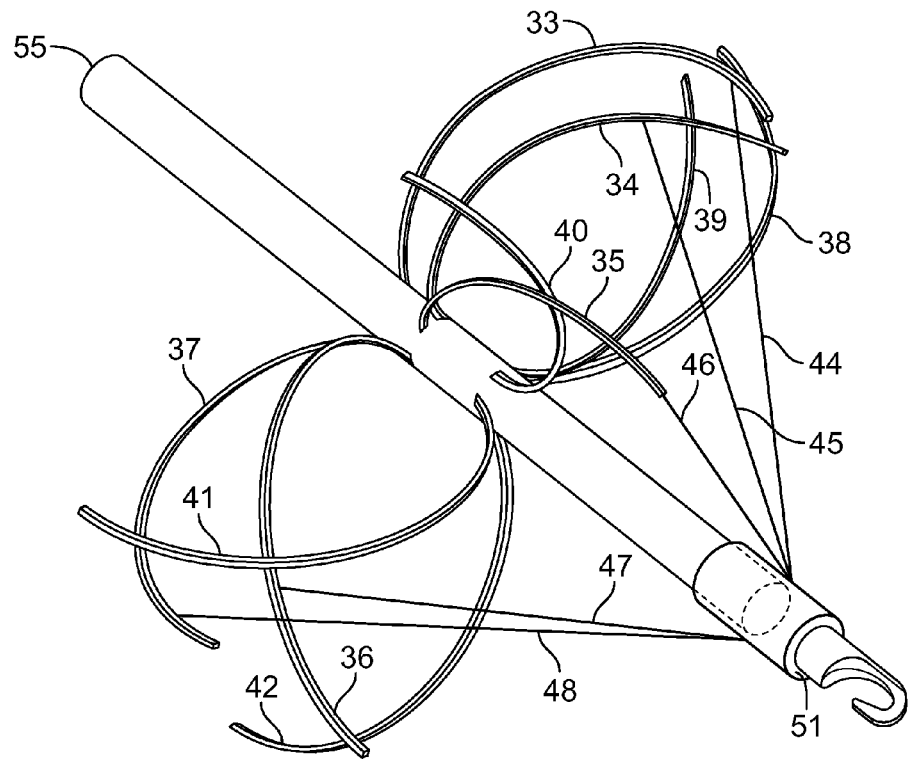
FIG. 4a shows a perspective view of the second embodiment of the filter where there is a plurality of connectors attached to one set of the expandable legs.
Figure 4B:
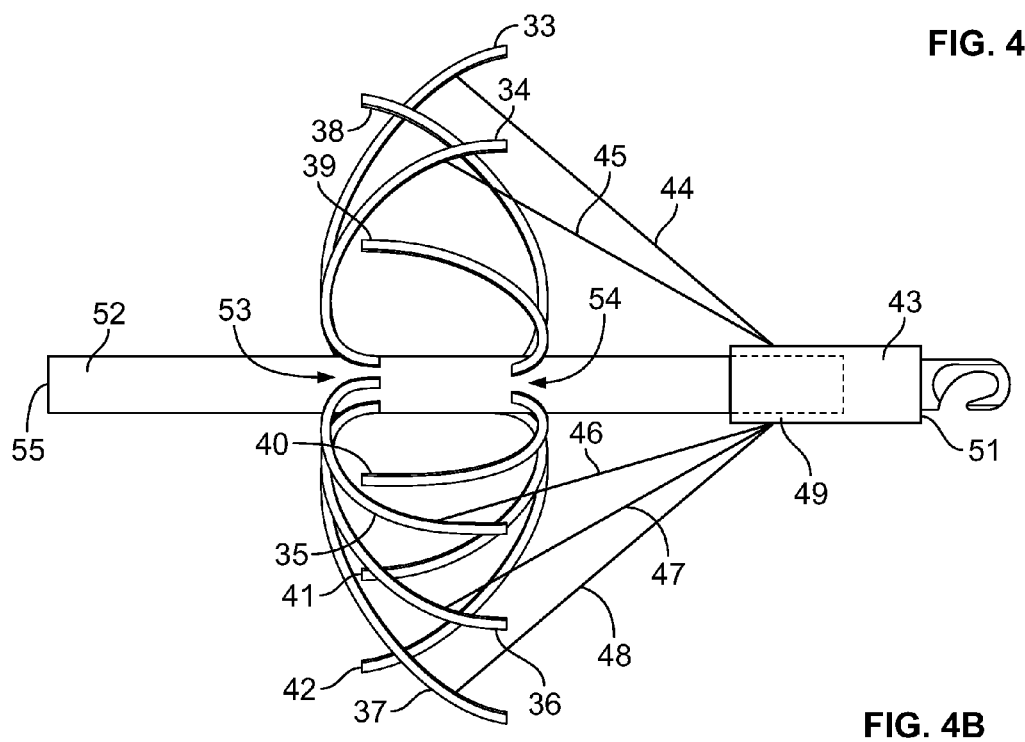

A second embodiment of the present filter is shown in FIGS. 4a, b and c. The filter comprises a first tube and a second tube that is inserted into the first tube. The external diameter of the second tube is smaller than the internal diameter of the first tube. The filter comprises a first set of expandable legs, 33, 34, 35, 36, 37 and a second set of expandable legs 38, 39, 40, 41, 42. FIG. 5a shows a perspective view of the first tube of the filter in FIG. 4. The first tube 43 contains a plurality of a first set of connectors 44, 45, 46, 47, 48. The first set of connectors 44, 45, 46, 47, 48 are attached at a point 49 on the first tube 43. There is a notch 50 at the end 51 of the first tube 43. FIG. 5b shows a perspective view of the second tube 52. The second tube contains a first set of expandable legs 33, 34, 35, 36, 37, a second set of expandable legs 38, 39, 40, 41, 42. The first set of expandable legs 33, 34, 35, 36, 37 are secured at a point 53 on the second tube 52. The second set of expandable legs 38, 39, 40, 41, 42 are attached to a point 54 on the second tube 52. Each expandable leg of the first set 33, 34, 35, 36, 37 is attached to a connector of the first set 44, 45, 46, 47, 48.

The length of the first tube ranges from 3 mm to about 20 mm, from about 4 mm to about 15 mm or from about 5 mm to about 10 mm or about 8 mm. The length from point 49 to end 51 ranges from about 2 mm to about 15 mm, from about 4 mm to about 8 mm or from about 5 mm to about 7 mm or about 6 mm. The second tube may have a length of about 20 mm to about 70 mm, from about 30 mm to about 60 mm, from about 35 mm to about 50 mm or about 40 mm. The length from point 53 to end 55 may be greater, equal or less than the length from point 54 to end 55. The external diameter of the second tube is less than the internal diameter of the first tube. The filter of the present invention is assembled by inserting the second tube 52 into the first tube 43. All the expandable legs on the second tube are straight, i.e., not expanded, during insertion.

Figure 4C:
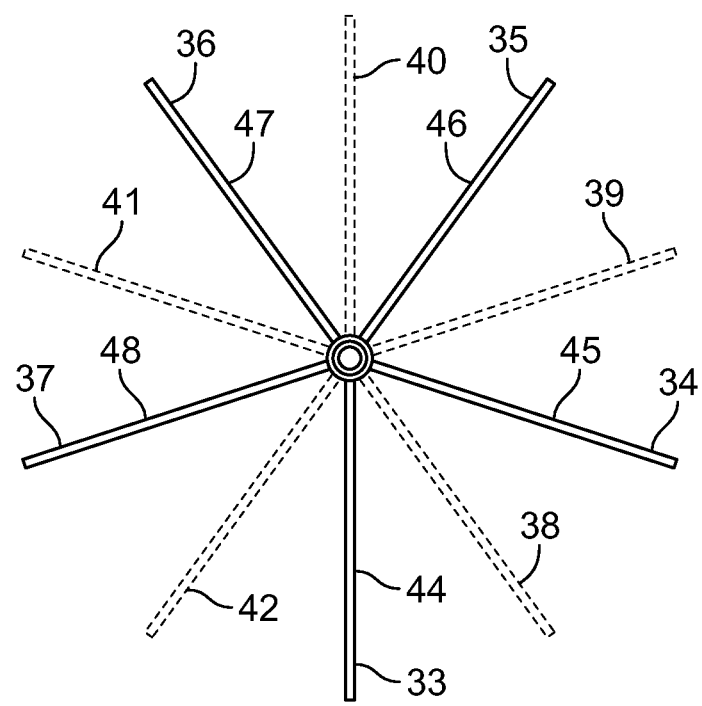
FIG. 4c shows a perspective view of the filter in FIG. 4a as it would appear looking from 51 to 55.
Figure 5A:
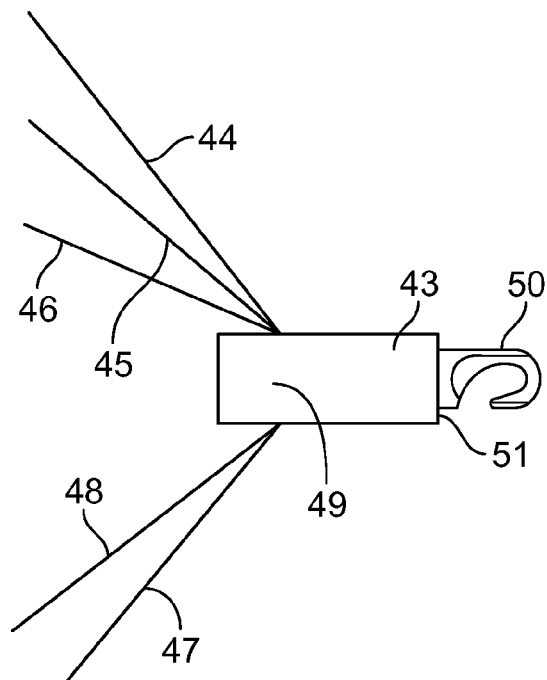
Figure 5B:
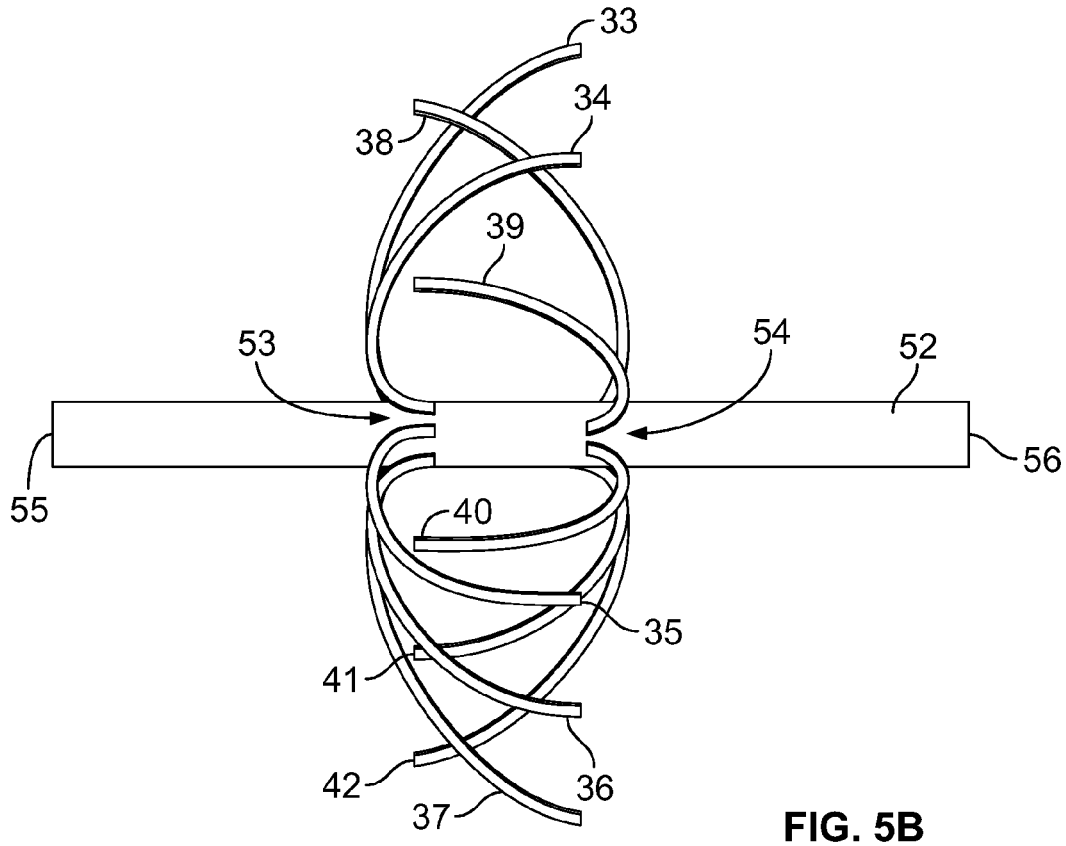

In this embodiment, as is apparent from FIG. 4c, the radial positions of the second set of expandable legs, 38, 39, 40, 41, 42 are off-set from the radial positions of the first set of expandable legs 33, 34, 35, 36, 37 along the circumference of the second tube. The free ends of the first set of expandable legs 33, 34, 35, 36, 37 are in a direction opposite to the free ends of the second set of expandable legs 38, 39, 40, 41, 42. Each set of expandable legs forms a semi-sphere shape after deployment. The two semi-sphere shapes may be overlapped.

Figure 6A:
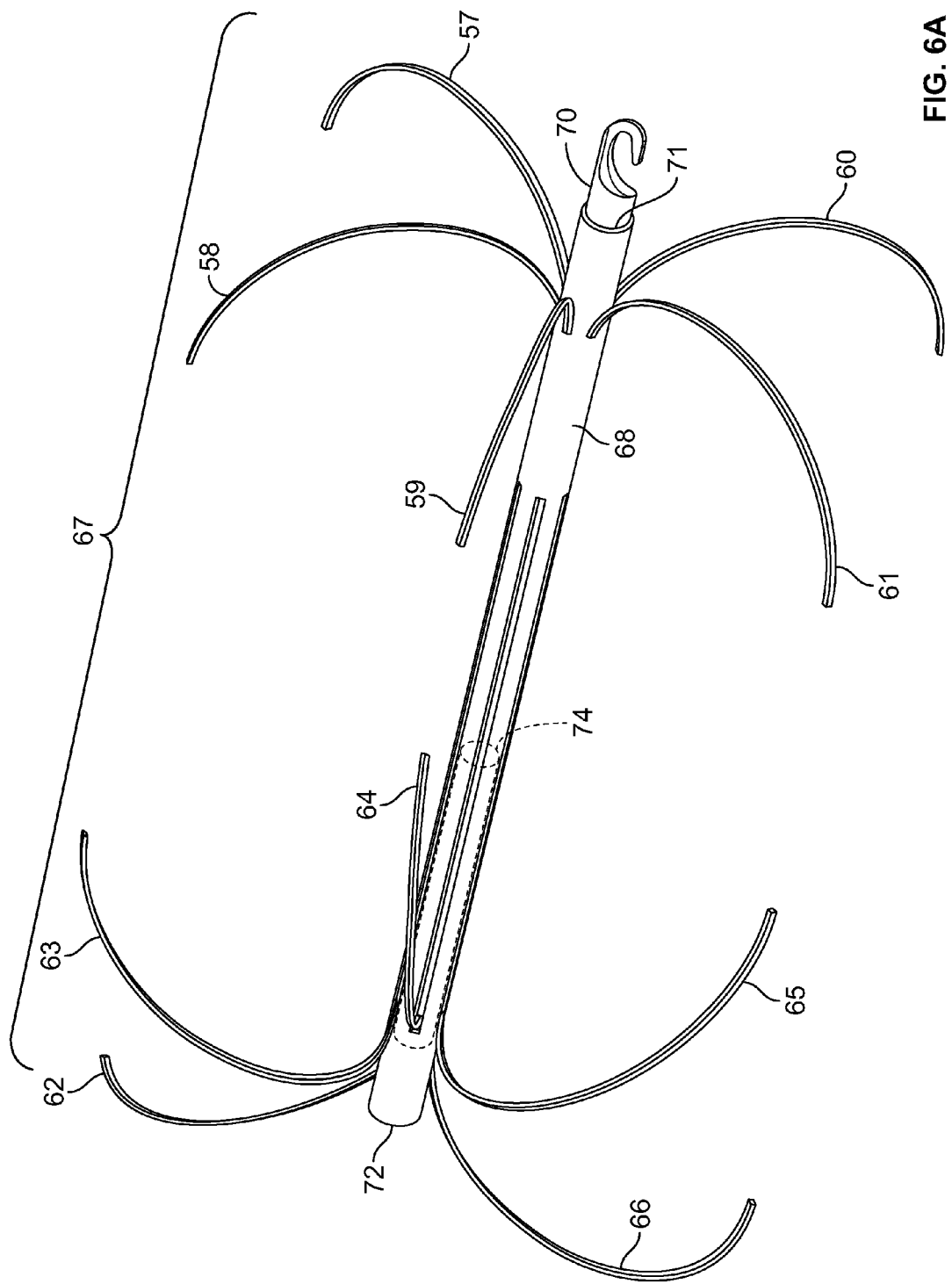
FIG. 6a shows a perspective view of one embodiment of the filter where the second set of expandable legs are attached to a tube or pin inserted into the first tube.
Figure 6B:
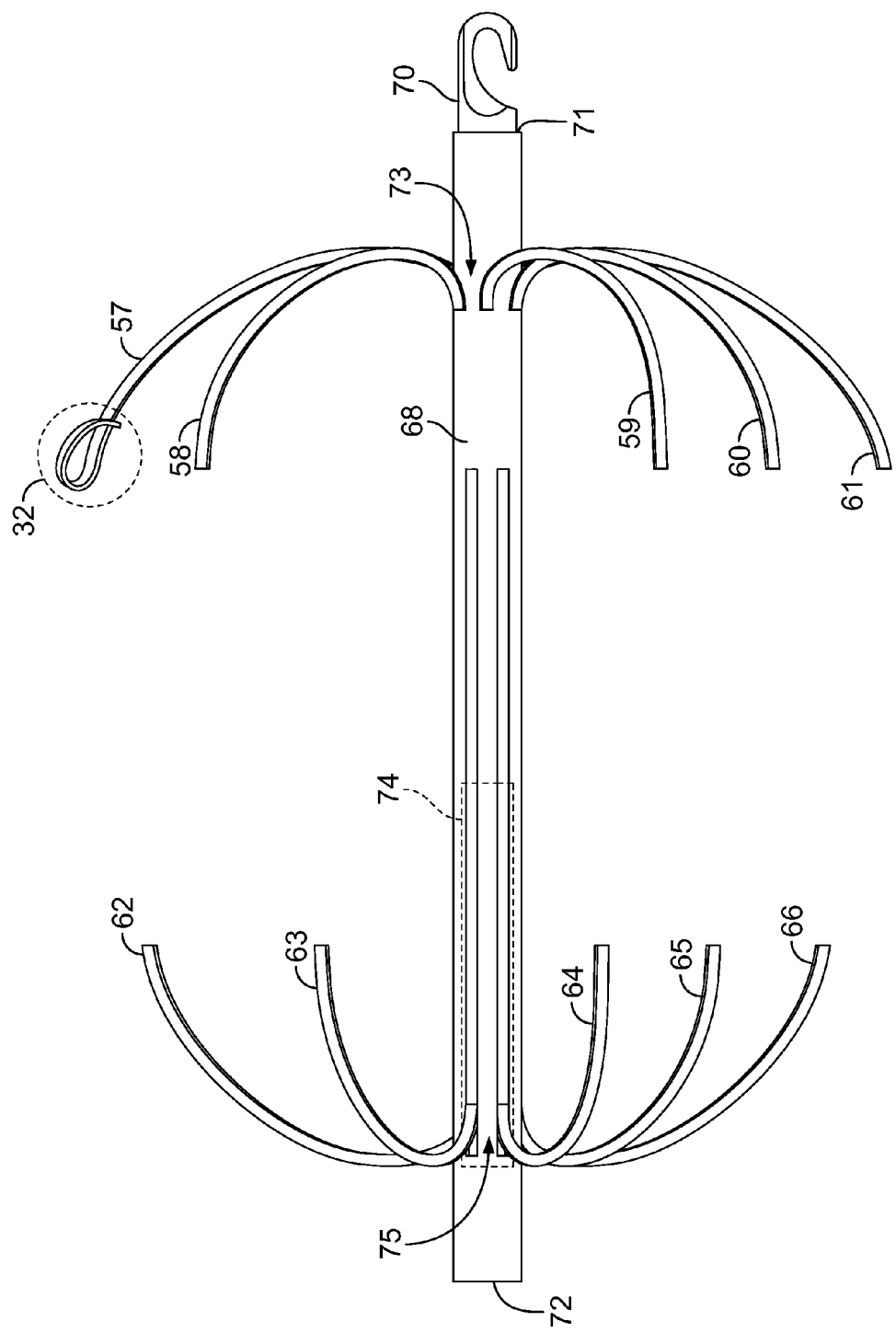

A third embodiment of the present filter is shown in FIG. 6a, b, c. The filter comprises a first tube and a second tube that is inserted into the first tube. The external diameter of the second tube is smaller than the internal diameter of the first tube. The filter has two sets of five expandable legs, the first expandable set, 57, 58, 59, 60, 61, and the second expandable set, 62, 63, 64, 65, 66. These expandable legs form a cage 67. The cage 67 may take the shape of a ball or sphere when deployed. In one embodiment, the first set of expandable legs, 57, 58, 59, 60, 61 are positioned at the same radial points along the circumference of the first tube as compared with the second set of expandable legs, 62, 63, 64, 65, 66. The free ends of the first set of expandable legs 57, 58, 59, 60, 61 are in a direction opposite to the free ends of the second set of expandable legs 62, 63, 64, 65, 66. Each of the free ends of the first and the second set of expandable legs 57, 58, 59, 60, 61, and 62, 63, 64, 65, 66 may have a barb 32 (FIG. 6b). In another embodiment, the first set of expandable legs, 57, 58, 59, 60, 61 are positioned at different radial points along the circumference of the first tube as compared with the second set of expandable legs, 62, 63, 64, 65, 66. The semisphere formed by the first set of expandable legs 57, 58, 59, 60, 61 may overlap with the semisphere formed by the second set of expandable legs 62, 63, 64, 65, 66 (FIG. 6c).

Figure 6C:
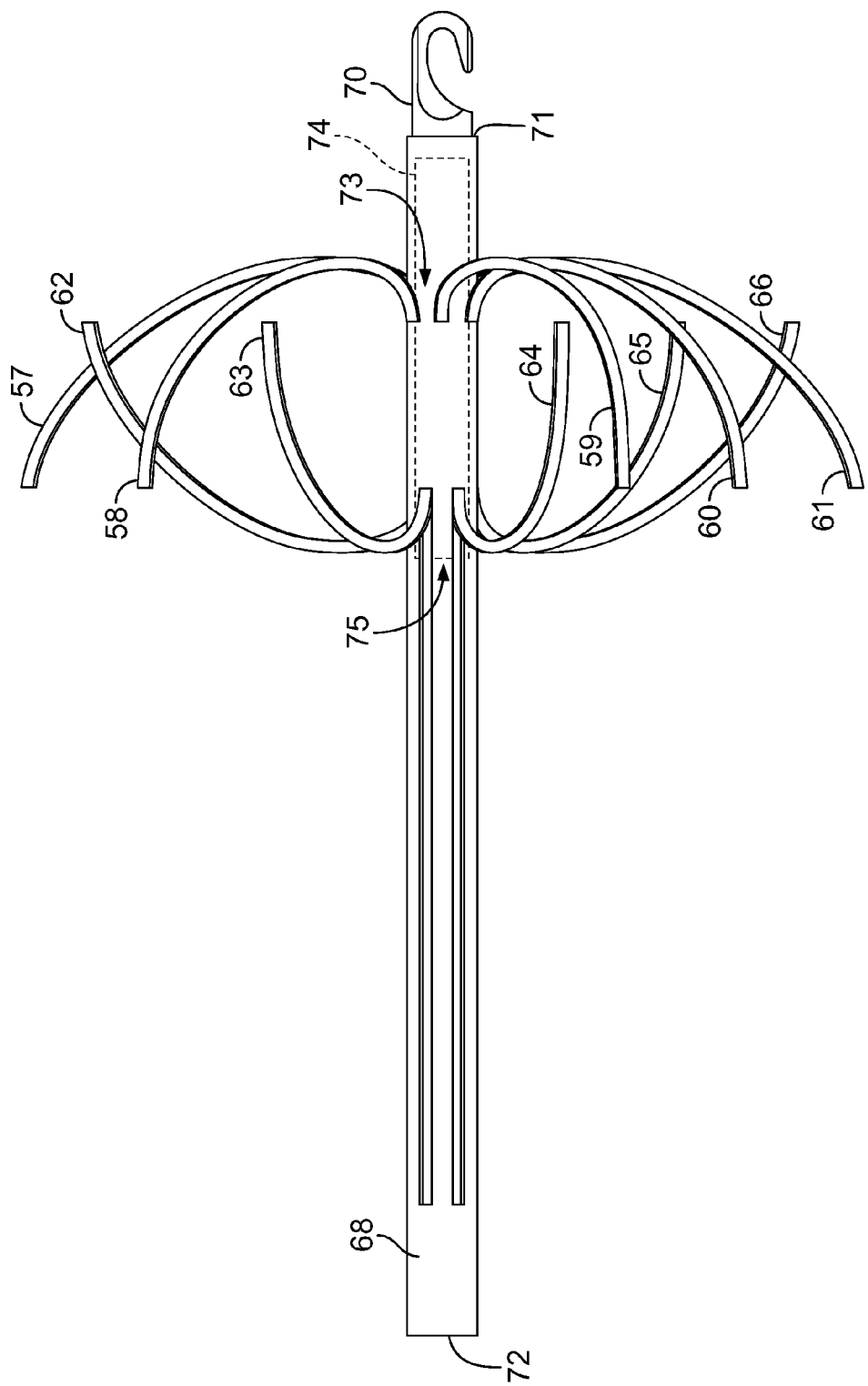
FIG. 6c shows another configuration of the filter in FIG. 6a when the two semi-sphere formed by the two sets of legs overlap.
Figure 7A:
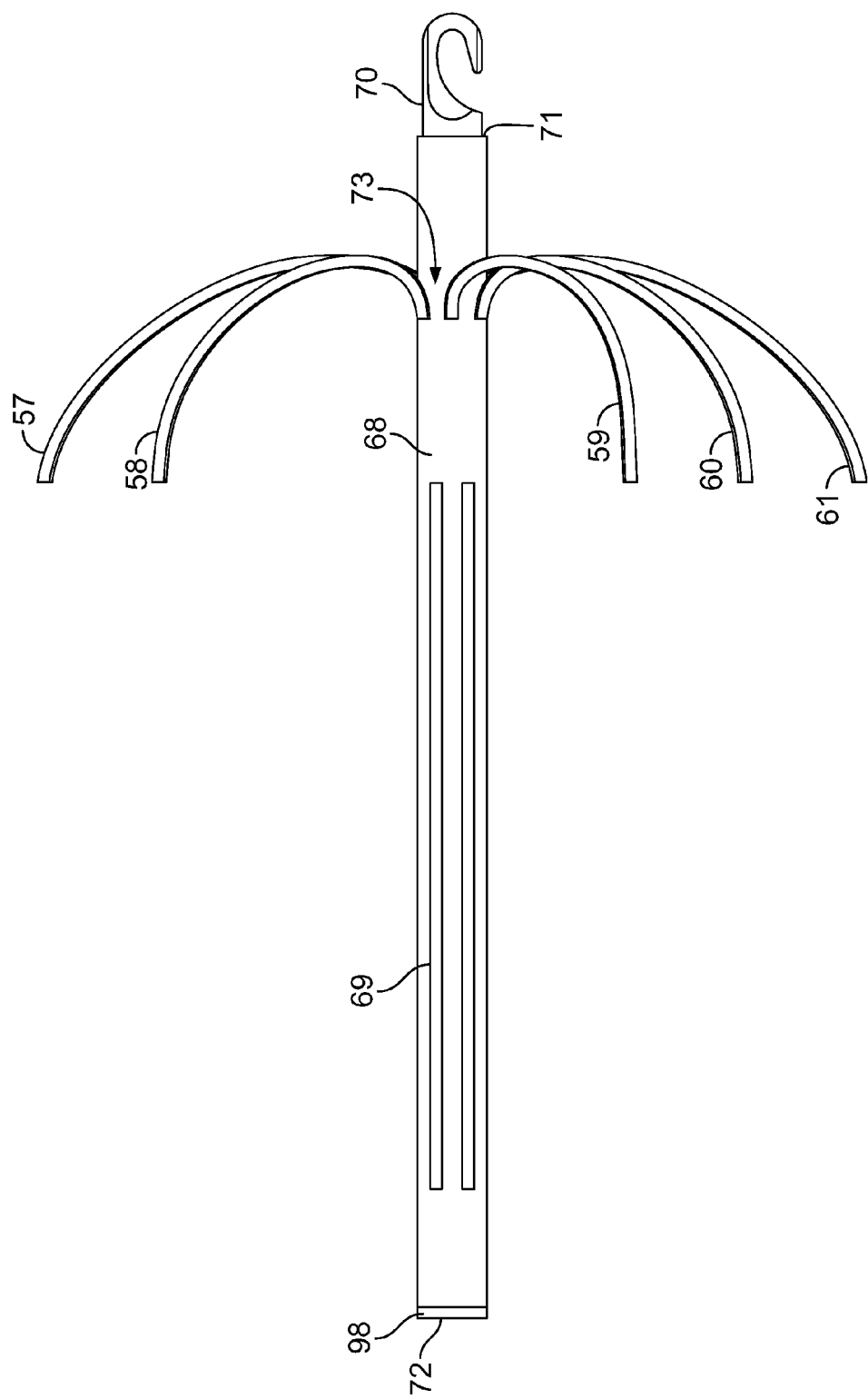
Figure 7B:
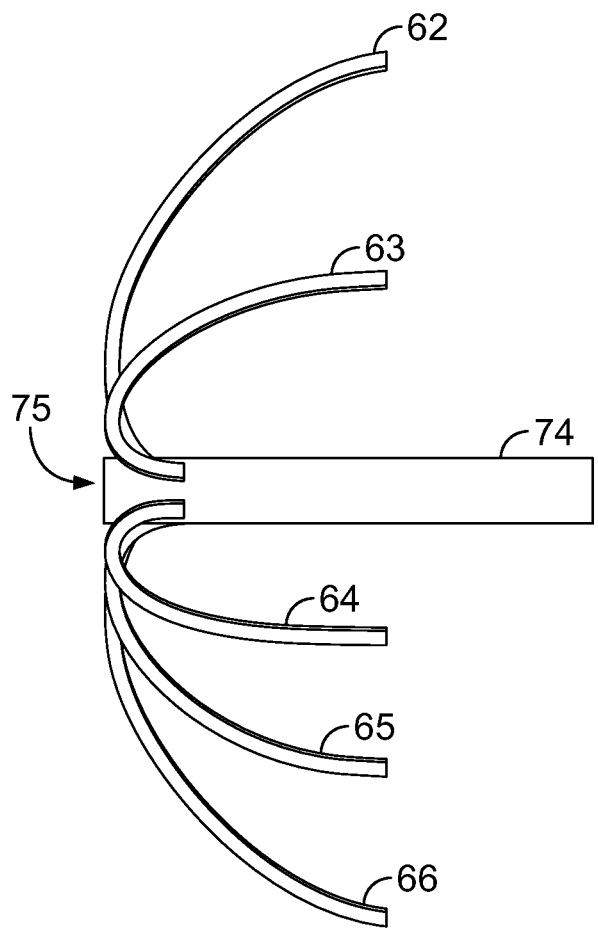

FIG. 7a shows a perspective view of the first tube of the filter in FIG. 6. The first tube 68 contains a plurality of a first set of slots 69 which are parallel to the long or cylindrical axis of the first tube, and a plurality of a first set of expandable legs 57, 58, 59, 60, 61. Each leg of the first set is secured to a point 73 which is proximal to end 71 of the first tube 68. There is one notch 70 at the end 71 and one cap 98 at the end 72 of the first tube 68. FIG. 7b shows perspective view of the second tube. The second tube 74 contains a plurality of a second set of expandable legs 62, 63, 64, 65, 66. Each slot of the first set 69 on the first tube 68 is positioned at a radial position allowing for deployment of the second set of expendable legs, 62, 63, 64, 65, 66 of the second tube 74. Each leg of the second set is secured at a point 75 on the second tube. The internal diameter of the first tube is greater than the external diameter of the second tube and the filter is formed by inserting the second tube into the first tube. The second tube 74 can be hollow with at least one cap at its end distal to point 75. The second tube 74 may alternatively be a pin. The first tube may have a length of about 35 mm to about 80 mm, from about 40 mm to about 70 mm, from about 45 mm to about 60 mm or about 50 mm. The second tube may have a length of about 10 mm to about 60 mm, from about 15 mm to about 50 mm, from about 20 mm to about 45 mm or about 25 mm. The length from point 73 to point 75 after deployment ranges from about 0 mm to about 75 mm, from about 10 mm to about 60 mm, from about 20 mm to about 50 mm or about 45 mm. FIG. 6c shows a perspective view of the filter when the length from point 73 to point 75 is small so that the two semi-spheres formed by the first and the second set of legs overlap.

Figure 8A:
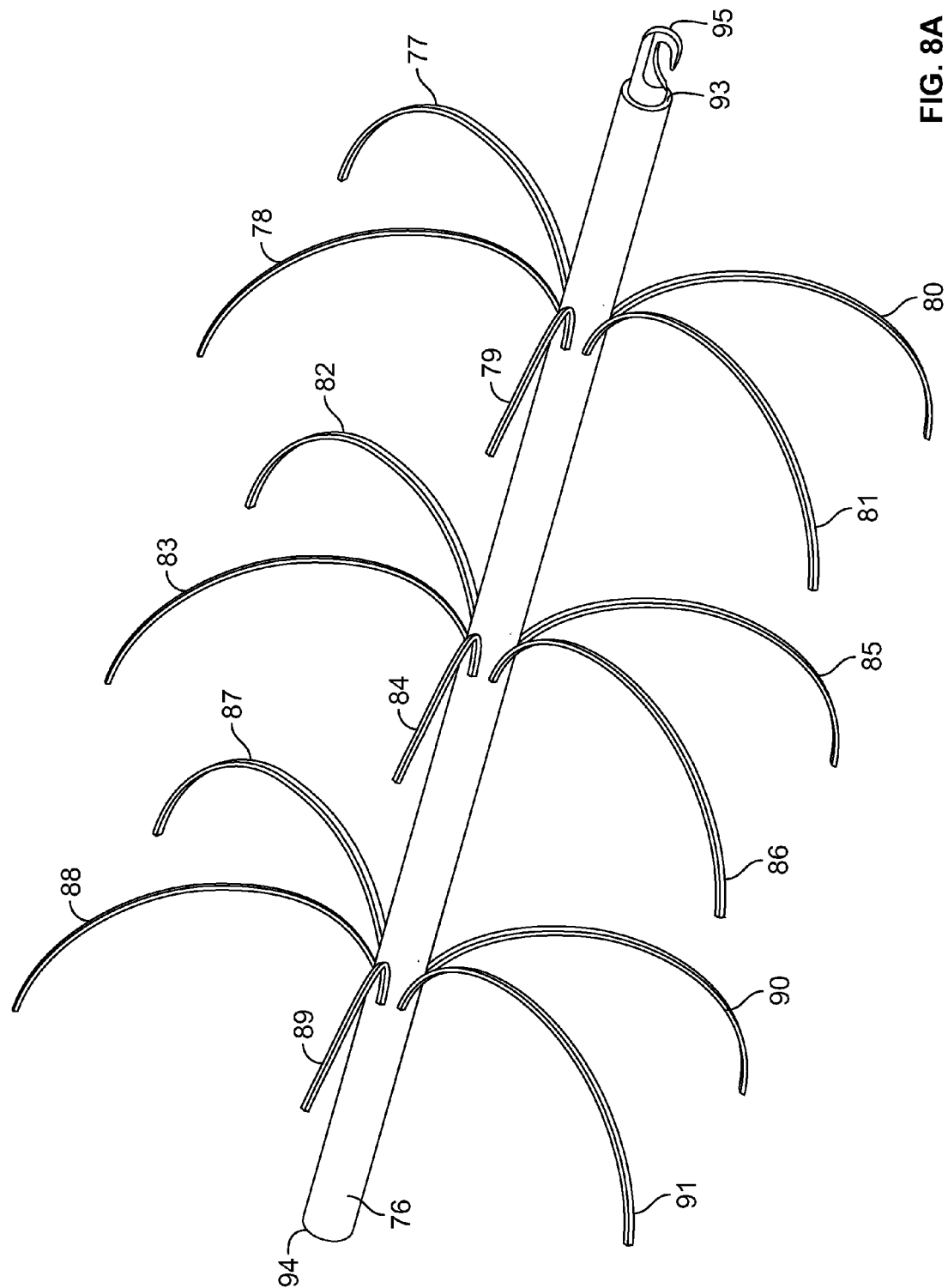
FIG. 8a shows a perspective view of one embodiment of the filter which is a tree shape formed by three sets of expandable legs.
Figure 8B:
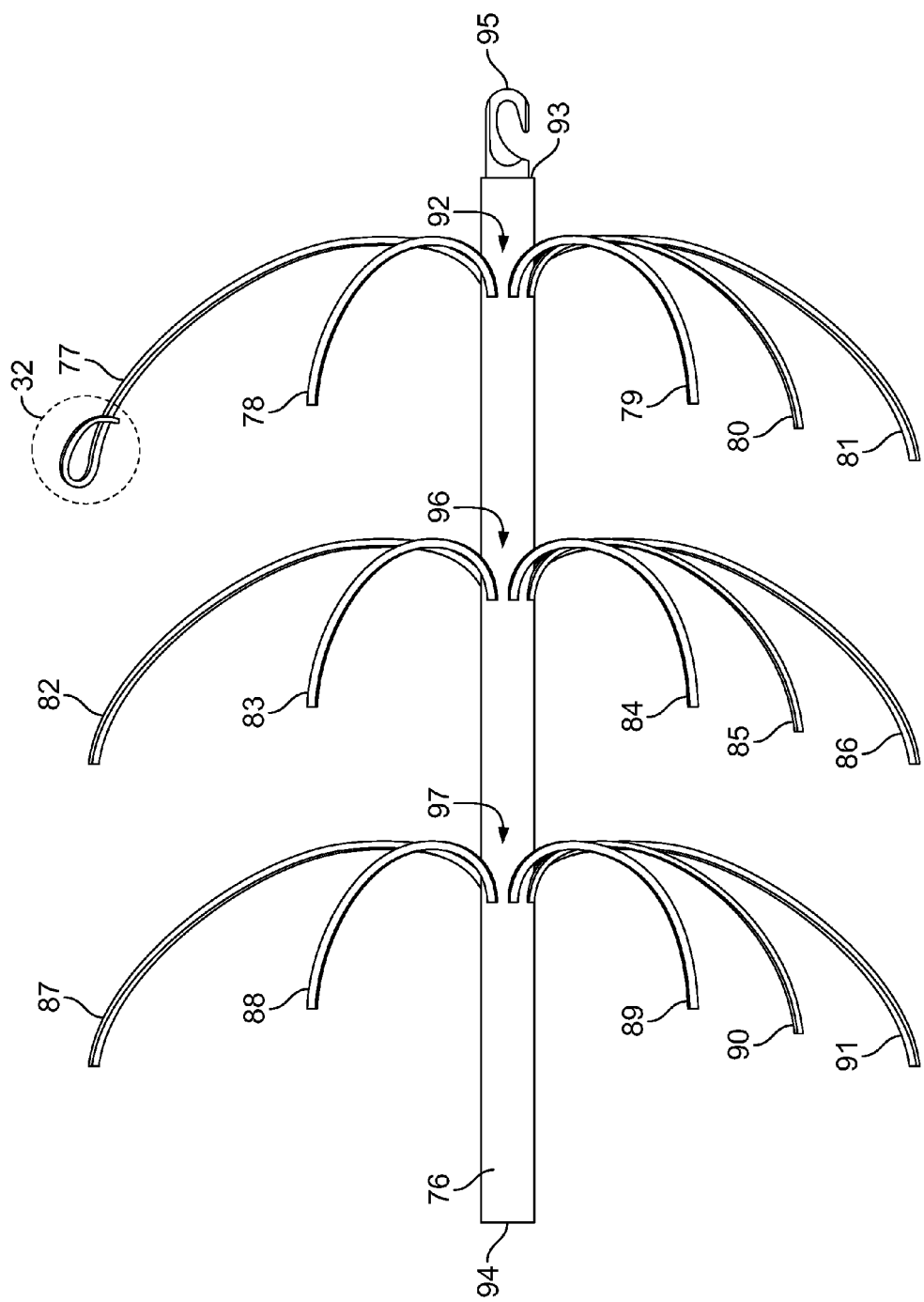
Figure 8C:
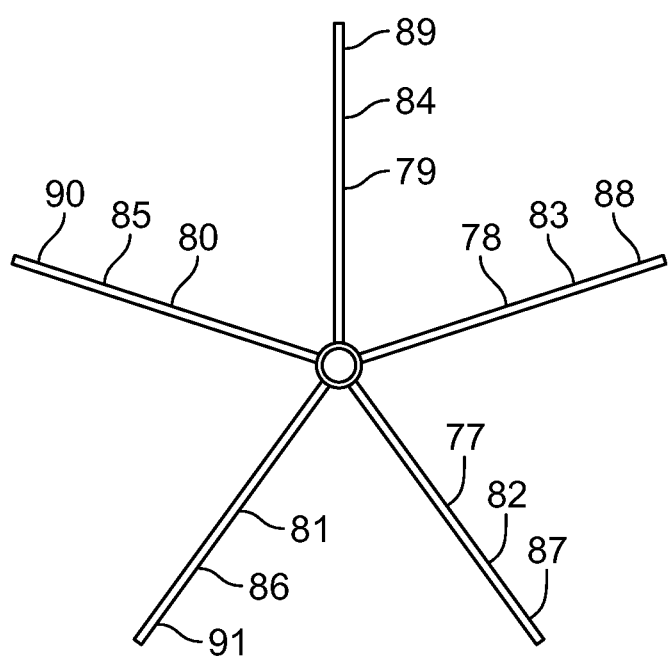
FIG. 8c shows a perspective view of the filter in FIG. 8a as it would appear looking from 93 to 94.

A forth embodiment of the present filter is shown in FIGS. 8a, b, and c. The filter is formed from a tube 76 with three sets of five expandable legs: the first expandable set, 77, 78, 79, 80, 81, the second expandable set, 82, 83, 84, 85, 86, and the third expandable set 87, 88, 89, 90, 91. The first set of expandable legs are secured at point 92 closest to the end 93 of the tube 76. The second set of expandable legs are secured at point 96 and the third set of expandable legs are secured at point 97 distal to the end 93 on the tube 76. Each of the expandable legs has a free end pointing to the end 94. These expandable legs form a tree shape when deployed. The length from point 92 to point 96 and the length from point 96 to point 97 may be from about 5 mm to about 20 mm, from about 10 mm to about 15 mm or about 10 mm. The length from point 92 to point 96 and the length from point 96 to point 97 may be the same or be different. In this embodiment, as is apparent from FIG. 8c, the first set of expandable legs, 77, 78, 79, 80, 81 are positioned at the same radial points along the circumference of tube 76 as compared with the second set of expandable legs, 82, 83, 84, 85, 86 and the third set of expandable legs 87, 88, 89, 90, 91. Each of the free end of the first, second and third set of expandable legs may have a barb 32 (FIG. 8b).

There is one notch 95 at the end 93 of the tube 76. The tube 76 may have a length of about 35 mm to about 80 mm, from about 40 mm to about 70 mm, from about 45 mm to about 60 mm or about 50 mm. The internal diameter of the tube 76 may range from about 1.0 mm to about 1.6 mm, from about 1.2 mm to about 1.6 mm, from about 1.4 mm to about 1.5 mm or about 1.45 mm. The thickness of the tube 76 may range from about 0.4 mm to about 0.8 mm, from about 0.5 mm to about 0.7 mm, from about 0.5 mm to about 0.6 mm, or about 0.58 mm. The thickness of the tube 76 may be constant or may vary from one end to the other end. Either end of the tube 76 may be straight or beveled.

Figure 9A:
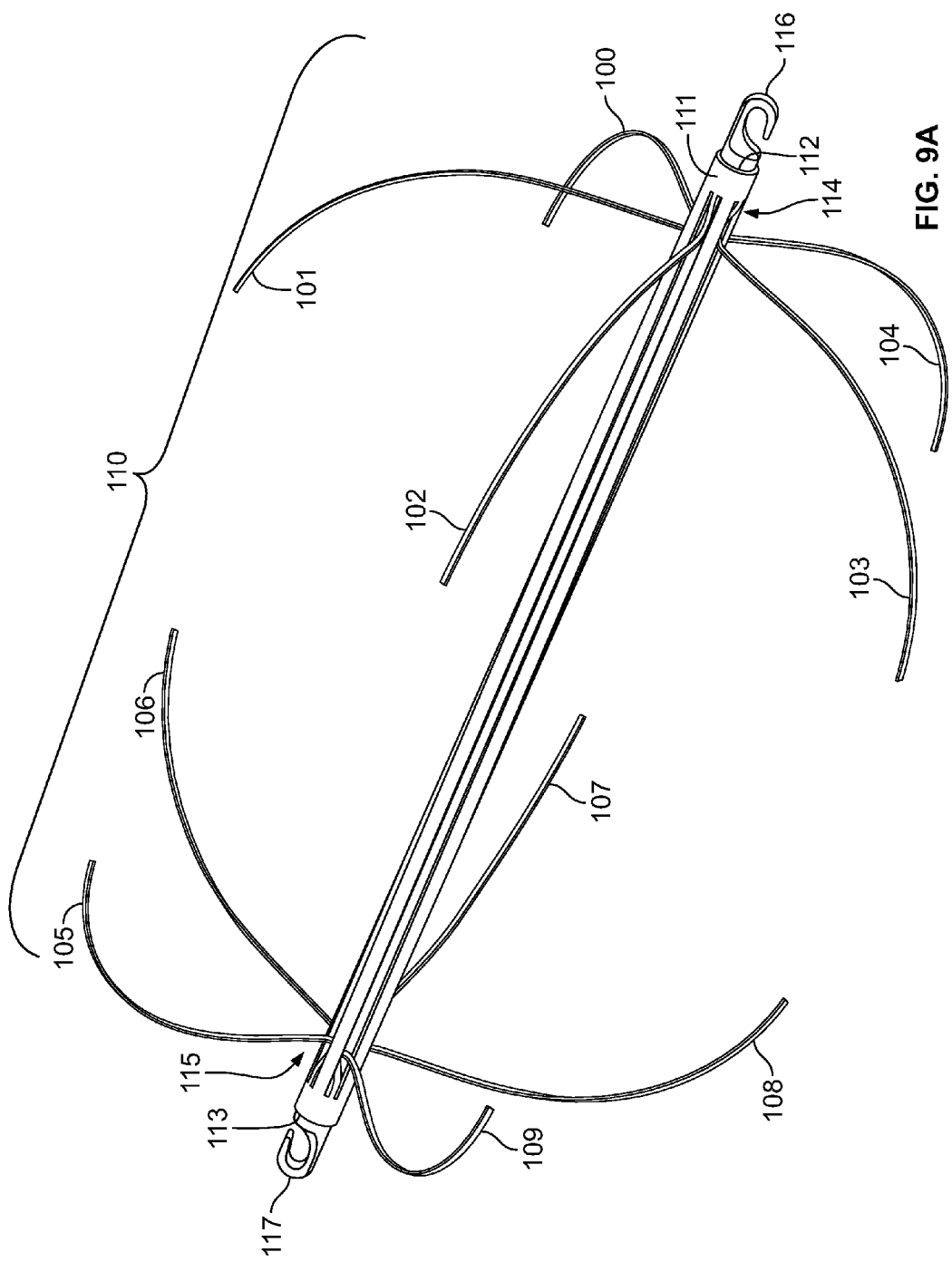
FIG. 9a shows a perspective view of one embodiment of the filter where the filter is formed by two sets of expandable legs on a single tube.
Figure 9C:
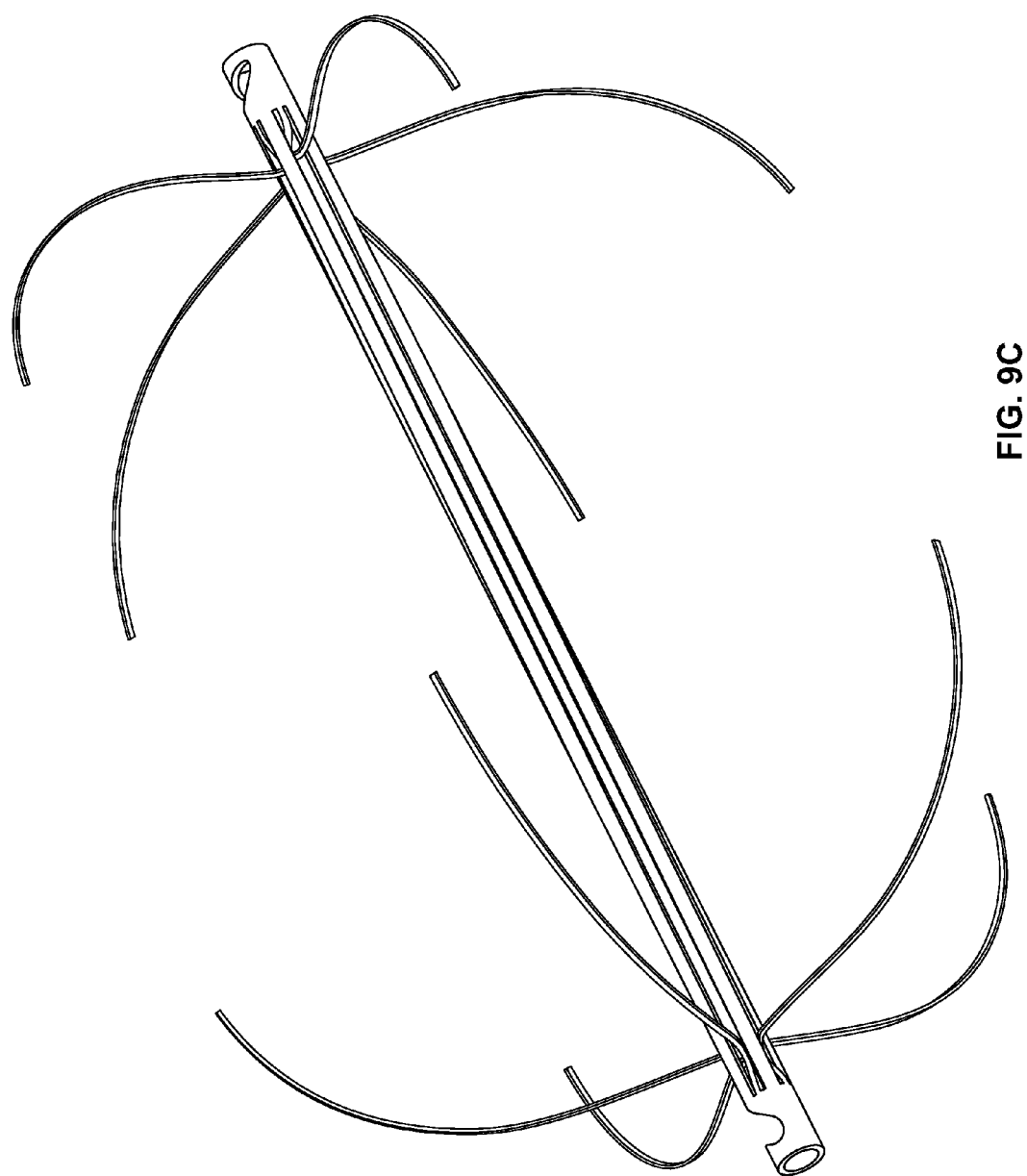
FIG. 9c shows another perspective view of the filter where the filter is formed by two sets of expandable legs on a single tube.

A fifth embodiment of the present filter is shown in FIG. 9a, b. The filter is formed from a single tube with two sets of five expandable legs. The first set 100, 101, 102, 103, 104 and the second set 105, 106, 107, 108, 109. Each leg of the first and second sets is bent first inward 301 at its end near 112 or 113, then outward 302, to allow for easy retrieval of the filter. These expandable legs form a cage 110. Each leg of the first set has an end secured at point 114 closest to end 112 of the tube 111 and a free end. Each leg of the second set has an end secured at point 115 closest to end 113 of the tube 111 and a free end. The free ends of the first set of expandable legs 100, 101, 102, 103, 104 are in a direction opposite to the free ends of the second set of expandable legs 105, 106, 107, 108, 109. The free ends of the first and second set of expandable legs may have a barb 32. Each leg of the first and second sets is bent inward at its end near 114 or 115 to allow for easy retrieval of the filter. There is one notch 116 at end 112 and one notch 117 at end 113 for retrieval of the filter. The radial position of the first set of expandable legs 100, 101, 102, 103, 104 are the same as the radial positions of the second set of expandable legs 105, 106, 107, 108, 109. The tube 111 may have a length of about 35 mm to about 80 mm, from about 40 mm to about 70 mm, from about 45 mm to about 60 mm or about 50 mm. The length from point 114 to 112 and the length from point 115 to 113 range from about 2 mm to about 10 mm, from 3 mm to about 8 mm, from about 4 mm to about 7 mm or about 6 mm. The length from point 114 to 112 and the length from point 115 to 113 may be the same or be different. The legs may have various shapes, including rectangular strips, wires, tubes, rods, threads, or any other desired structure. The legs may be straight, curved, tapered or have multiple angles. The shapes, configurations or dimensions of various portions of each leg may vary or be the same. The shapes, configurations, dimensions or angles of different legs of the filter may be different or may be the same. The legs may be notched, barbed, hooked or in any structure that anchors the legs in the vessel wall without interfering with the retrieval of the filter. FIG. 9c shows another perspective view of the filter where the filter is formed by two sets of expandable legs on a single tube. The filter has spiral cut pattern.

Figure 10A:
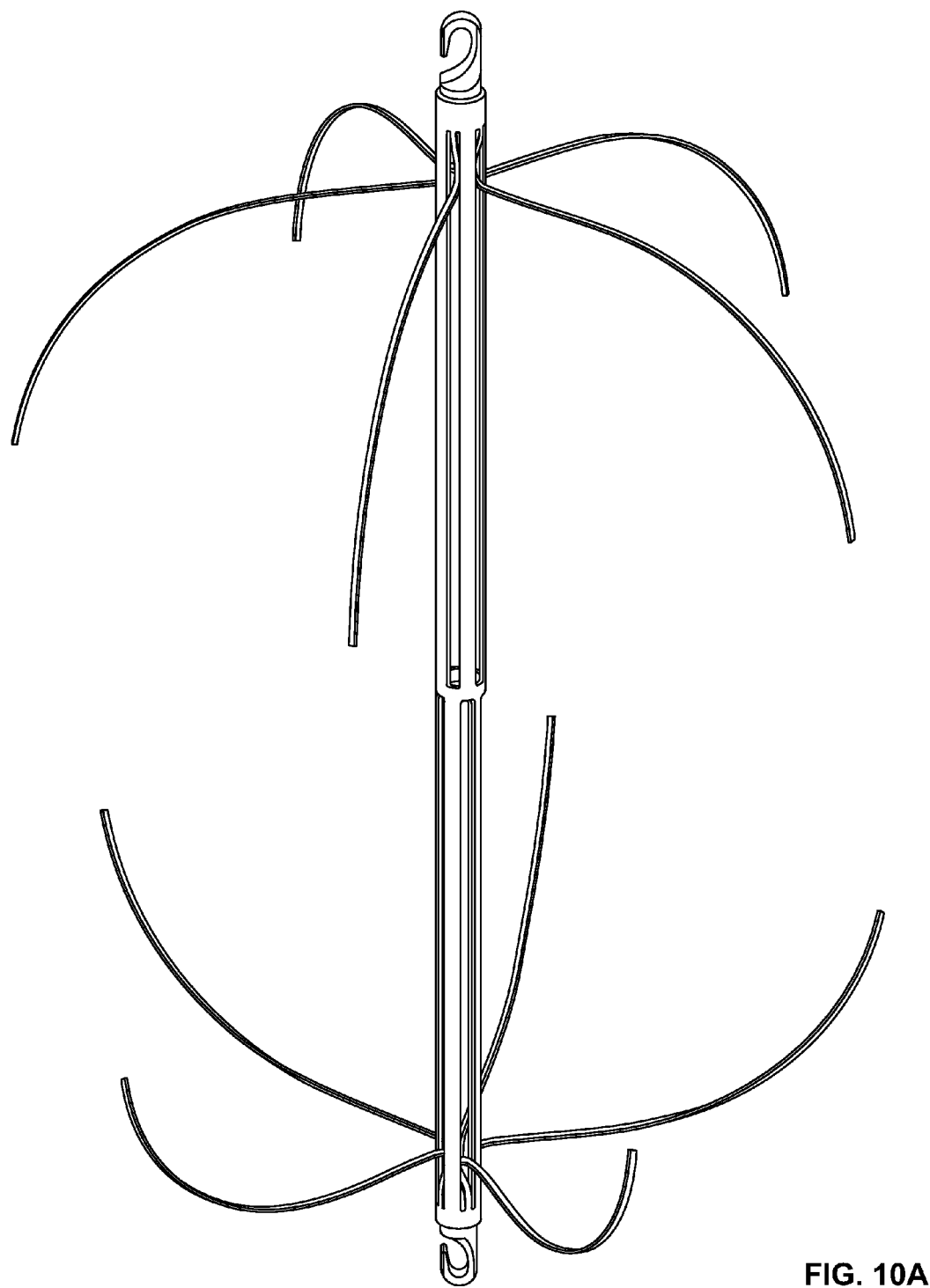
FIG. 10a shows a perspective view of another embodiment of the filter where the filter is formed by two sets of expandable legs on a single tube.
Figure 10B:
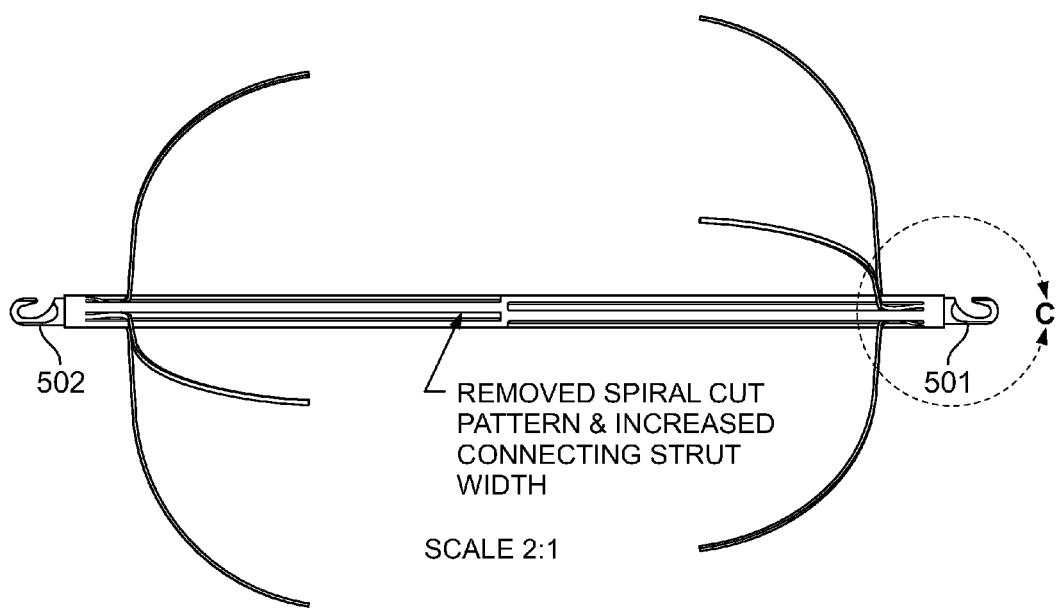
Figure 10C:
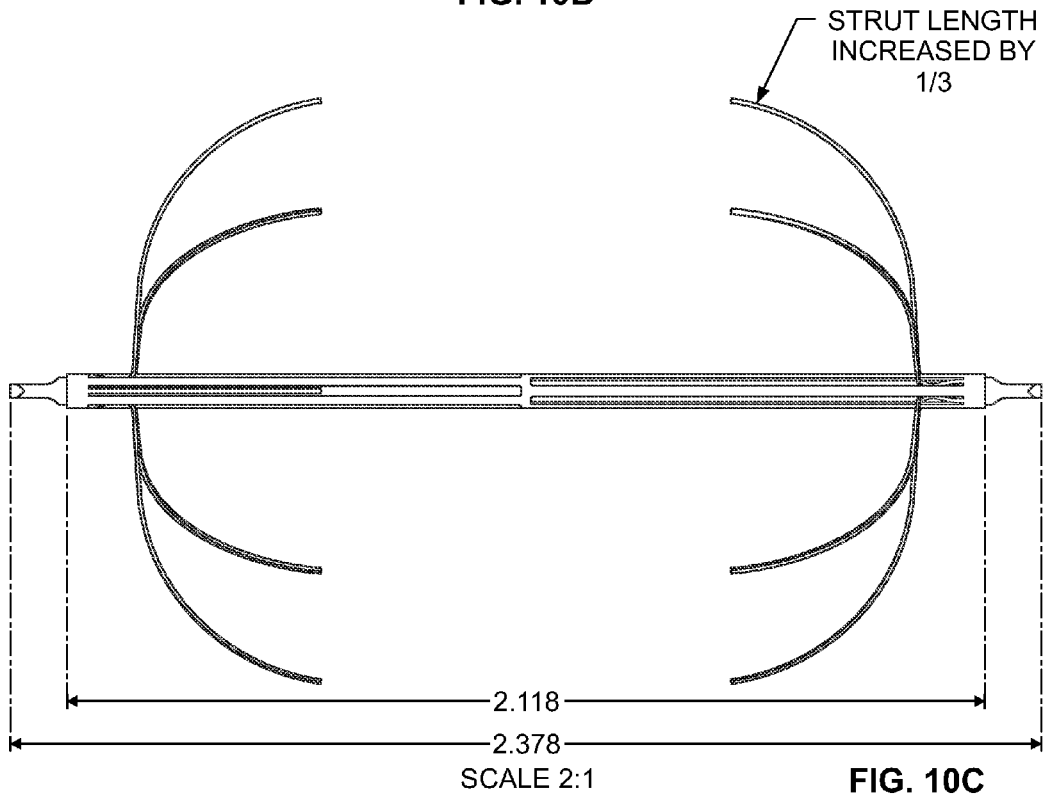
Figure 10E:
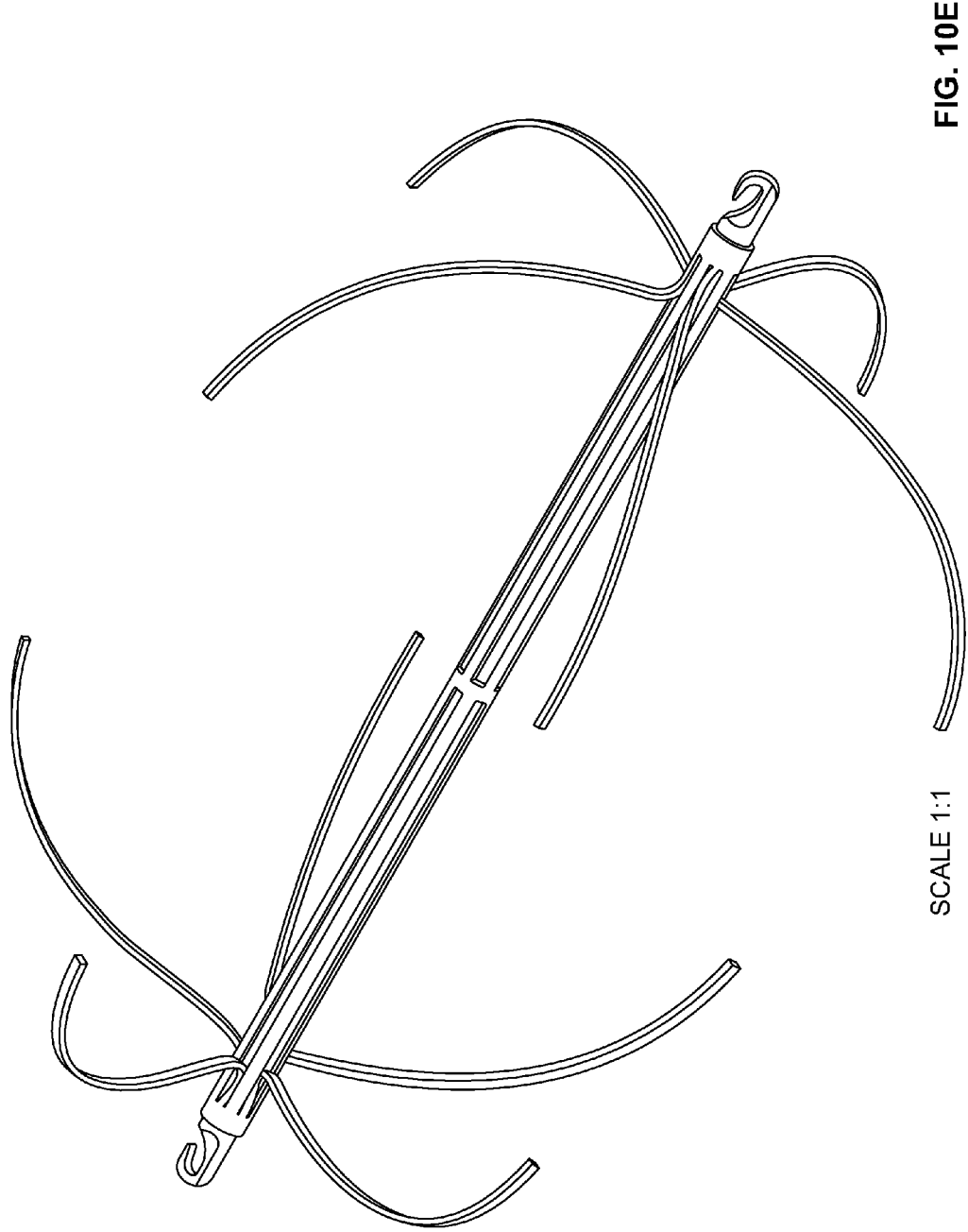

Another embodiment of the filter formed from a single tube with two sets of five expandable legs is shown in FIGS. 10a-g. The filter comprises a tube having a plurality of a first set of expandable legs and a plurality of a second set of expandable legs. Each leg of the first set and the second set has an end secured to the tube and a free end. The free end of each leg in the first set is oriented in a direction opposite to the free end of each leg in the second set. Each leg of the first and the second sets is bent inward at the end closest to the tube for easy retrieval of the filter (FIG. 10d). Each leg of the first and second set may have at least one barb at its free end. The radial positions of the second set of expandable legs may be off-set from the radial positions of the first set of expandable legs (FIG. 10g). A cage may be formed comprising the expandable legs of the first and second sets. The cage may form a sphere shape when the expandable legs of the first and second sets are deployed. At least one end of the tube has at least one notch for retrieval of the filter. There is one hook at both ends 501, 502 of the filter for retrieval of the filter. Compared to the filter in FIG. 9c, the filter in FIGS. 10a-g do not have the spiral cut pattern.

When retrieving the filter of FIG. 10a, a physician inserts a catheter into a vessel where the filter is positioned on the vessel wall, and pushes a snare through the catheter until the snare grabs the notch on the tube closest to the first set of expandable legs. The snare is pulled back on to exert tension on the filter. The catheter is pushed over each expandable leg of the first set until each expandable leg retracts from the vessel wall. The physician continues pushing the catheter over the second set of expandable legs until each expandable leg of the second set inverts and retracts from vessel wall. The catheter which encompasses the expandable legs of the first and second sets of the filter is withdrawn. The filter may alternatively be retrieved from the other end using a similar mechanism.

Figure 11A:
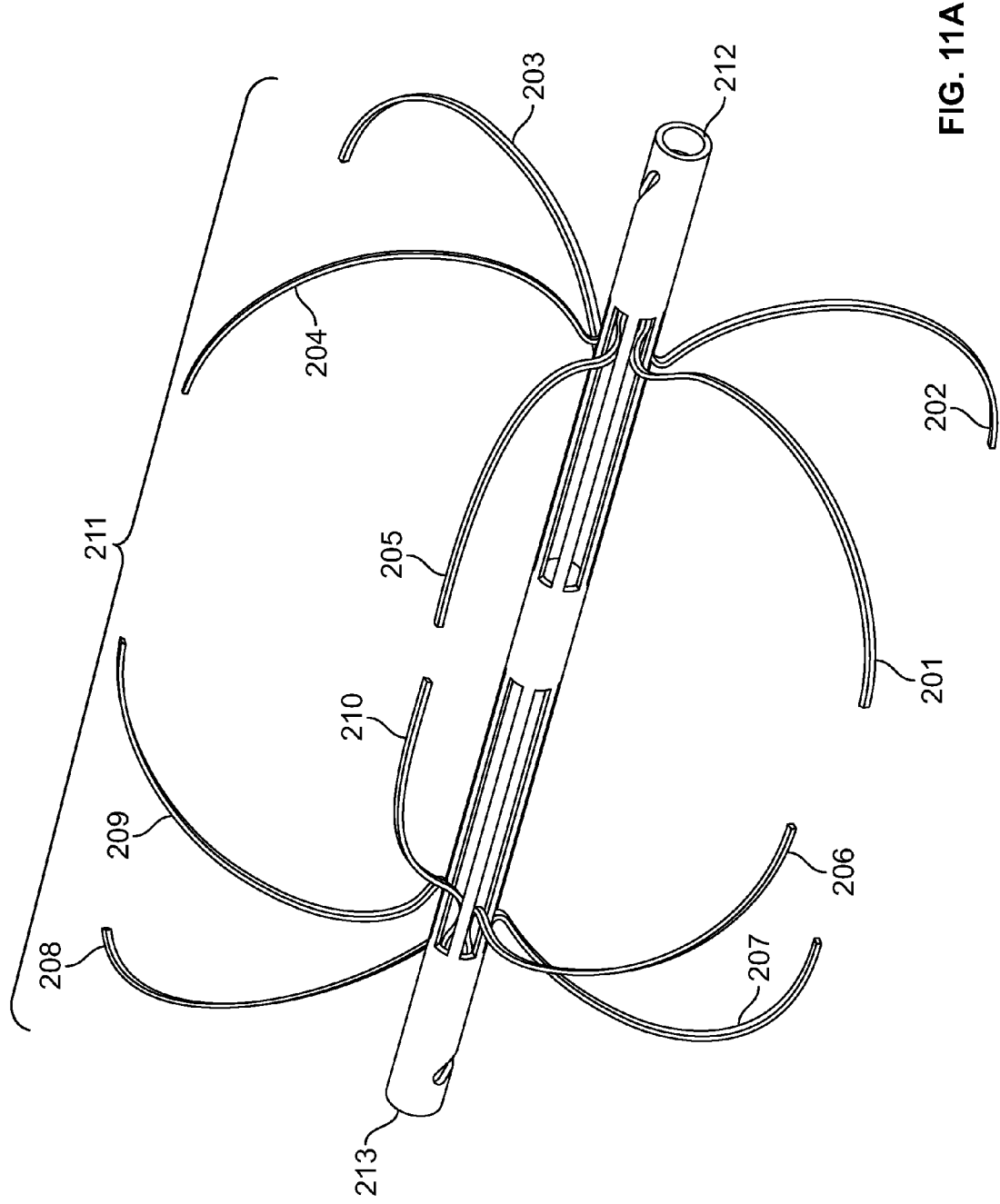
FIG. 11a shows a perspective view of one embodiment of the filter where each leg of the first and second sets is bent inward at its end to allow for easy retrieval of the filter.
Figure 11B:
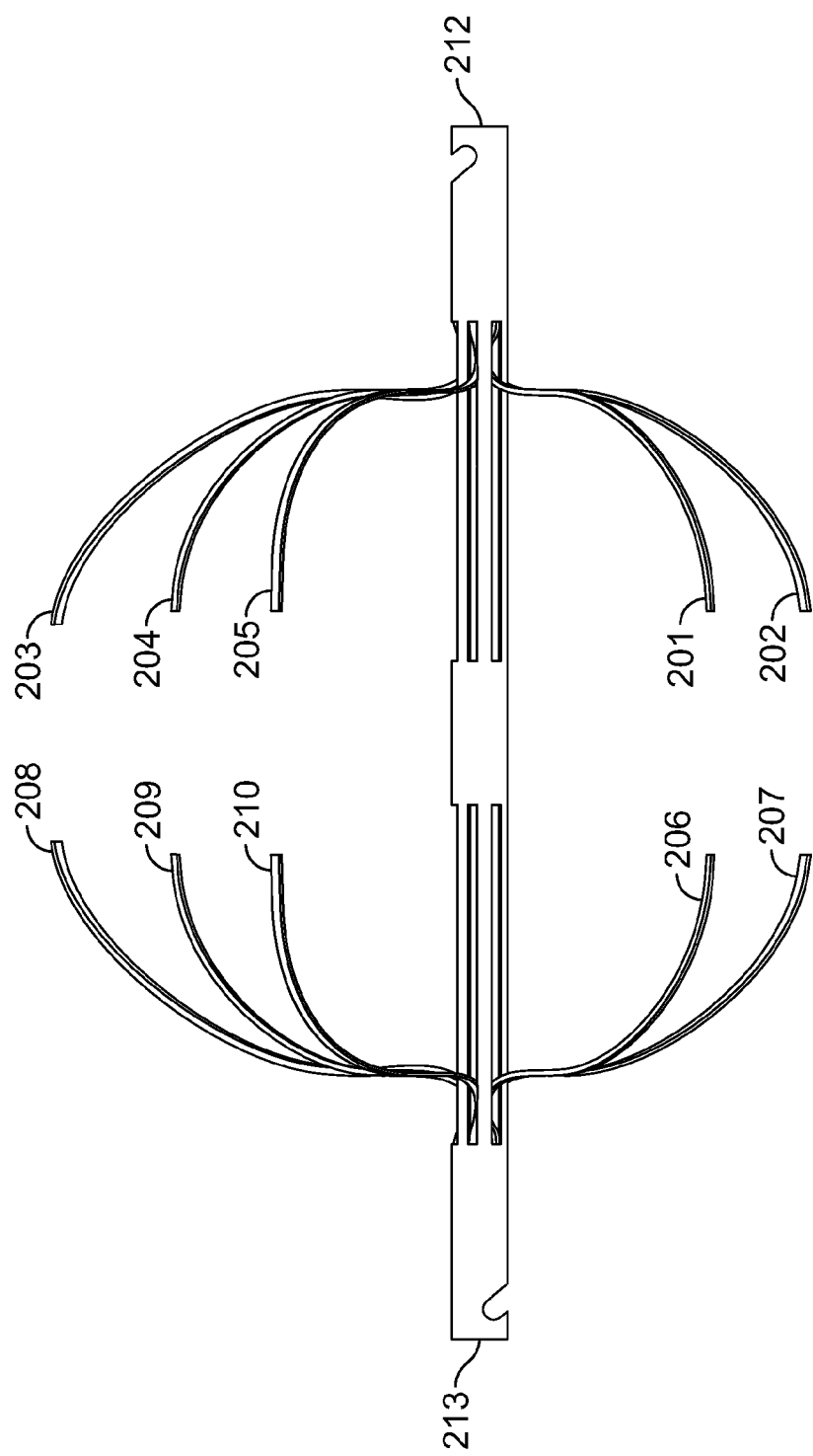
Figure 11C:
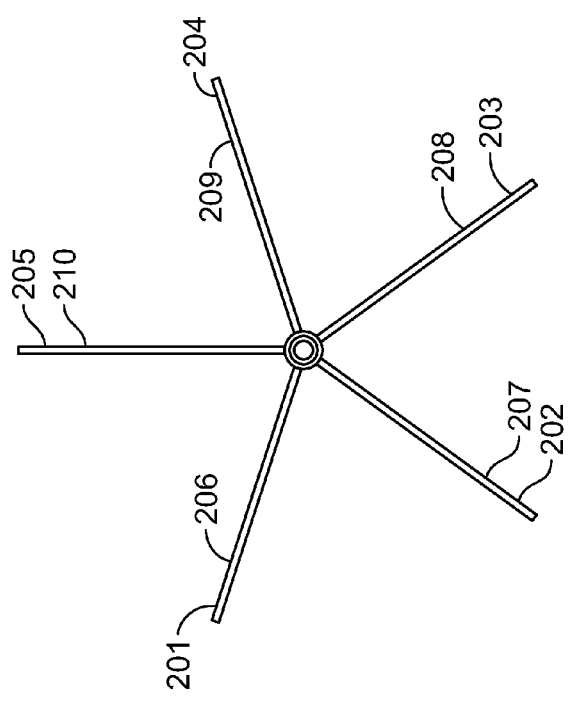
FIG. 11c shows a perspective view of the filter in FIG. 11a as it would appear looking from 212 to 213.

A sixth embodiment of the present filter is shown in FIGS. 11 a, b and c. The filter comprises a first tube and a second tube that is inserted into the first tube. The external diameter of the second tube is smaller than the internal diameter of the first tube. The filter comprises a first set of expandable legs, 201, 202, 203, 204 and 205, a second set of expandable legs 206, 207, 208, 209 and 210. These expandable legs form a cage 211. The cage 211 may take the shape of a ball or sphere when deployed.

Figure 12:
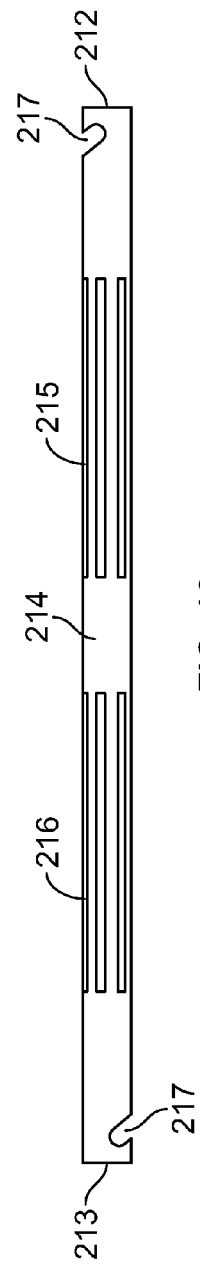

FIG. 12 shows a perspective view of the first tube of the filter in FIG. 11. The first tube 214 contains a plurality of a first set of slots 215, and a plurality of a second set of slots 216. The slots are parallel to the cylindrical axis of the first tube. The first set of slots 215 is positioned closest to the end 212 of the first tube 214. The second set of slots 216 is positioned closest to the end 213 of the first tube 214. There is one notch 217 at each end of the first tube. The lengths of the first set of slots 215 and the second set of slots 216 may be the same or be different.

The first or second sets of slots may start at a position from the ends 212 or 213 of the first tube from about 2 mm to about 15 mm, from about 4 mm to about 8 mm or from about 5 mm to about 7 mm or about 6 mm. Each slot of the first and second sets may range in length from about 4 mm to about 35 mm, from about 10 mm to about 25 mm, from about 15 mm to about 20 mm, or about 17 mm. The length of the first set of slots and the length of the second set of slots may be the same or may be different.

The first tube may have a length of about 35 mm to about 80 mm, from about 40 mm to about 70 mm, from about 45 mm to about 60 mm or about 50 mm. The internal diameter of the first tube may range from about 1.0 mm to about 1.6 mm, from about 1.2 mm to about 1.6 mm, from about 1.4 mm to about 1.5 mm or about 1.45 mm. The thickness of the first tube may range from about 0.4 mm to about 0.8 mm, from about 0.5 mm to about 0.7 mm, from about 0.5 mm to about 0.6 mm, or about 0.58 mm. The thickness of the first tube may be constant or may vary from one end to the other end. Either end of the first tube may be straight or beveled.

Figure 13A:
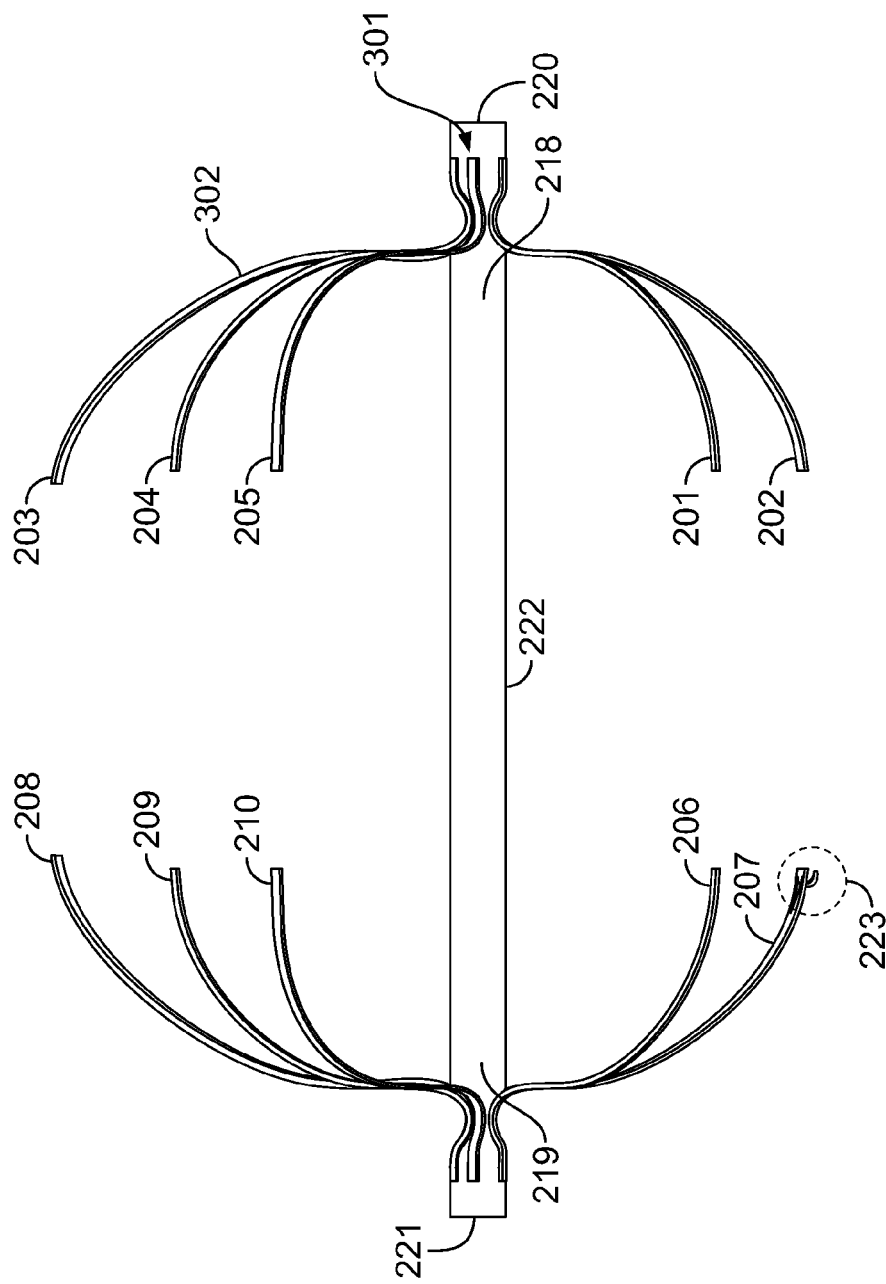
Figure 13B:
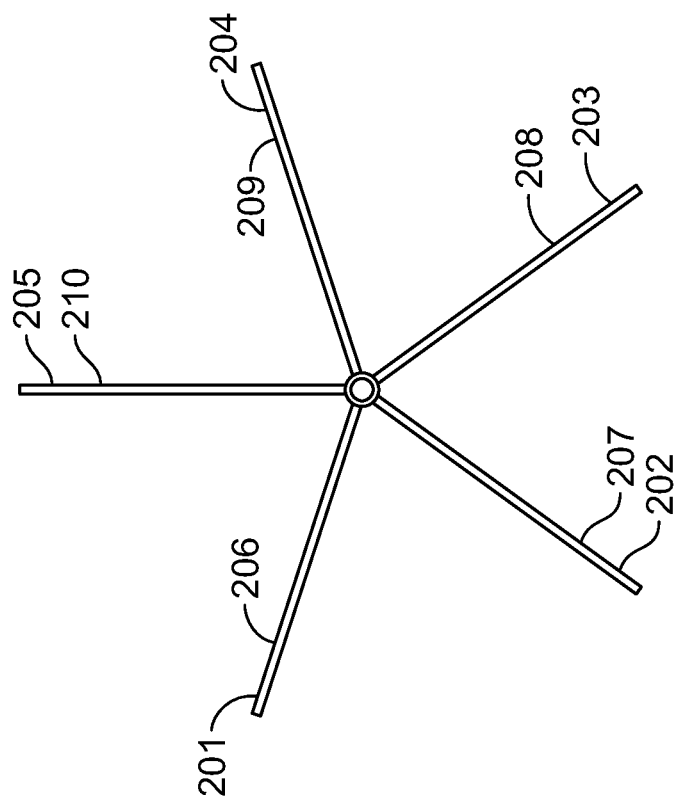
FIG. 13b shows a perspective view of the second tube in FIG. 13a as it would appear looking from 220 to 221.

FIGS. 13a and 13b show various perspective views of the second tube of the filter in FIG. 11. The second tube 222 has two ends 220, 221. The second tube is hollow and comprises two sets of expandable legs. The first set of expandable legs 201, 202, 203, 204 and 205 are attached or secured at a point 218 which is proximal to end 220 on the second tube 214. The second set of expandable legs 206, 207, 208, 209 and 210 are attached or secured at a point 219 which is proximal to end 221 on the second tube 214. The length from point 218 to 220 and the length from point 219 to 221 range from about 2 mm to about 10 mm, from 3 mm to about 8 mm, from about 4 mm to about 7 mm or about 6 mm. The length from point 218 to 220 and the length from point 219 to 221 may be the same or be different. The legs may have various shapes, including rectangular strips, wires, tubes, rods, threads, or any other desired structure. The legs may be straight, curved, tapered or have multiple angles. The shapes, configurations or dimensions of various portions of each leg may vary or be the same. The shapes, configurations, dimensions or angles of different legs of the filter may be different or may be the same. The legs may be notched, barbed, hooked or in any structure that anchors the legs in the vessel wall without interfering with the retrieval of the filter. In this embodiment shown in FIG. 13a, each leg of the first and second sets is bent first inward 301 at its end near 218 or 219, then outward 302, to allow for easy retrieval of the filter.

In this embodiment, as is apparent from FIG. 13b, the second set of expandable legs, 206, 207, 208, 209 and 210 are positioned at same radial points along the circumference of the second tube 222 as compared with the first set of expandable legs, 201, 202, 203, 204 and 205. The free ends of the first set of expandable legs 201, 202, 203, 204 and 205 are in a direction opposite to the free ends of the second set of expandable legs 206, 207, 208, 209 and 210. Each of the free ends of the first and the second set of expandable legs 201, 202, 203, 204, 205, and 206, 207, 208, 209, 210 may have a barb 223. Each slot of the first set 215 on the first tube 214 is positioned at a radial position allowing for deployment of the first set of expendable legs, 201, 202, 203, 204 and 205. Each slot of the second set 216 on the first tube 214 is positioned at a radial position allowing for deployment of the second set of expendable legs 206, 207, 208, 209 and 210.

The external diameter of the second tube is less than the internal diameter of the first tube. The filter of the present invention is assembled by inserting the second tube 227 into the first tube 220. All the expandable legs on the second tube are straight, i.e., not expanded, during insertion.

The first and second sets of expandable legs on the second tube may have a length of about 10 mm to about 30 mm, from about 15 mm to about 25 mm or about 20 mm. The expandable legs of each set may have a width ranging from 0.05 mm to about 1.5 mm, from about 0.1 mm to about 1.0 mm, from about 0.3 mm to about 0.8 mm or about 0.35 mm. The width of the first and second sets of expandable legs may be constant or vary. For example, in one embodiment, the width of the first and second set of expandable legs may taper or narrow from the point where it is secured to the barbed end. The expanded diameter of the first and second set of expandable legs may range from 10 mm to about 45 mm, from about 15 mm to about 40 mm, from about 20 mm to about 36 mm or about 30 mm.

The dimensions of the second tube may vary. For example, the straight length of the second tube may range from about 25 mm to about 60 mm, from about 30 mm to about 50 mm or from about 35 mm to about 48 mm or about 45 mm. The external diameter of the second tube may vary from about 0.5 mm to about 1.5 mm, from about 0.8 mm to about 1.5 mm, from about 1.2 mm to about 1.5 mm, from 1.4 mm to about 1.5 mm or about 1.45 mm, provided that the external diameter of the second is less than the internal diameter of the first tube. The thickness of the second tube may range from about 0.3 mm to about 0.6 mm, from about 0.4 mm to about 0.5 mm or from about 0.4 mm to about 0.45 mm. The diameter of the first tube may be the same as the diameter of the second tube or may be different.

Figure 14A:
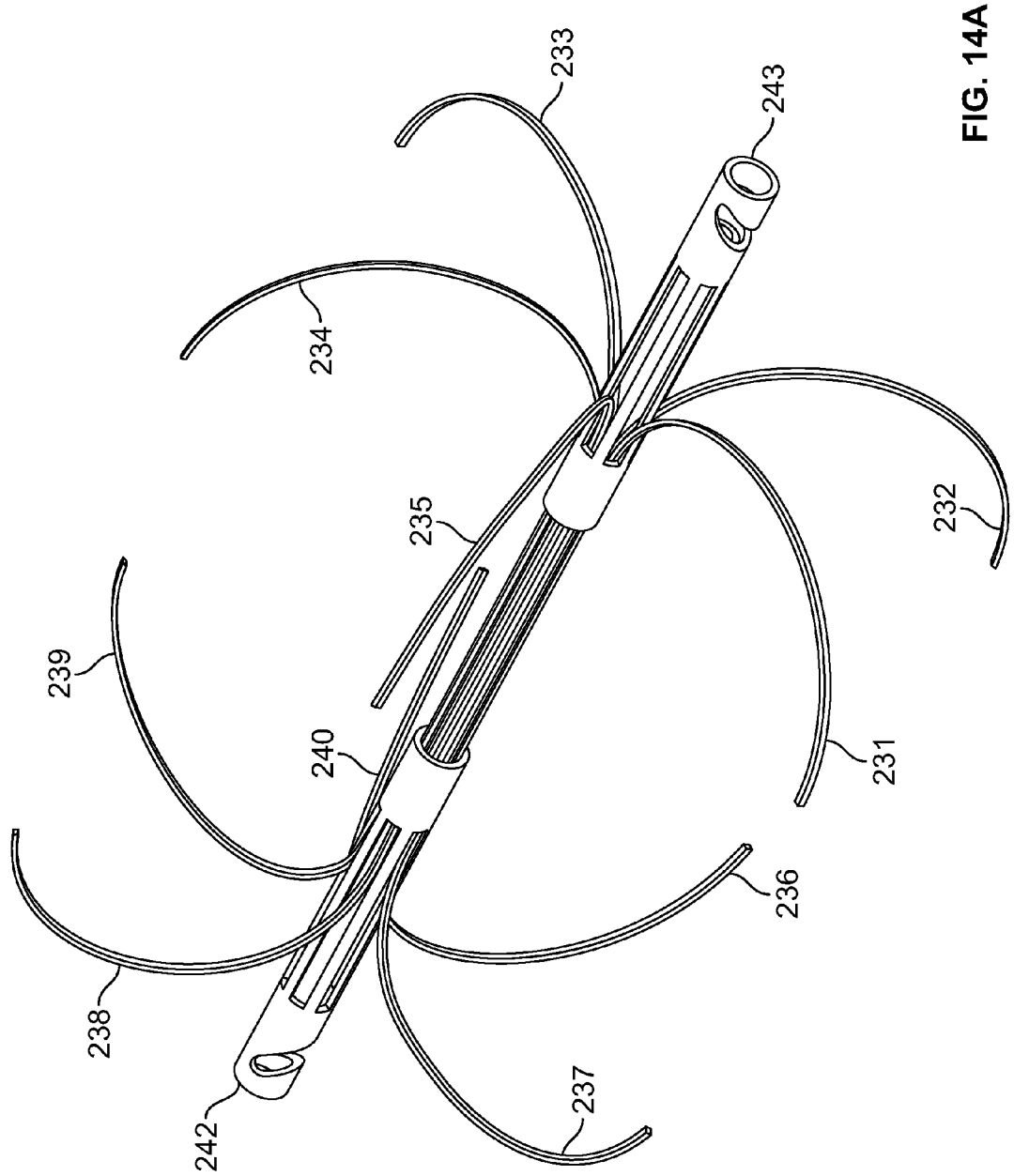
FIG. 14a shows a perspective view of another embodiment of the filter where each leg of the first and second sets is bent inward at its end to allow for easy retrieval of the filter.
Figure 14B:
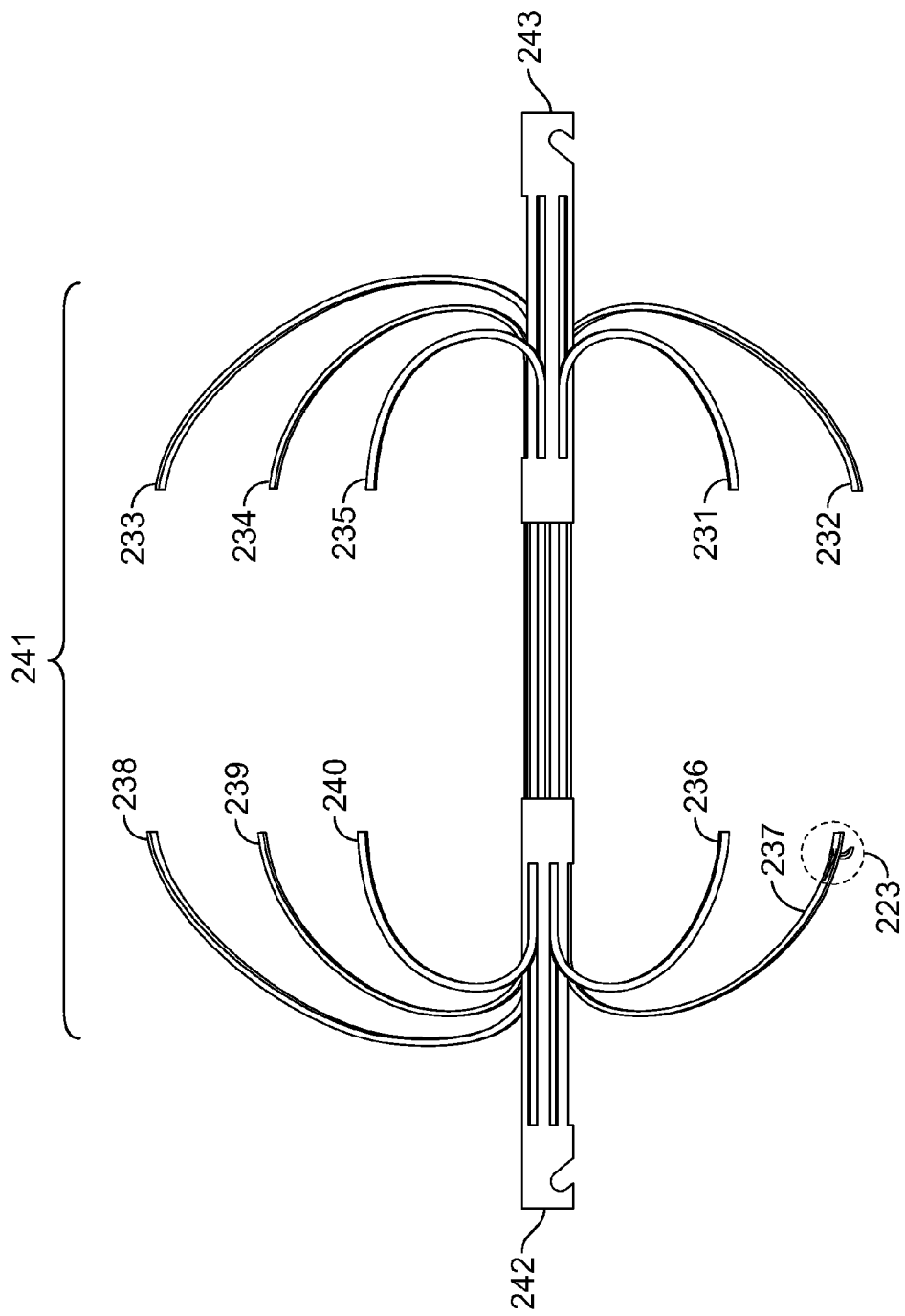
Figure 14C:
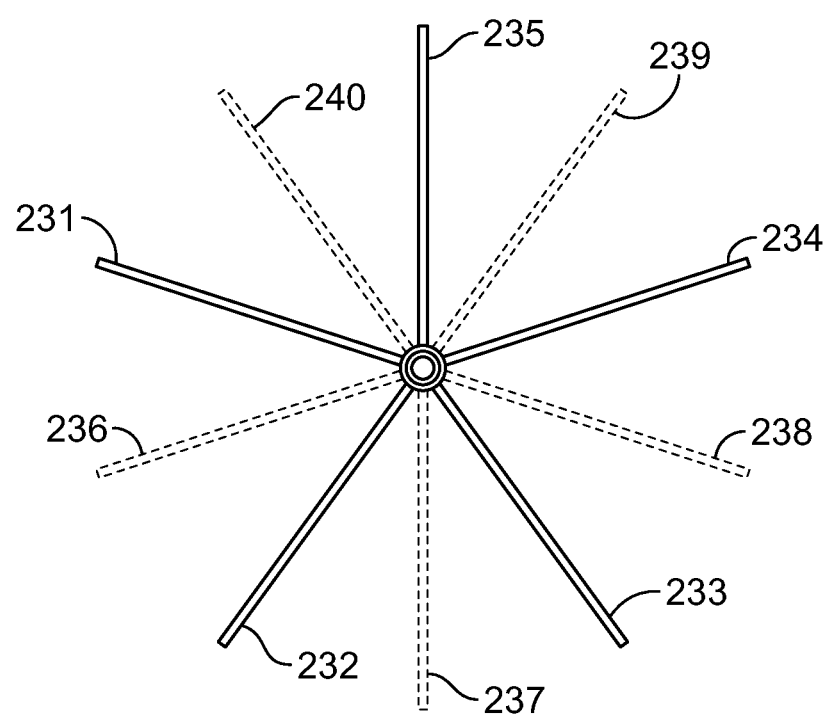
FIG. 14c shows a perspective view of the filter in FIG. 14a as it would appear looking from 243 to 242.

A seventh embodiment of the present filter is shown in FIG. 14a, b, c. The filter is formed from two tubes with two sets of five expandable legs, the first expandable set, 231, 232, 233, 234, 235, and the second expandable set, 236, 237, 238, 239, 240. These expandable legs form a cage 241. The cage 241 may take the shape of a ball or sphere when deployed. In this embodiment, as is apparent from FIG. 14c, the first set of expandable legs, 231, 232, 233, 234, 235 are positioned at different radial points along the circumference of the first tube as compared with the second set of expandable legs, 236, 237, 238, 239, 240. The free ends of the first set of expandable legs 231, 232, 233, 234, 235 are in a direction opposite to the free ends of the second set of expandable legs 236, 237, 238, 239, 240. Each of the free ends of the first and the second set of expandable legs 231, 232, 233, 234, 235, and 236, 237, 238, 239, 240 may have a barb 223 (FIG. 14b).

Figure 15:
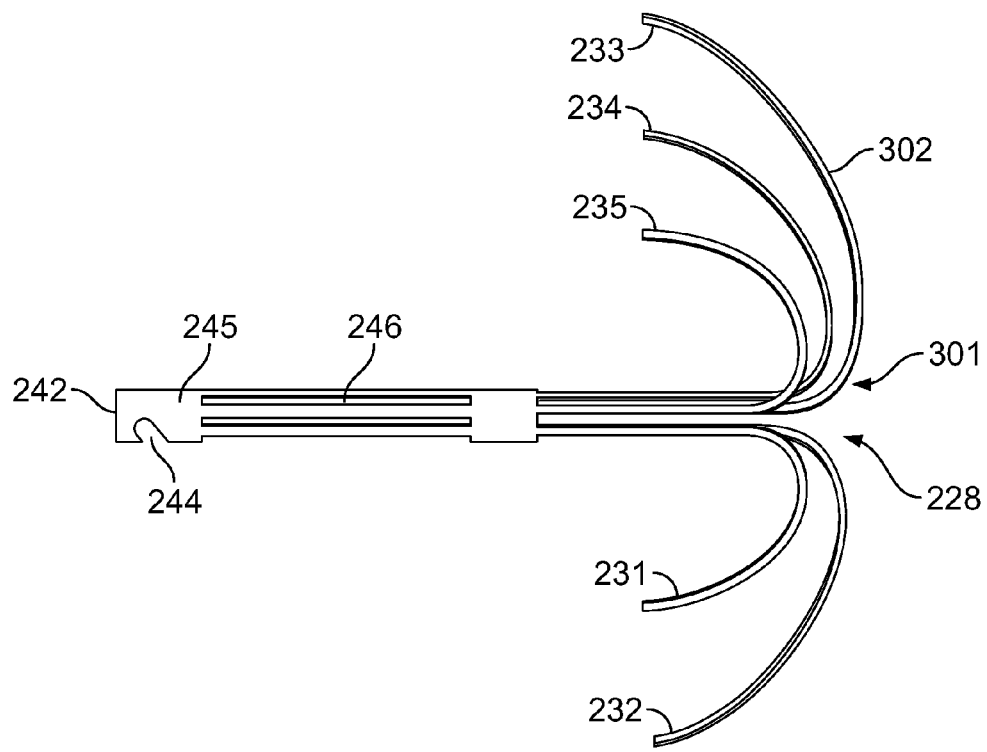
Figure 16:
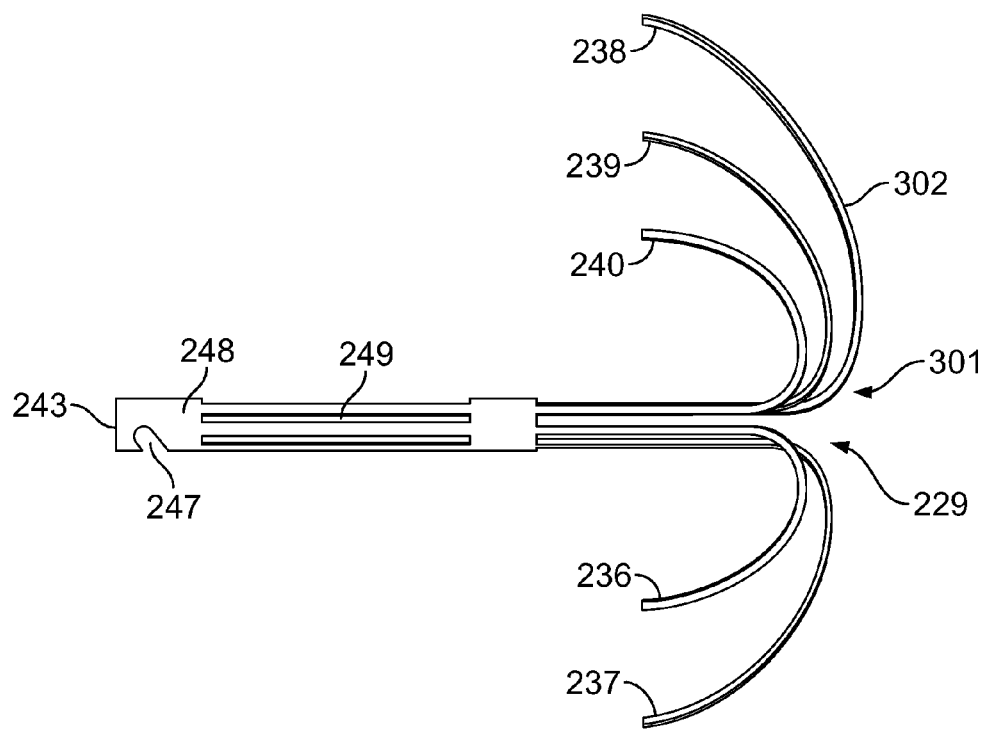

FIG. 15 shows a perspective view of the first tube of the filter in FIG. 14. The first tube 245 contains a plurality of a first set of slots 246 which are parallel to the long or cylindrical axis of the first tube, and a plurality of a first set of expandable legs 231, 232, 233, 234, 235. There is one notch 244 at the end 242 of the first tube 245. FIG. 16 shows perspective view of the second tube. The second tube 248 contains a plurality of a second set of slots 249 which are parallel to the long or cylindrical axis of the second tube, and a plurality of a second set of expandable legs 236, 237, 238, 239, 240. There is one notch 247 at the end 243 of the second tube 248. The length of the first set of slots 246 and the second set of slots 249 may be the same or be different. Each slot of the first set 246 on the first tube 245 is positioned at a radial position allowing for deployment of the second set of expendable legs, 236, 237, 238, 239, 240 of the second tube 248. Each slot of the second set 249 on the second tube 248 is positioned at a radial position allowing for deployment of the first set of expendable legs 231, 232, 233, 234, 235 of the first tube 245. The diameter of the first tube may be the same as the diameter of the second tube or may be different. The legs may have various shapes, including rectangular strips, wires, tubes, rods, threads, or any other desired structure. The legs may be straight, curved, tapered or have multiple angles. The shapes, configurations or dimensions of various portions of each leg may vary or be the same. The shapes, configurations, dimensions or angles of different legs of the filter may be different or may be the same. The legs may be notched, barbed, hooked or in any structure that anchors the legs in the vessel wall without interfering with the retrieval of the filter. In this embodiment shown in FIGS. 15 and 16, each leg of the first and set sets is bent first inward 301 at its end near 228 or 229, then outward 302, to allow for easy retrieval of the filter.

Figure 17A:
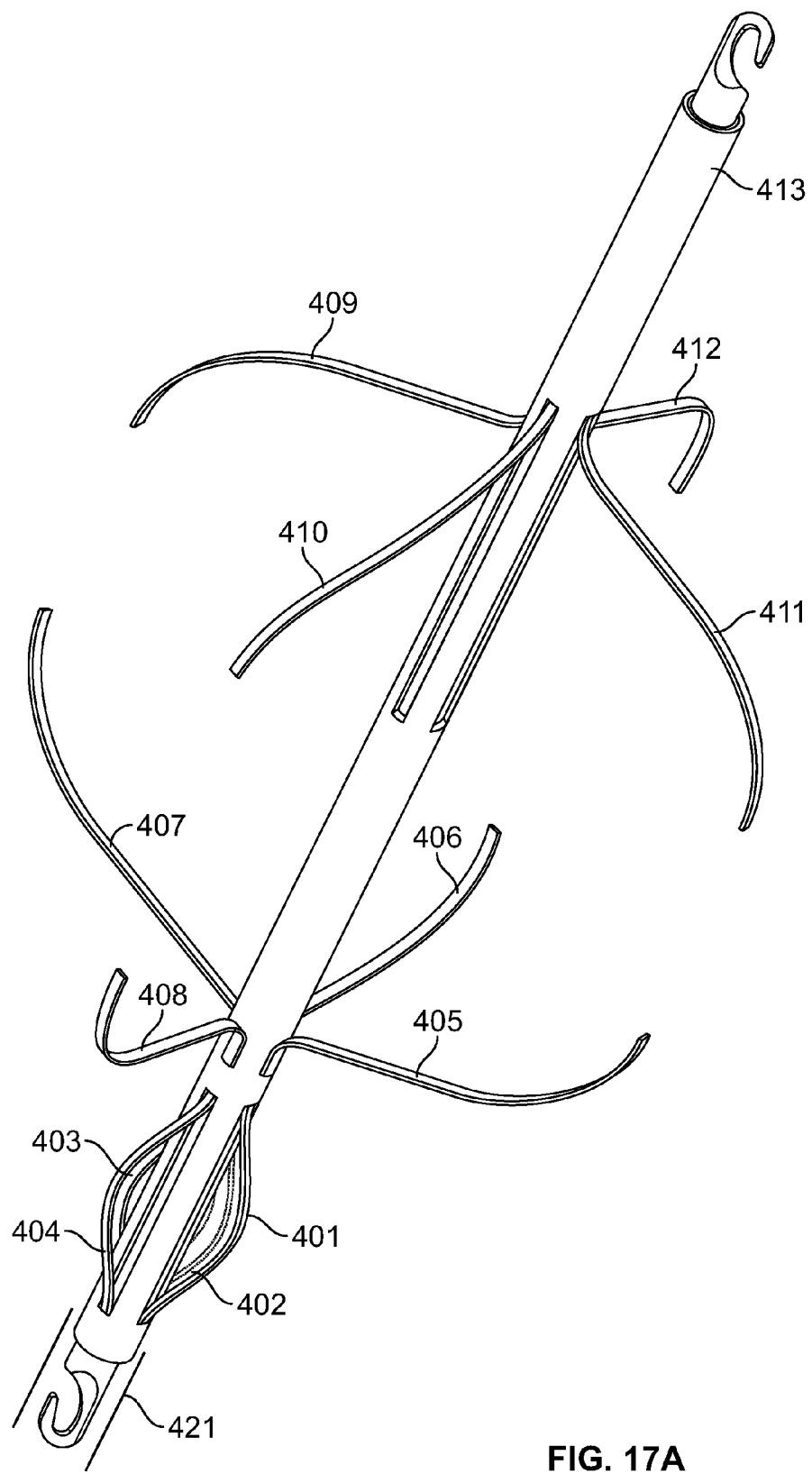
FIG. 17a shows the filter where the third set of expandable legs are positioned on one side of the filter.
Figure 17B:
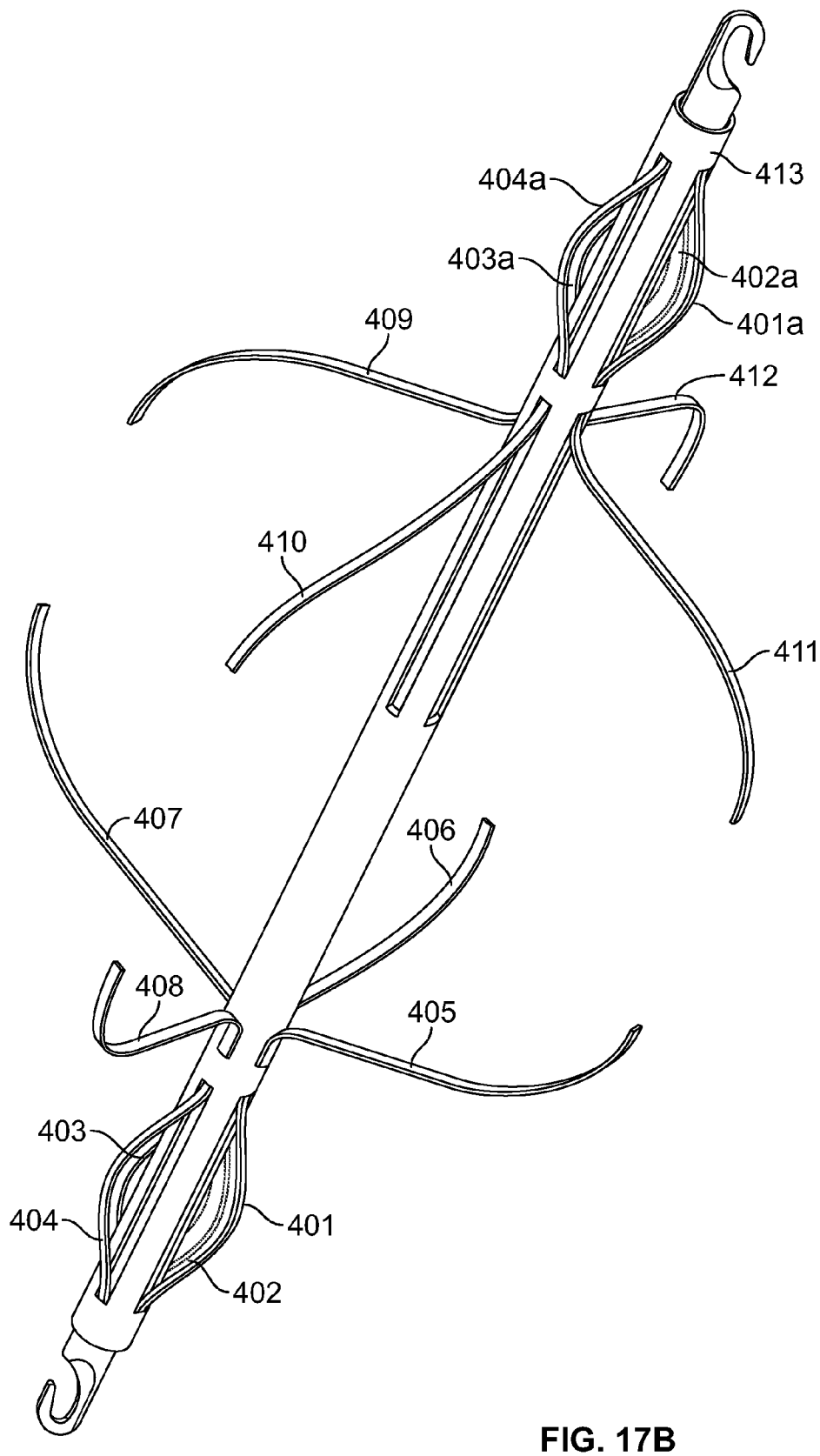
FIG. 17b shows the filter where the third set of expandable legs are positioned on both sides of the filter.
Figure 18:
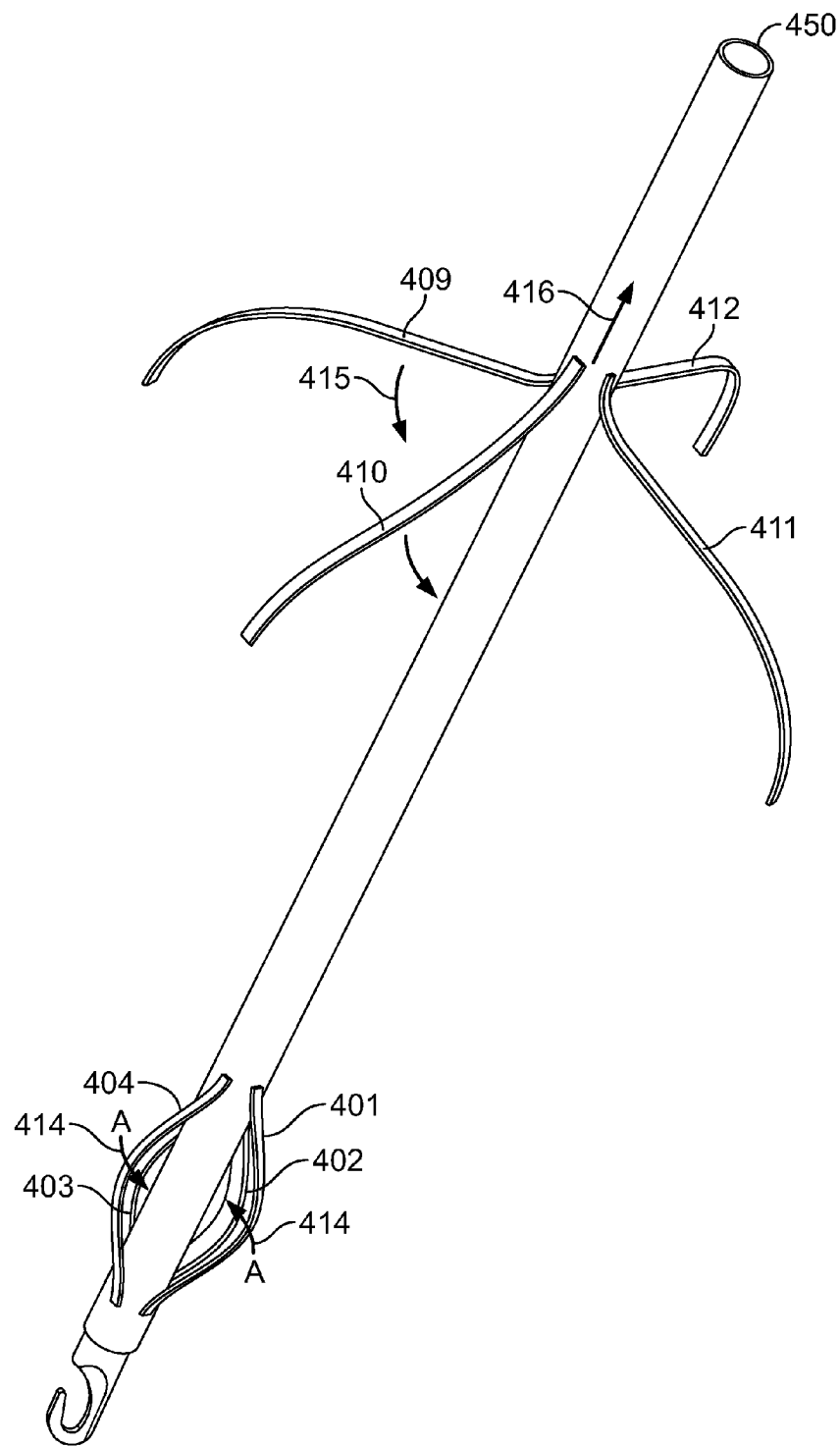

FIG. 17*a* presents yet another embodiment of the filter of the present invention. The filter is formed from a first tube 422 (FIG. 19) and a second tube 450 (FIG. 18). The first tube 422 has a plurality of a first set of slots 451, a second set of slots 420, and a plurality of a first set of expandable legs 405, 406, 407 and 408. The second tube 450 has a plurality of a second set of expandable legs 409, 410, 411, 412, and a plurality of a third set of legs 401, 402, 403 and 404. Each leg of the first set has an end secured to the first tube and a free end. Each leg of the second set has an end secured to the second tube and a free end. The free end of each leg in the first set is oriented in a direction opposite to the free end of each leg in the second set. Each leg of the third set comprising an expandable segment and having both ends secured to the second tube. The first set of slots on the first tube is positioned at radial positions allowing for deployment of the second set of legs. The second set of slots on the first tube is positioned at radial positions allowing for deployment of the expandable segment in each leg of the third set. Each slot on the first tube is oriented parallel to the cylindrical axis of the first tube. The radial positions of the second set of expandable legs may be the same as or be off-set from the radial positions of the first set of expandable legs. The second tube's external diameter is less than the first tube's internal diameter. The filter is formed by inserting the second tube into the first tube. A cage may be formed comprising the expandable legs of the first and second sets. The cage may form a sphere shape when the expandable legs of the first and second sets are deployed. In this embodiment, a third set of expandable legs, 401, 402, 403, 404, is positioned at one side of the filter 413. As described previously, the filter has two sets of opposing expandable legs, a first set, 405, 406, 407, 408 and a second set, 409, 410, 411, and 412. The third set of expandable legs, 401, 402, 403, and 404 may be positioned at either end of filter 413. FIG. 17*b* shows another embodiment of the filter where there are two sets of expandable legs positioned at either end of the filter, 401, 402, 403 and 404 and 401(*a*), 402(*a*), 403(*a*) and 404(*a*).

When retrieving the filter in FIG. 17*a*, a physician inserts a catheter into a vessel where the filter is positioned on the vessel wall. The physician then pushes a snare through the catheter until the snare grabs the notch. The snare is pulled back on to exert tension on the filter. The catheter is pushed over the snare and each expandable leg of the third set until each expandable leg of the third set straightens, each expandable leg of the first set retracts from the vessel wall, and each expandable leg of the second set retracts from vessel wall. The catheter which encompasses the expandable legs of the first, second and third sets of the filter is withdrawn.

Figure 19:
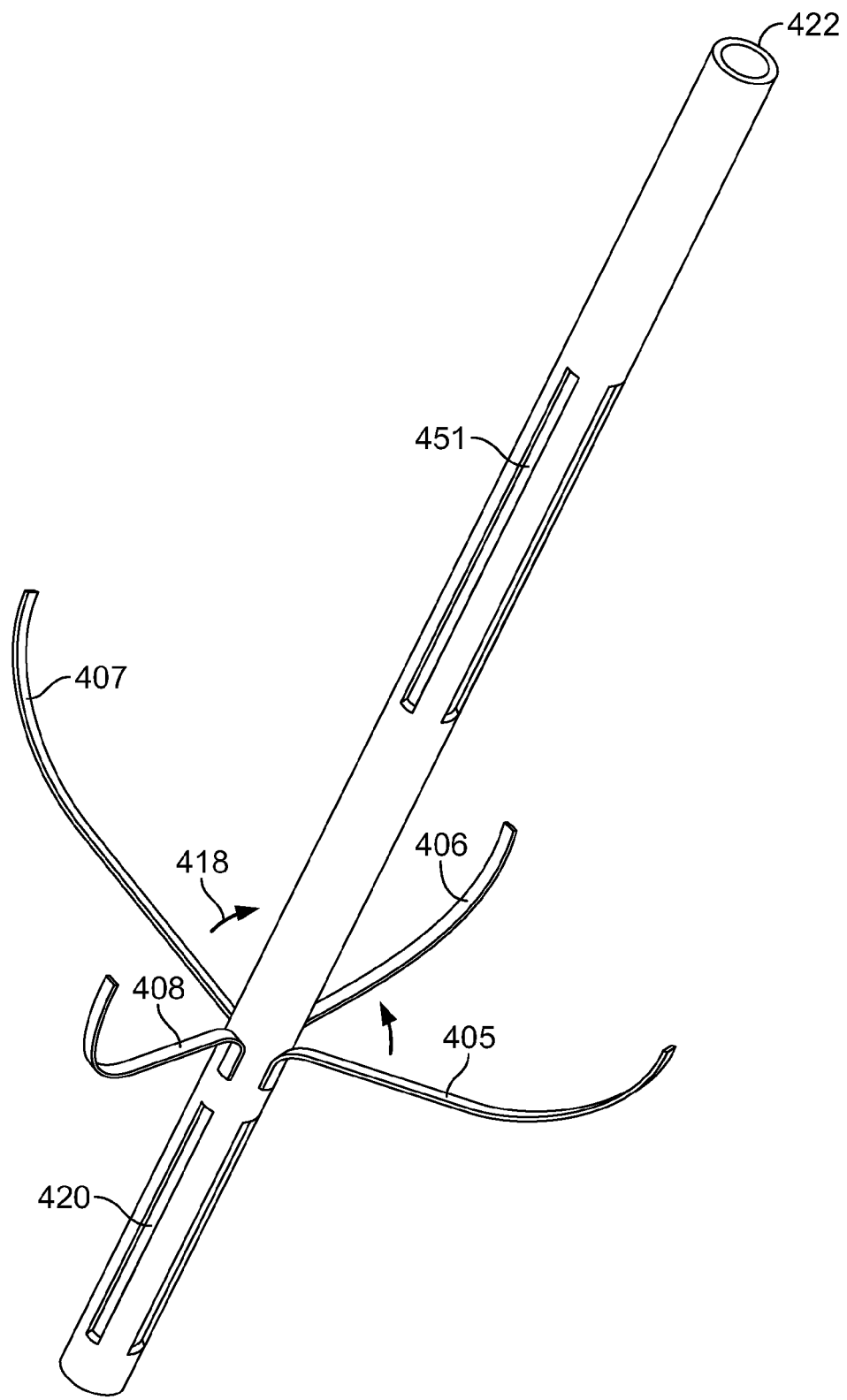

FIG. 18 shows the second tube 450 of the filter in FIG. 17*a*. When the third set of expandable legs 401, 402, 403 and 404 are radially compressed inwards 414 towards the body of the filter 413, a vector of force 416 is transmitted to the expandable legs 409, 410, 411 and 412 on the opposite side of the filter 413. This force vector 416 results in a force vector 415 which forces the second set of expandable legs 409, 410, 411 and 412 inwards towards the body of the filter 413. FIG. 19 shows the first tube 422 of the filter in FIG. 17*a*. When a catheter sheath 421 is inserted over one end of the filter 413, the third set of expandable legs, 401 and 404 in this illustration, are compressed inwards, resulting in the transmission of forces vectors as discussed above. The first set of expandable legs, 405, 406, 407 and 408, are also pushed inwards 418 as the catheter 421 is pushed over the first set of expandable legs.

Figure 20:
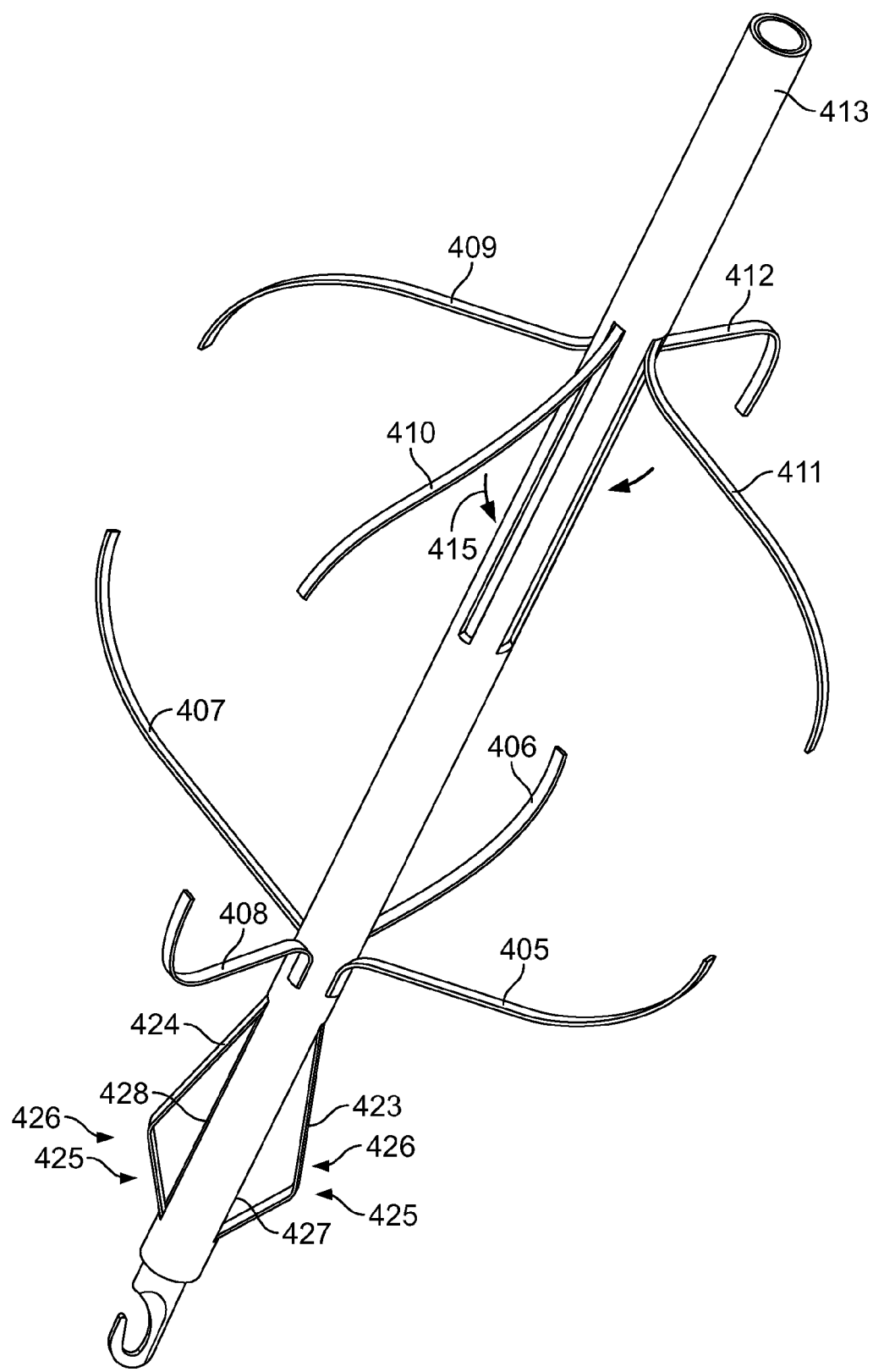
FIG. 20 shows the filter where there are tapered metal segments positioned at one end of the filter.
Figure 21A:
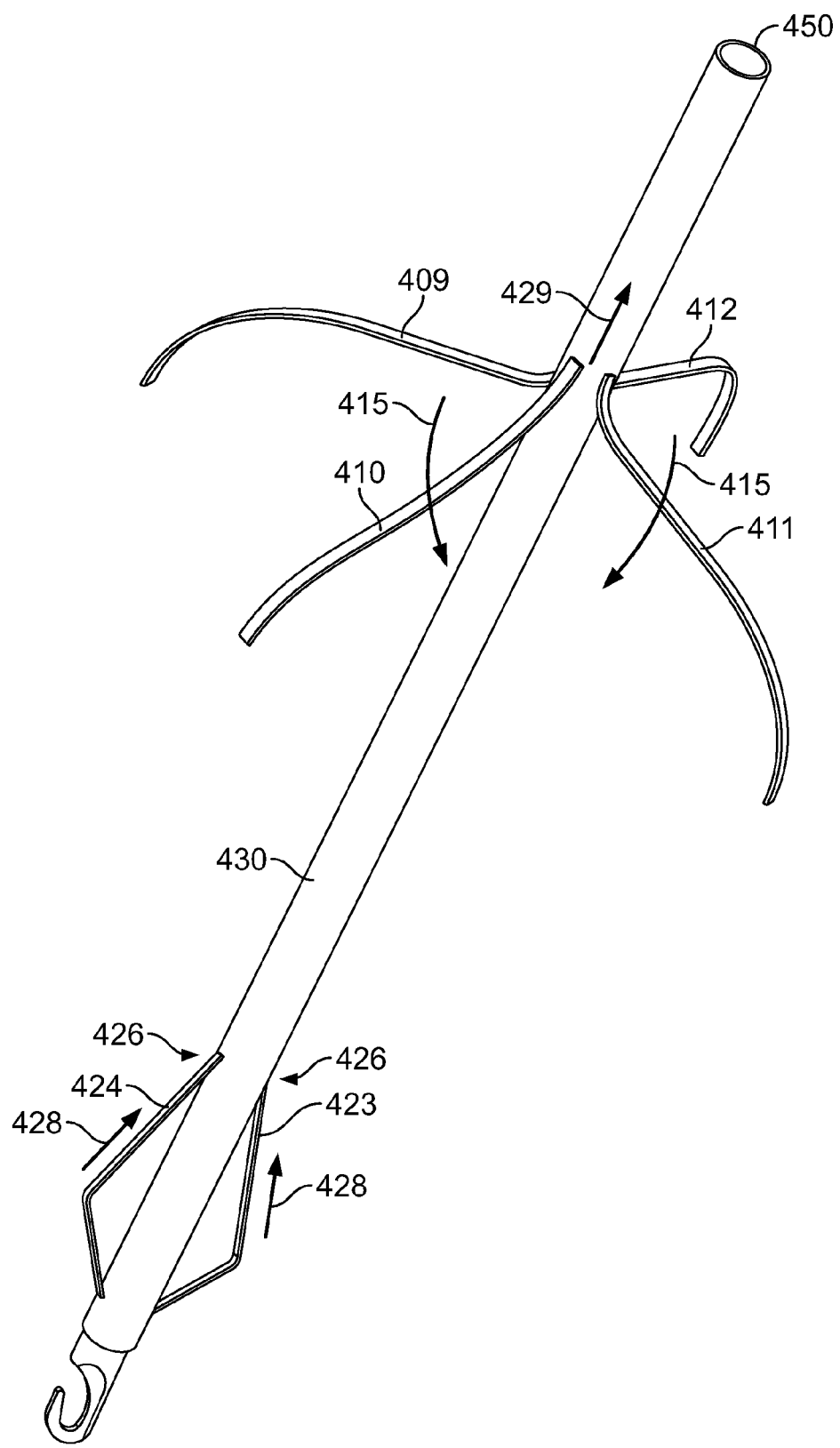
FIG. 21a shows the second tube of the filter in FIG. 20.
Figure 21B:
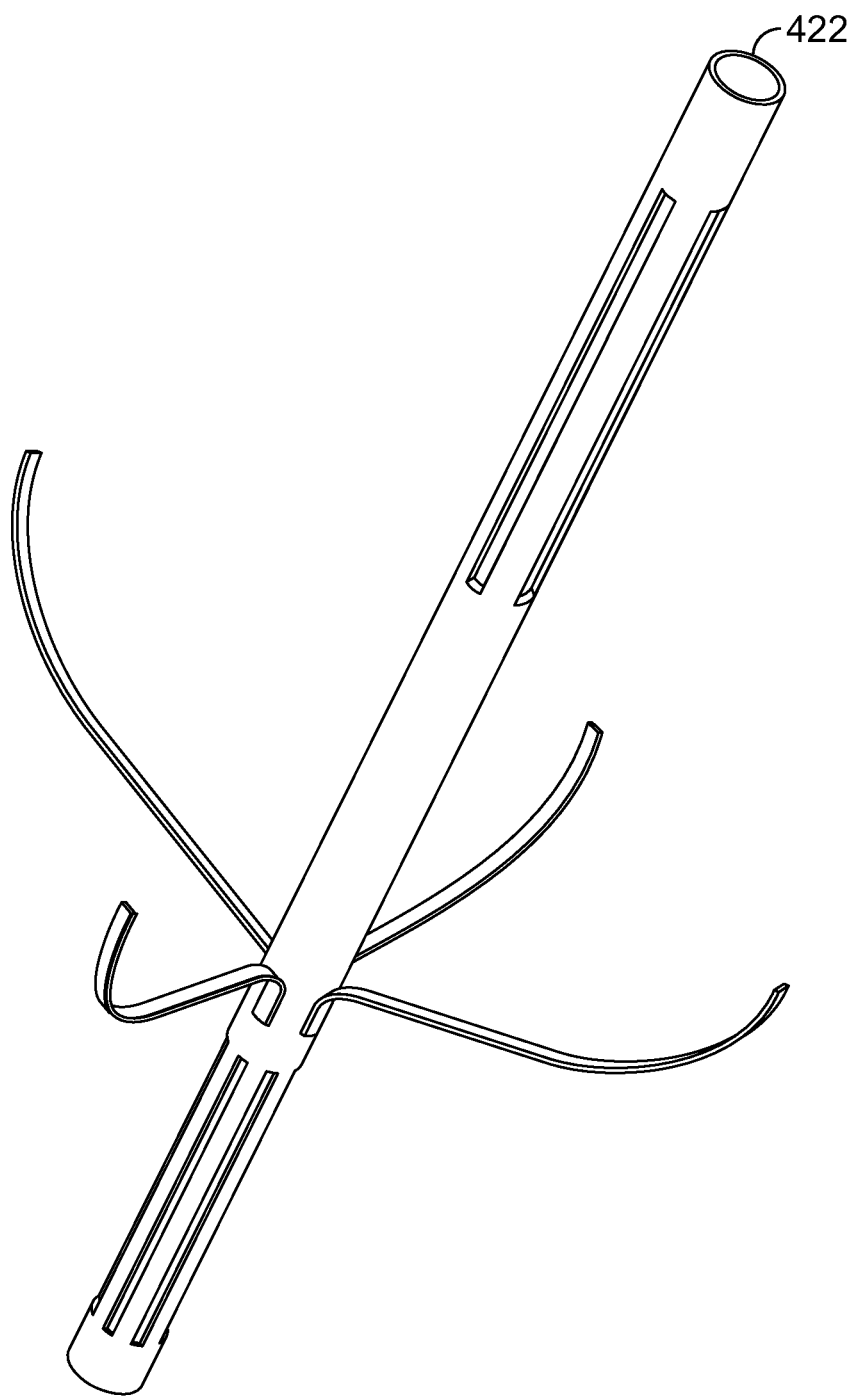
FIG. 21b shows the first tube of the filter in FIG. 20.

FIG. 20 presents another embodiment of the filter. In this embodiment, the filter has two sets of expandable legs, a first set 405, 406, 407 and 408, and a second set 409, 410, 411 and 412. However, instead of having a third set of expandable legs, the filter has a set of tapered pieces or fin-like structure, 423, 424 (the number of tapered pieces corresponds to the number of expandable legs). The design shape of the tapered pieces, 423, 424, may take various forms, including triangular and semicircular and other suitable forms. FIG. 21*a* shows the second tube 450 of the filter in FIG. 20. FIG. 21*b* shows the first tube 422 of the filter in FIG. 20. The tapered pieces are present in slots, 427, 428, in the first tube 422. The number of slots corresponds to the number of tapered pieces. When a catheter sheath 428 is pushed over the filter 413, the tapered pieces 423, 424, are compressed inwards 425. This inwards compression 426 transmits a force 429 along a connected segment 430 to the second set of expandable legs, 409, 410, 411 and 412, forcing these expandable legs inwards 415.

Figure 22A:
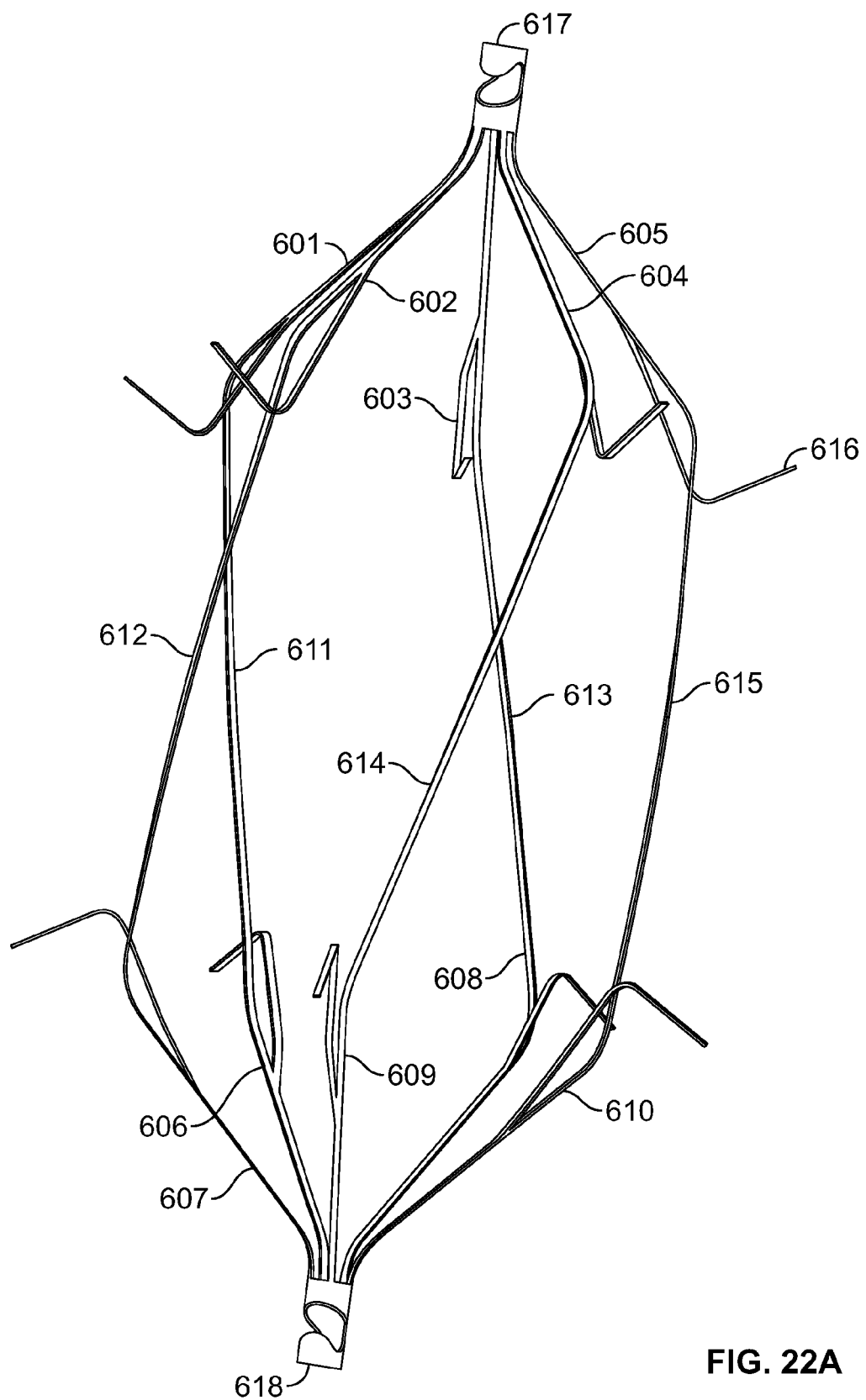
FIG. 22a shows a perspective view of one embodiment of the filter where the legs of the first and second sets are connected to form a "closed cage".
Figure 22B:
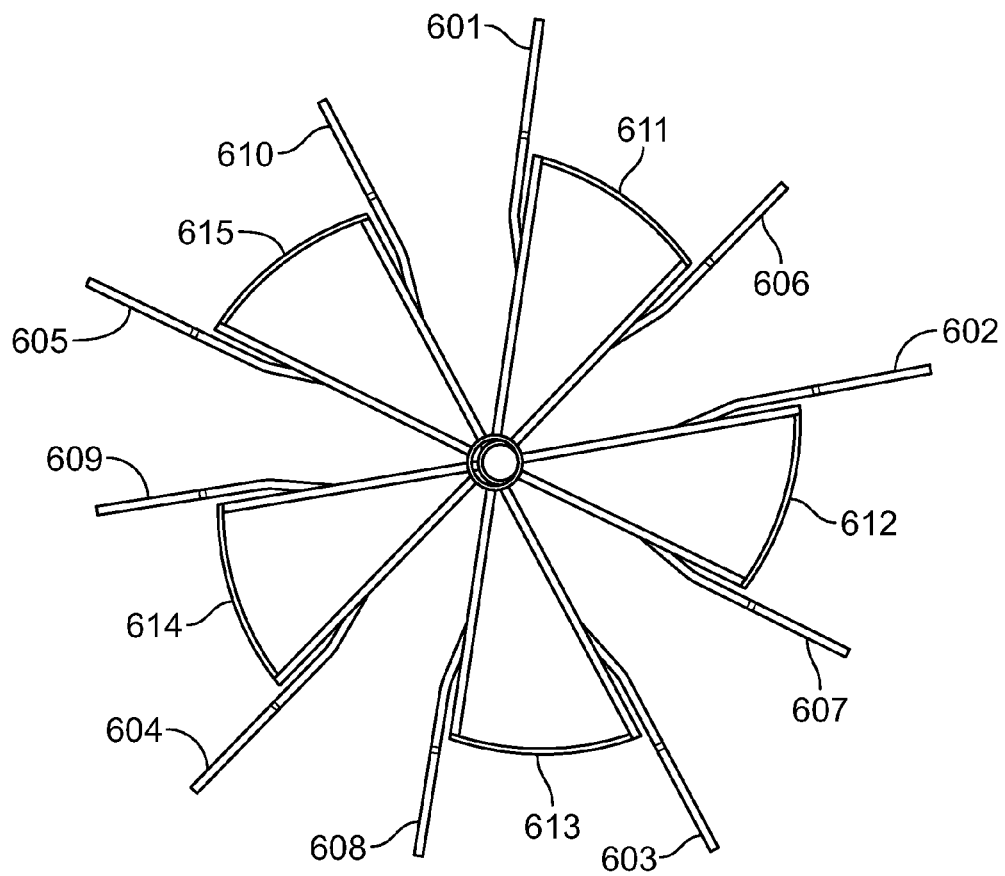
FIG. 22b shows a perspective view of the filter in FIG. 22a as it would appear looking from 617 to 618.

FIGS. 22*a* and 22*b* present another embodiment of the filter. In this embodiment, the legs of the first and second sets are connected to form a "closed cage". The filter comprises a first set of expandable legs, 601, 602, 603, 604 and 605, a second set of expandable legs 606, 607, 608, 609 and 610, and a set of connectors 611, 612, 613, 614 and 615. The first set of expandable legs, 601, 602, 603, 604 and 605, are connected to the second set of expandable legs 606, 607, 608, 609 and 610 by the connectors 611, 612, 613, 614 and 615, respectively. The expandable legs of the first and second sets, as well as the connectors, form a cage (FIGS. 22*a* and *b*). The legs of the first set and/or the second set may have at least one barb. The filter has two ends 617 and 618. At least one end of filter has at least one notch for retrieval of the filter. FIG. 22*b* shows a perspective view of the filter in FIG. 22*a* as it would appear looking from 617 to 618.

Figure 23:
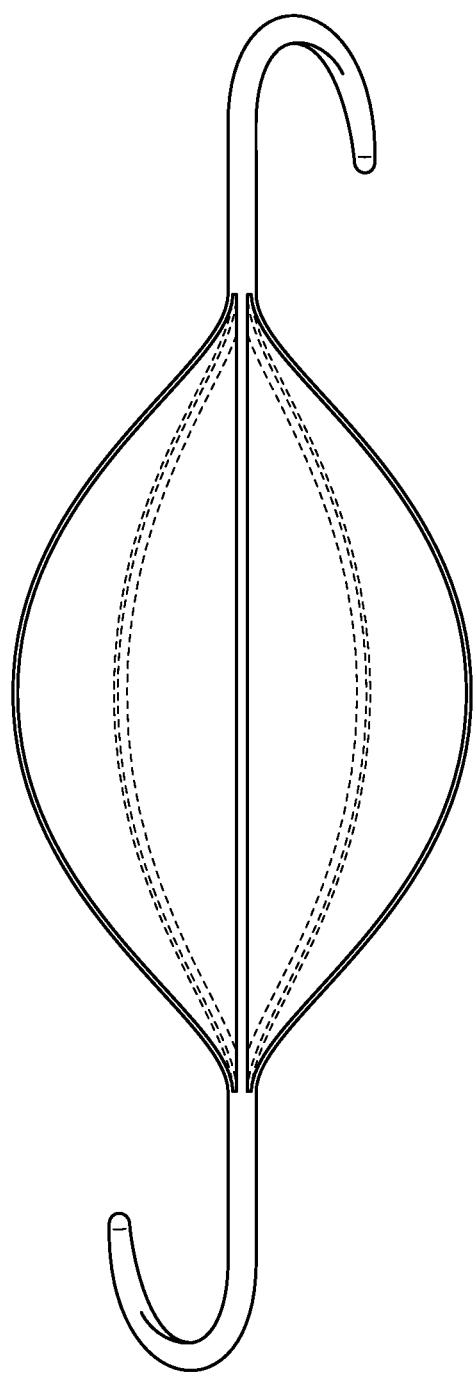
FIG. 23 shows a perspective view of one embodiment of the filter where the filter is formed from a "closed cage".

FIG. 23 illustrates one embodiment of the filter where the filter is formed from a "closed cage". The cage contains six wires connecting the two ends of the filter. In certain embodiments, the cage may contain about 3 to about 8 wires connecting the two ends of the filter. At least one end of filter has at least one notch or hook for retrieval of the filter.

Figure 24:
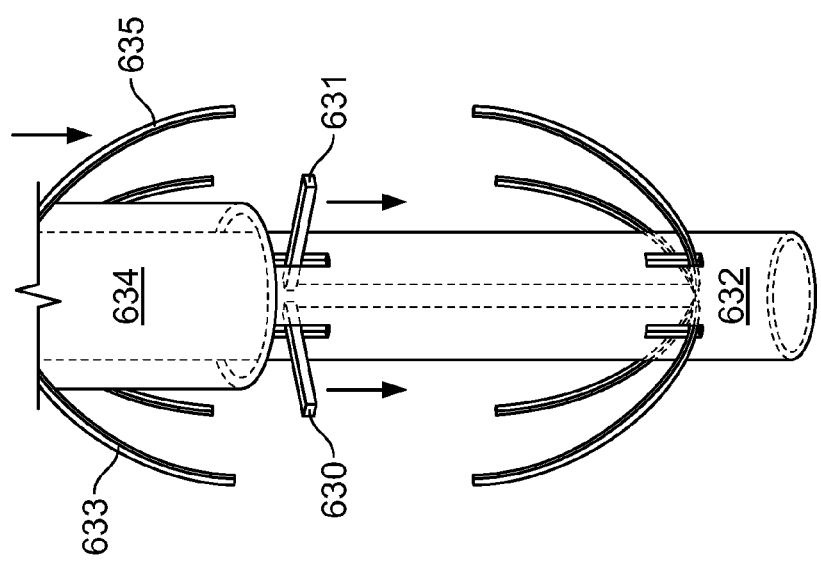
FIG. 24 shows a perspective view of one embodiment of the filter where the filter contains a plurality of handles to close the second set of legs.

FIG. 24 shows one embodiment of the filter where the filter contains a plurality of handles to close the second set of legs. The filter comprises a first set and a second set of legs. These expandable legs form a cage. Each leg of the first set has an end secured on the outer tube and a free end. Each leg of the second set has an end secured on the inner tube and a free end. The free ends of the first set of expandable legs are in a direction opposite to the free ends of the second set of expandable legs. The free ends of the first and second set of expandable legs may have a barb. There is one hook at both ends of the filter for retrieval of the filter. There are a plurality of handles 630 connected to the inner tube at a point 631 distal to the point 632 where the second set of legs are connected to the inner tube. During retrieval of the filter, a catheter 633 is inserted over one end of the filter 634, the first set of expandable legs, 635 in this illustration, are compressed inwards. The catheter 633 further moves down to plunge the handles 630 which then drive the second set of legs to close. The catheter 633 is pushed over to include both the first set and second set of expandable legs. For closing of the second set of legs, the filter may further comprise a third set of expandable legs having an expandable segment and having both ends secured to the filter.

Figure 25:
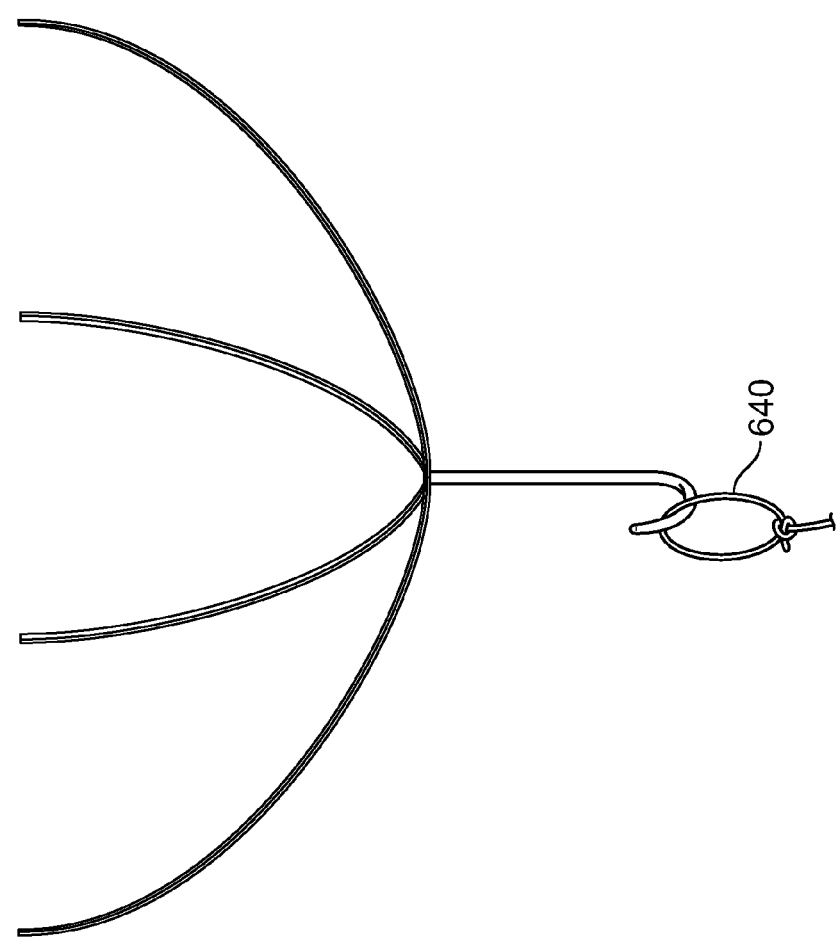
FIG. 25 shows a perspective view of one embodiment of the delivery device to deploy the filters of the present invention.

FIG. 25 shows one embodiment of the delivery device that can be used to deploy the filters of the present invention. The delivery device 640 can open and close like pliers. The delivery device may have at least one button on its handle to control the opening and/or closing. The delivery device holds the filter in place and allows re-sheathing until the final position for filter deployment is determined.

Figure 26A:
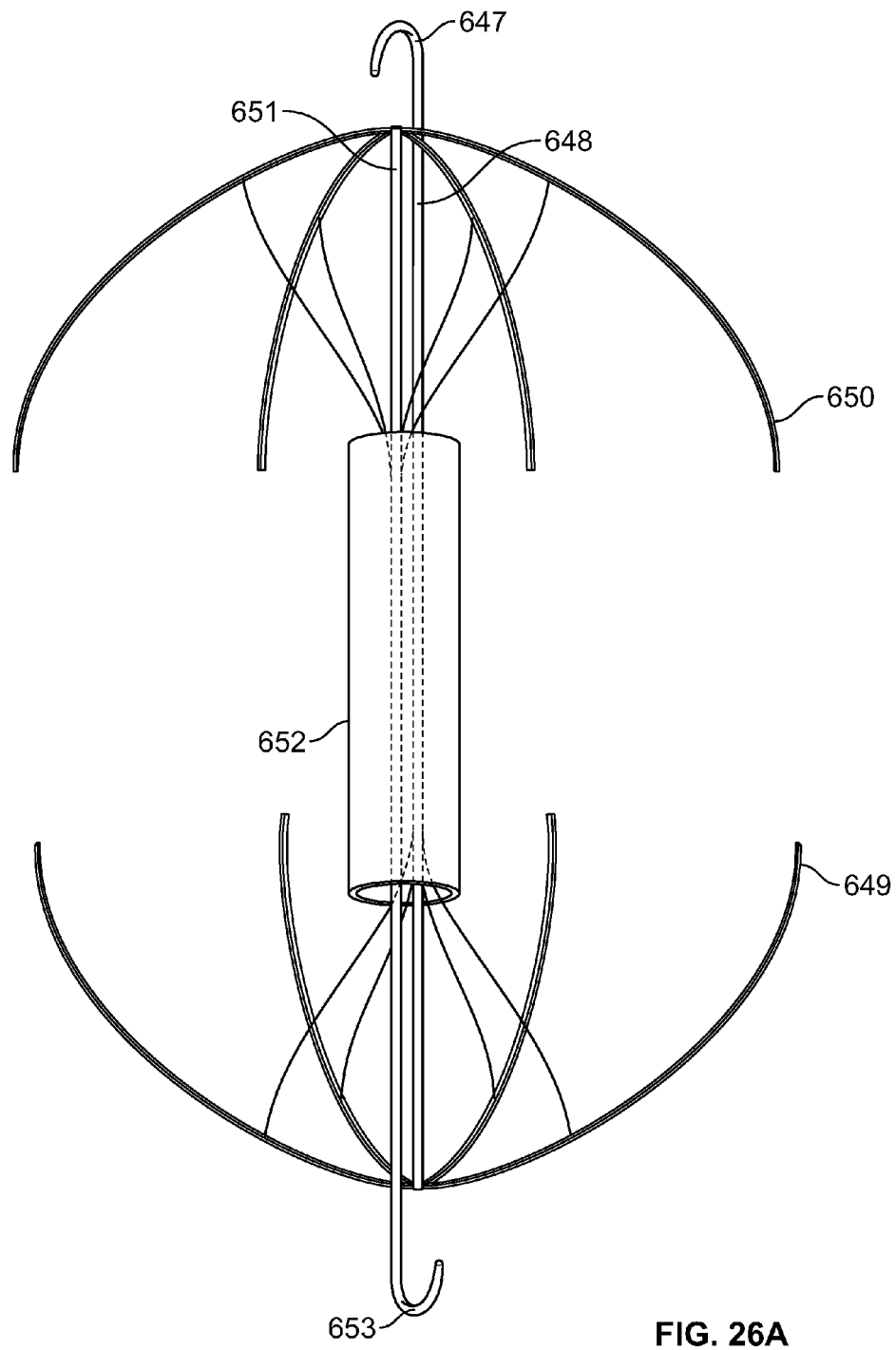
FIG. 26a shows a perspective view of one embodiment of the filter where the expandable legs are attached via connectors to a tube or pin. The end of the tube or pin has a hook or notch.
Figure 26B:
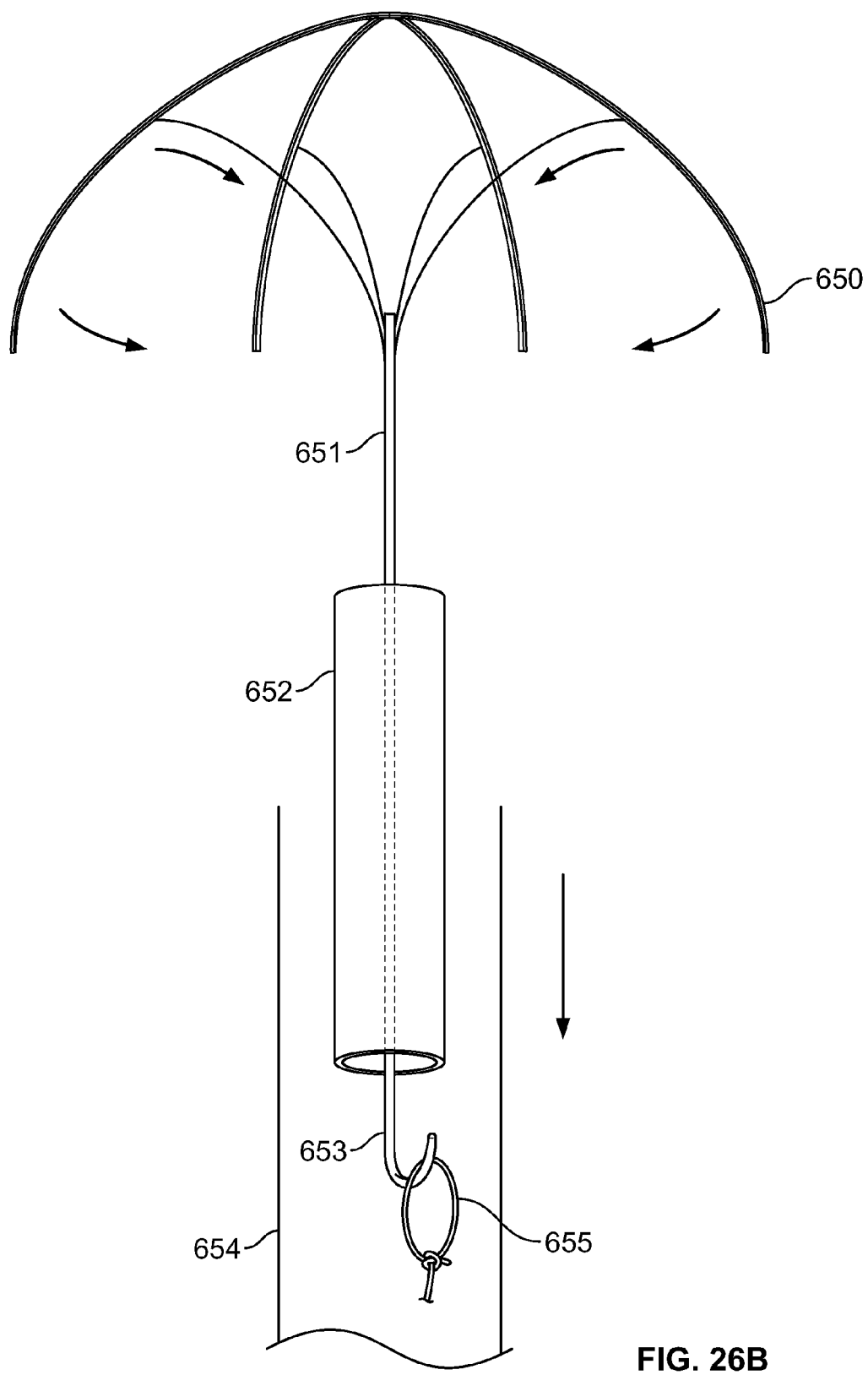

FIGS. 26a and 26b shows one embodiment of the filter. In this embodiment, the filter has a first set 650 and a second set 649 of expandable legs. The first set of expandable legs 650 are attached to a tube or pin 651 inserted into the first tube 652. The second set of expandable legs 649 are attached to a tube or pin 648 inserted into the first tube 652. The end of the tube or pin 651 is connected to a hook 653. The end of the tube or pin 648 is connected to a hook 647. During retrieval, a catheter 654 is inserted into a vessel and moved to where the filter is positioned on the vessel wall. A snare 655 is pushed through the catheter 654 until the snare grabs the hook 653. The physician exerts tension on the filter by pulling back on the snare 655 and pushing the catheter 654. The catheter 654 is pushed over the first tube 652 and the tube or pin 651. As the snare is pulled back, the expandable legs 650 are pulled to move inwards and retract from the wall of vena cava. The catheter 252, which encompasses the refracted filter, is then withdrawn from the vessel.

Figure 26C:
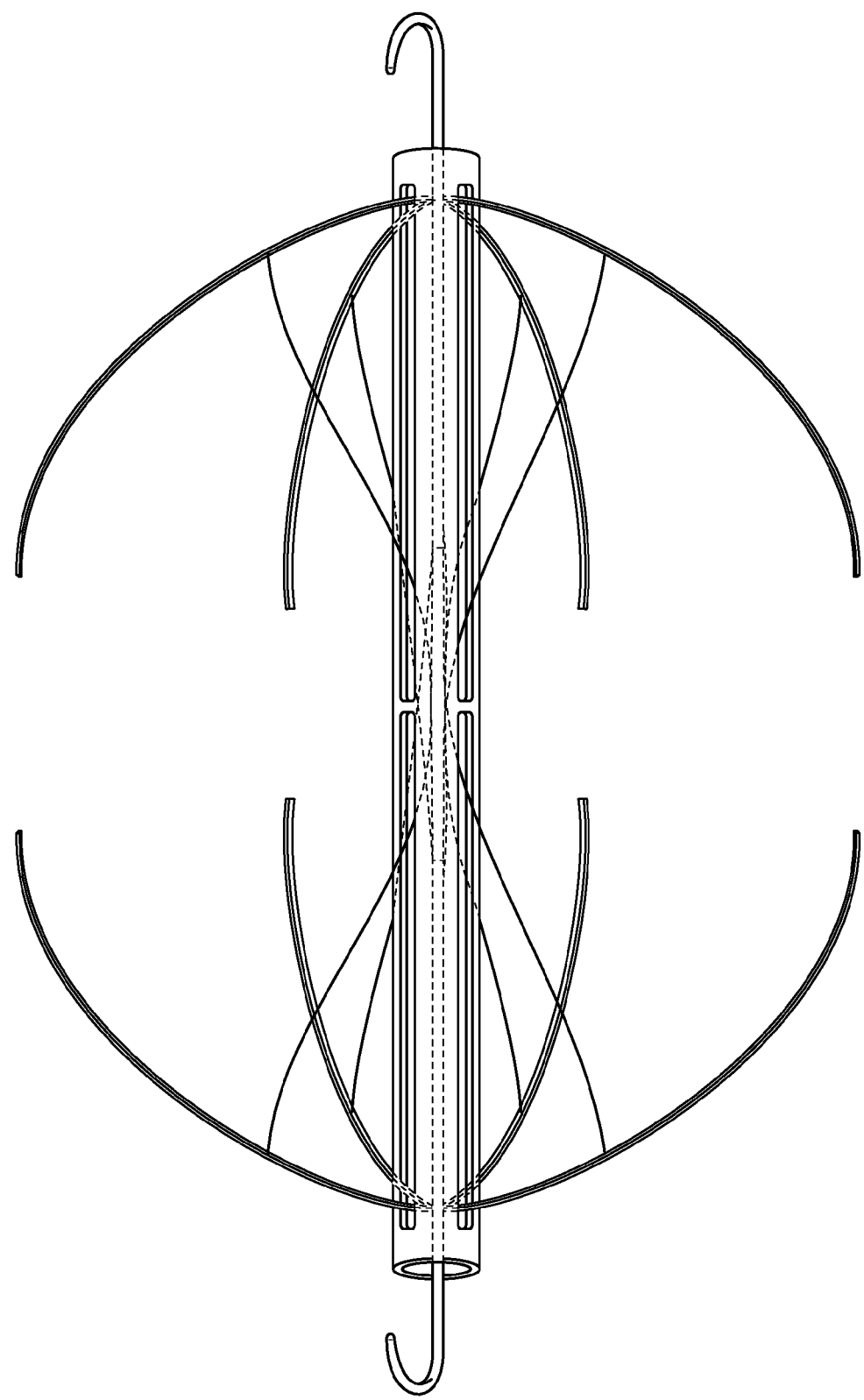
FIG. 26c shows a perspective view of another embodiment of the filter where the expandable legs are attached via connectors to a tube or pin. The end of the tube or pin has a hook or notch.

FIG. 26c shows another embodiment of the filter where the expandable legs are attached via connectors to a tube or pin. The end of the tube or pin is connected to a hook or notch.

Figure 27A:
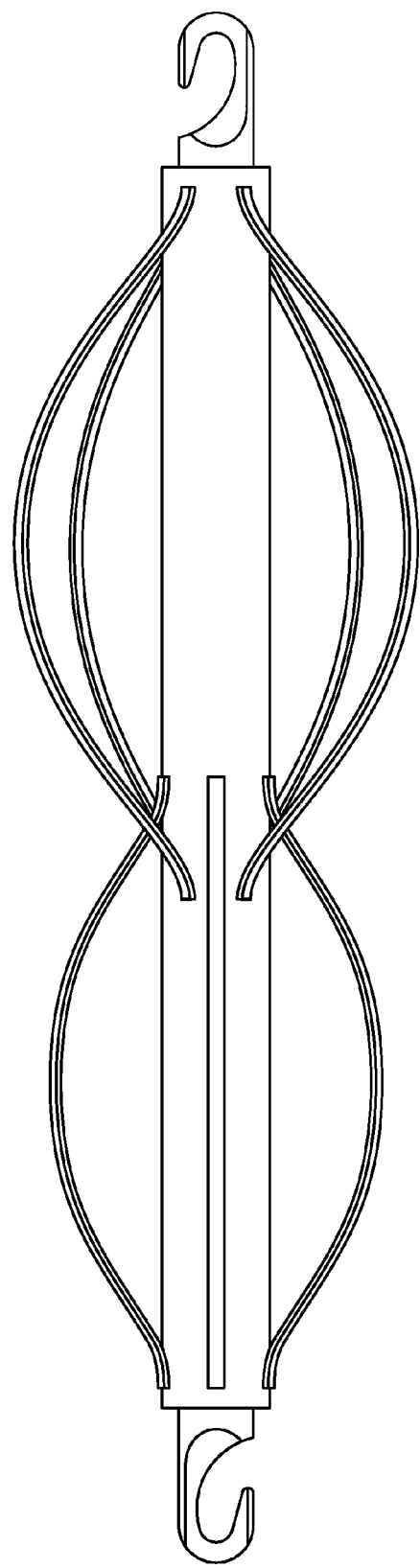
FIG. 27a shows a perspective view of one embodiment of the filter where the filter has two sets of expandable legs which can form overlapping cages.
Figure 27B:
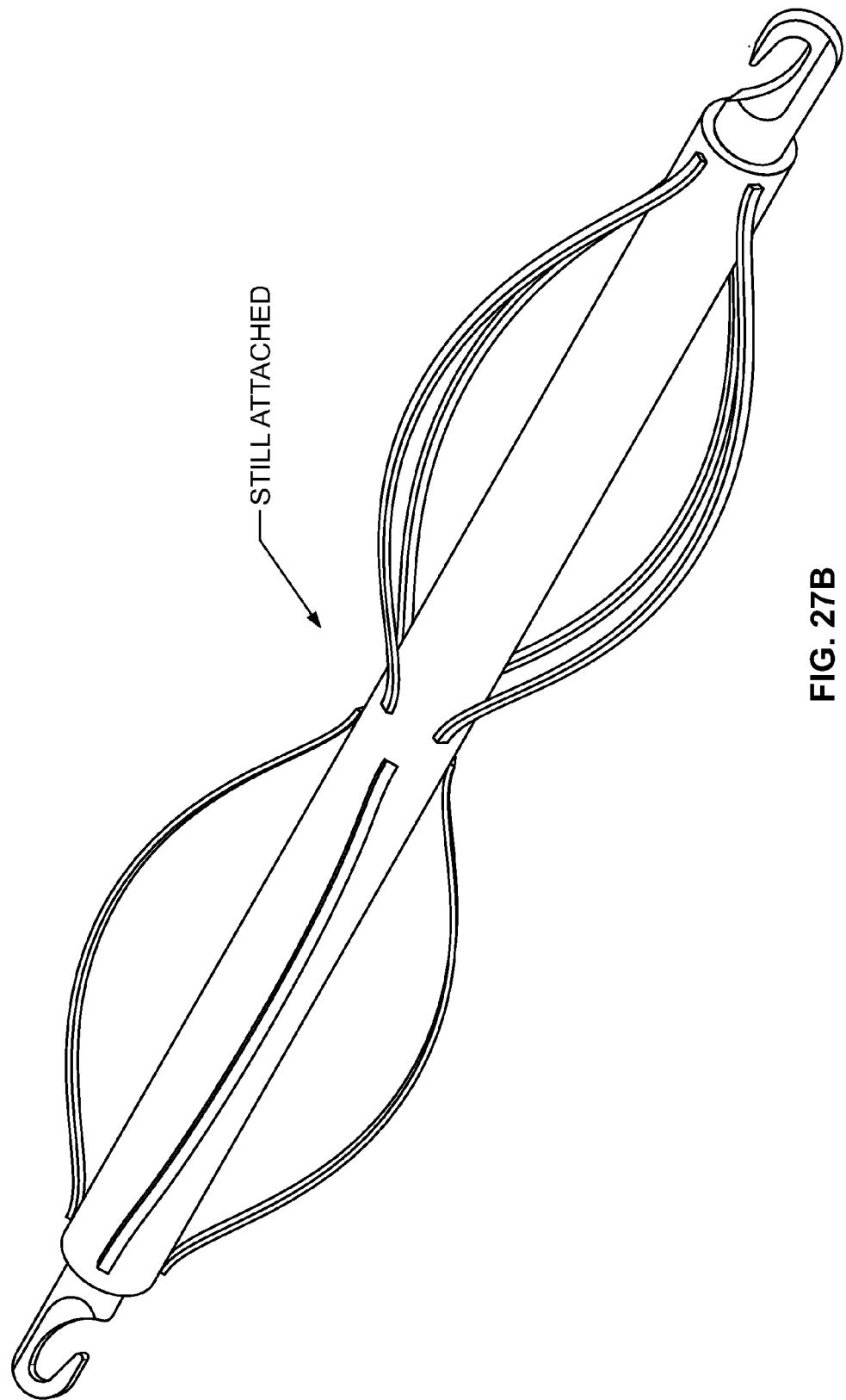

FIGS. 27a and 27b show one embodiment of the filter where the filter has two sets of expandable legs. Each leg of the two sets comprises an expandable segment and has both ends secured to the filter. Each set of the expandable legs can form a cage, a sphere or a basket shape. The two cages (spheres or baskets) may overlap or may be adjacent to each other.

Figure 28:
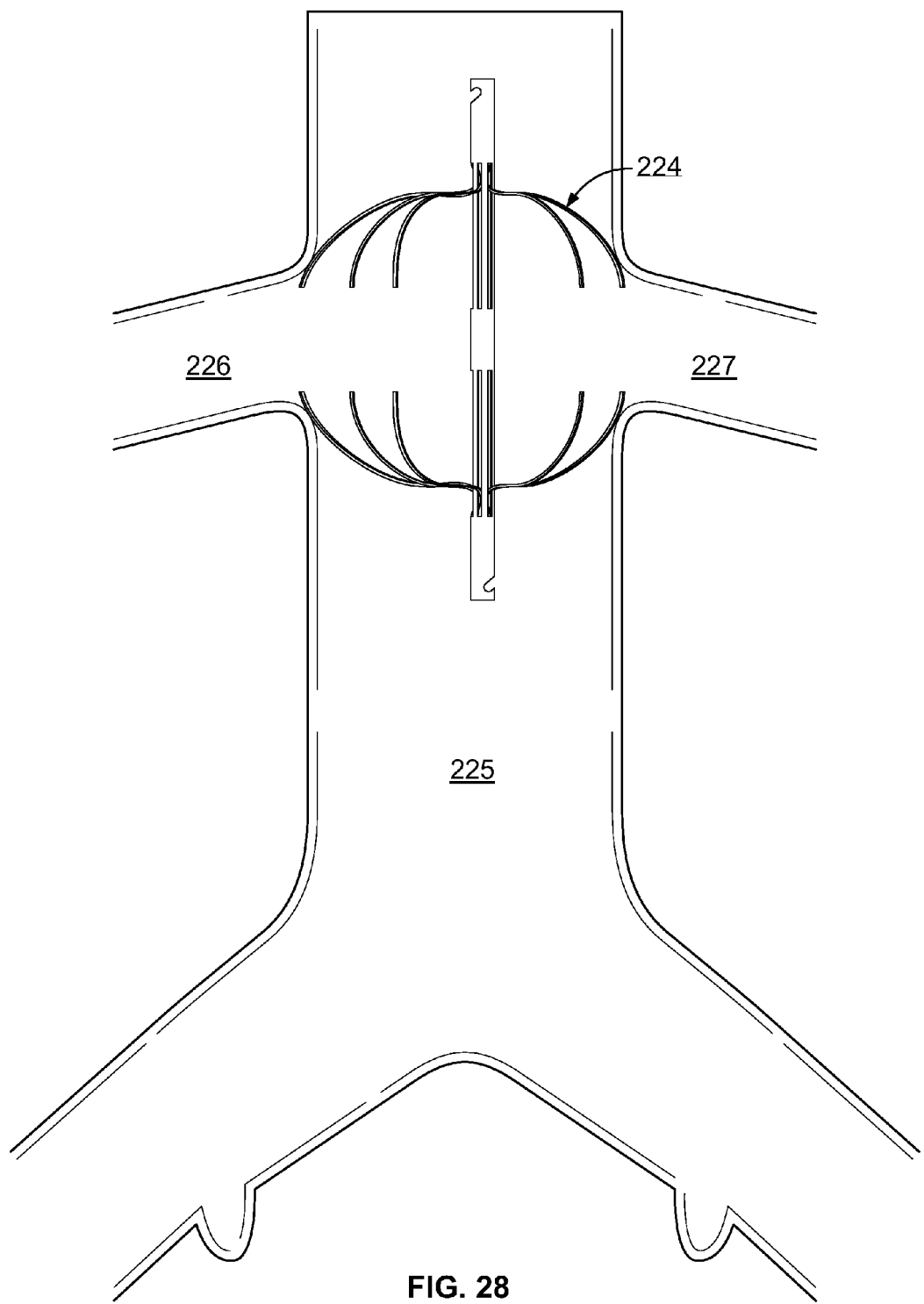
FIG. 28 shows deployment of the filter in FIG. 11a in the inferior vena cava.

The filter of the present invention may be deployed by any desired delivery system. FIG. 28 shows the filter 224 which is deployed in the inferior vena cava 225 at or below the junction of the right 226 and left 227 renal veins. The diameter of the axially collapsed filter may range from about 0.8 mm to about 5.5 mm, from about 1.2 mm to about 4.5 mm, or from about 1.5 mm to about 3 mm, with one specific embodiment of about 2 mm. The diameter of the delivery system, such as a delivery catheter, may range from about 0.8 mm to about 5.5 mm, from about 1.2 mm to about 4.5 mm, or from about 1.8 to about 3 mm. In one embodiment, the collapsed filter is encased in a delivery catheter of about 6 French (2 mm) in diameter. In another embodiment, the filter is delivered by a delivery catheter of about 8 French (2.67 mm) in diameter. The filter may be deployed by a simple push and pull delivery (see Cordis TrapEase Permanent Vena Cava Filter with the VisEase Angiographic Vessel Dilator [on-line]. Retrieved on Aug. 1, 2008, from URL: <http://www.mitek.com/home.jhtml?loc=USENG&page=viewContent&contentId=09008b9880ffdcbf&nodekey=/Prod_Info/Type/Endovascular_Disease_Management/Vena_Cava_Filters&parentId=fc0de00100001215>. The filter may be placed in a vessel such as the inferior vena cava using ultrasound at a patient's bedside or under standard fluoroscopy. A catheter containing the undeployed filter is inserted and the filter extruded from the catheter. The filter then floats into place at or below the junction of the left and right renal vein. After insertion and deployment, the filter assumes a position within the inferior vena cava at or near the junction of the left and right renal veins 226, 227 (FIG. 28). The first and second sets of expandable legs form two hemispheres respectively in the vessel creating a cage or sphere. The barbs of the filter open and insert into the vessel wall when the width of the vessel wall exceeds the diameter of the filter. The barbs are on the ends of the legs which are on the outer curvature of the spheres. The sphere shape prevents barb deployment until the diameter of the blood vessel exceeds the deployment diameter for the barbs. The deployment diameter for the barbs may range from about 7 mm to about 20 mm, from about 10 mm to about 18 mm or about 15 mm.

Figure 29:
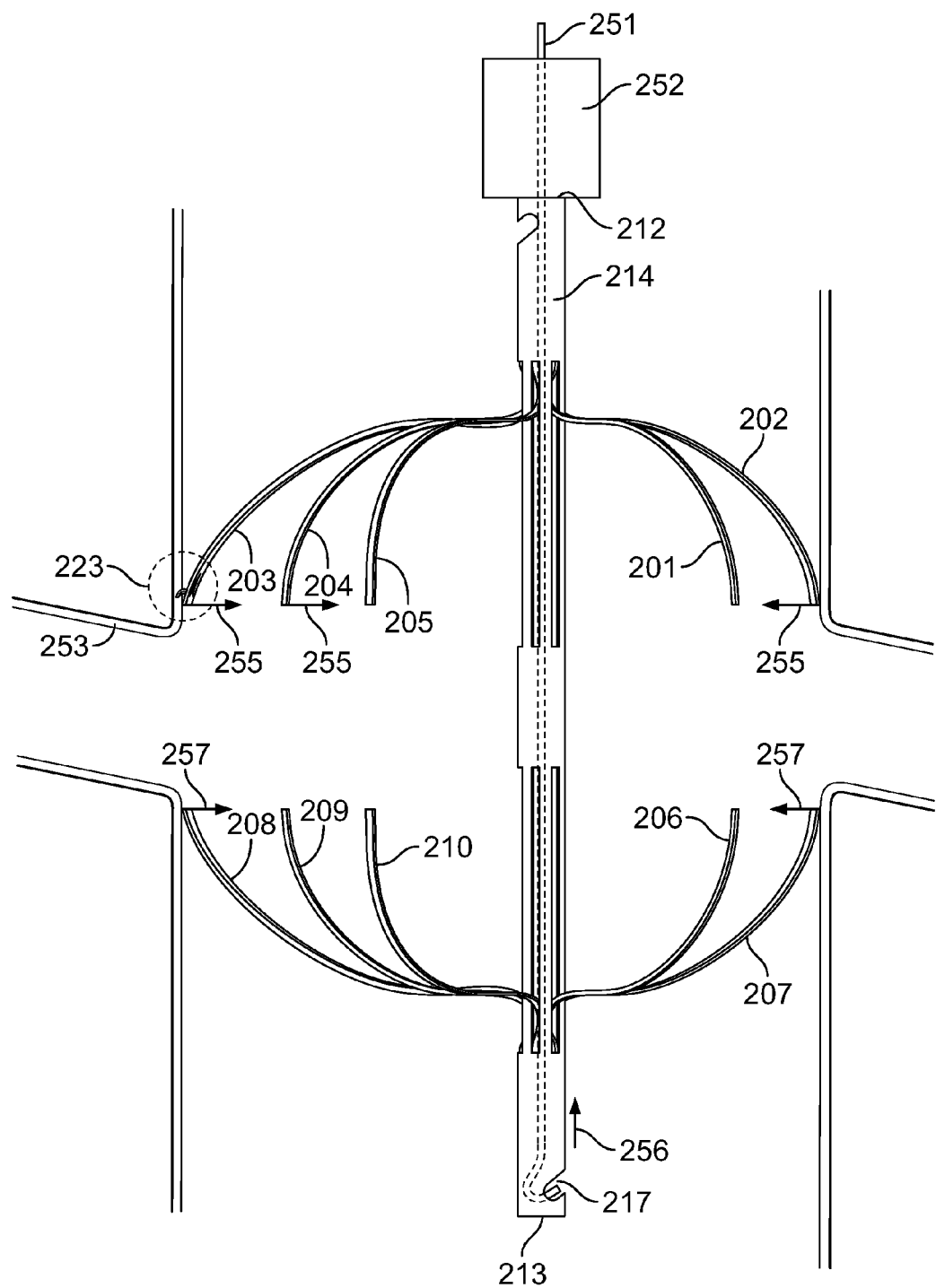
Figure 31:
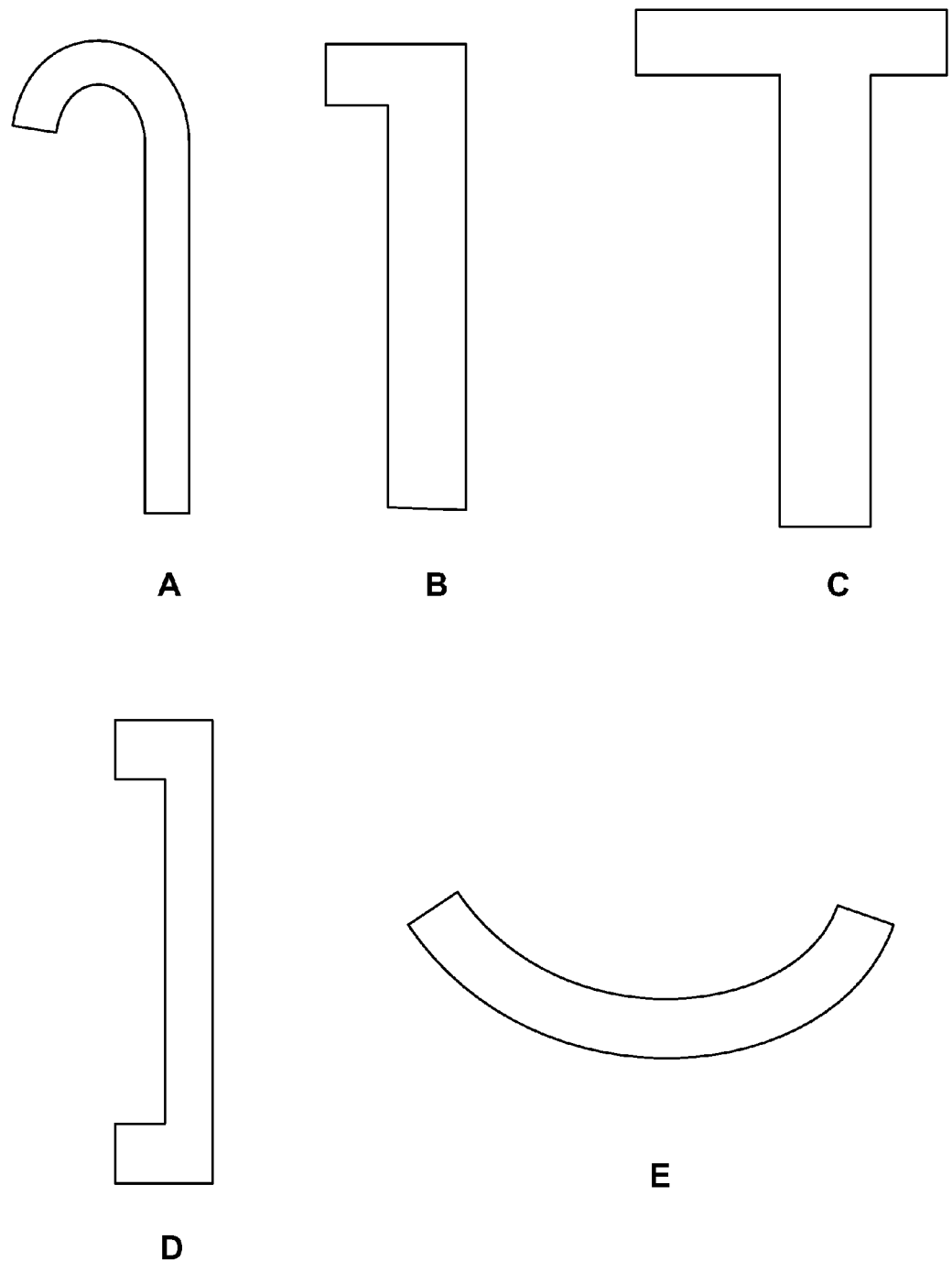
FIG. 31 shows the configuration of various forms of the notch.

The invention provides for a method for retrieving the vena cava filter. FIG. 29 illustrates retrieval of the filter shown in FIG. 11. A catheter 252, the internal dimension of which is greater than the external dimension of the first tube 214, is inserted into a vessel such as the jugular vein and moved to where the filter is positioned on the vessel wall. A snare 251 is pushed through the catheter 252 and the inner space of the second tube until the snare grabs the notch 217 closest to the end 213. The notch 217 is shown in this embodiment as a semicircular structure. The notch may have a variety of different structures such as a rectangular hole or a square hole as long as it permits efficient hooking of the filter by a snare 251. The notch 217 may be positioned from about 2 mm to about 10 mm from the end 225, from about 4 mm to about 8 mm, from about 6 mm to about 8 mm and about 5 mm. The physician exerts tension on the filter by pulling back on the snare 251 and pushing the catheter 252. The tension exerted may be in the range of about 0.45 kilogram (kg) to about 5 kg, but the appropriate amount of tension may be determined by one of ordinary skill in the art based on clinical experience in the art. Various embodiments of the notch 217 are shown in FIG. 31 ((a)-(e)). The notch 217 may assume many different shapes such as a hook (a), a L shape (b), a T-shape (c), a reverse C-shape (d) and a semi-circular shape (e) as long as it permits secure capture by the snare 251. The snare may also take many different forms, such as a loop or a wire basket. The snare may be formed from several interconnected pieces of material or from a single piece of material. In addition, the snare may comprise a locking mechanism that locks once the snare grabs the notch on the filter. The catheter 252 is pushed over each leg of the first set of expandable legs 201, 202, 203, 204, 205, until each expandable leg retracts from the wall 253 of vena cava. As each leg of the first set is bent inward at its end, the legs easily move inwards when the catheter 252 is pushed over each leg of the first set. The barbs 223 dislodge from the vessel wall and move inwards 255. As the snare 251 is pulled back, the first tube is pulled towards 256 the catheter exerting tension on the second set of expandable legs 206, 207, 208, 209, 210, causing the second set of expandable legs 206, 207, 208, 209, 210, to move inwards 257, and retract from the vessel wall 253. The catheter 252, which encompasses the refracted filter, is then withdrawn from the vessel.

The filter may be retrieved from the other end 213 of the filter (FIG. 29). The method of retrieving the filter from the other end 213 is similar as set forth except that a snare 251 is pushed through the catheter 252 and the second tube until the snare grabs the notch 217 closest to the end 212. The catheter is pushed over the second set 206, 207, 208, 209, 210 of expandable legs. The second set of expandable legs 206, 207, 208, 209, 210 retract from the vessel wall. The snare pulls back the first tube pushing the first set of expandable legs 201, 202, 203, 204, 205, and the first set of expandable legs 201, 202, 203, 204, 205 retract from the vessel wall. The filter shown in FIG. 14 may be retrieved using a similar mechanism as shown in FIG. 29.

Figure 30:
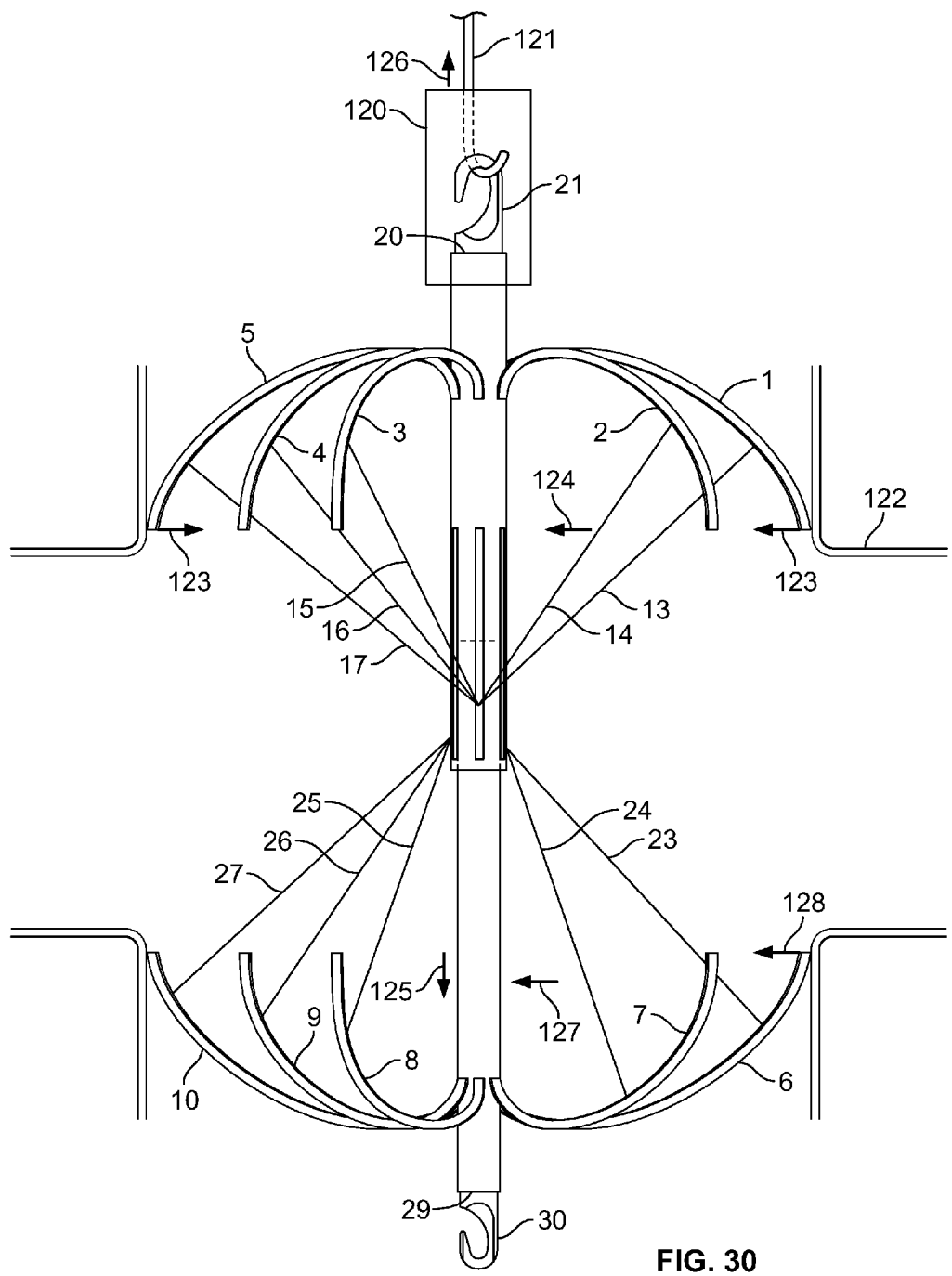

FIG. 30 illustrates retrieval of the filter shown in FIG. 1. A catheter 120, the internal dimension of which is greater than the external dimension of the first tube 19, is inserted into a vessel such as the jugular vein and moved to where the filter is positioned on the vessel wall. A snare 121 is pushed through the catheter 120 until the snare grabs the notch 21 closest to the end 20. The notch 21 is shown in this embodiment as a hook structure. The notch may have a variety of different structures such as a rectangular hole or a square hole as long as it permits efficient hooking of the filter by a snare 121. The notch 21 may be positioned from about 2 mm to about 10 mm from the end 25, from about 4 mm to about 8 mm, from about 6 mm to about 8 mm and about 5 mm. The physician exerts tension on the filter by pulling back 126 on the snare 121 and pushing the catheter 120. The tension exerted may be in the range of about 0.45 kilogram (kg) to about 5 kg, but the appropriate amount of tension may be determined by one of ordinary skill in the art based on clinical experience in the art. Various embodiments of the notch 21 are shown in FIG. 31 ((a)-(e)). The notch 21 may assume many different shapes such as a hook (a), a L shape (b), a T-shape (c), a reverse C-shape (d) and a semi-circular shape (e) as long as it permits secure capture by the snare 121. The snare may also take many different forms, such as a loop or a wire basket. The snare may be formed from several interconnected pieces of material or from a single piece of material. In addition, the snare may comprise a locking mechanism that locks once the snare grabs the notch on the filter. The catheter 120 is pushed over each leg of the first set of expandable legs 1, 2, 3, 4, 5, until each expandable leg retracts from the wall 122 of vena cava. As each leg of the first set is bent inward at its end, the legs easily move inwards when the catheter 120 is pushed over each leg of the first set. The barbs 32 dislodge from the vessel wall and move inwards 123. As the first set of expandable legs move inwards, the first set of connectors are pushed to move inwards 124 pushing the second tube to move downwards 125 away from the snare. In the mean time, while the physician pulls back 126 on the snare, the first tube moves upwards, causing the second set of connectors to move inwards 127 and the second set of legs to move inwards 128, and retract from the vessel wall 122. The catheter 120, which encompasses the retracted filter, is then withdrawn from the vessel.

The filter may be retrieved from the other end 29 of the filter (FIG. 30). The method of retrieving the filter from the other end 29 is similar as set forth except that a snare 121 is pushed through the catheter 120 and the second tube until the snare grabs the notch 30 closest to the end 29. The catheter is pushed over the second set 6, 7, 8, 9, 10 of expandable legs. The second set of expandable legs 6, 7, 8, 9, 10 retract from the vessel wall. Closing of the second set of legs causes the second set of connectors to move inward and the first tube to move away from the snare. Meanwhile, the snare pulls back the second tube pulling the first set of connectors to move inward, dragging the first set of legs 1, 2, 3, 4, 5 to retract from the vessel wall. The filter shown in FIG. 4 may be retrieved using a similar mechanism as shown in FIG. 30.

Figure 32:
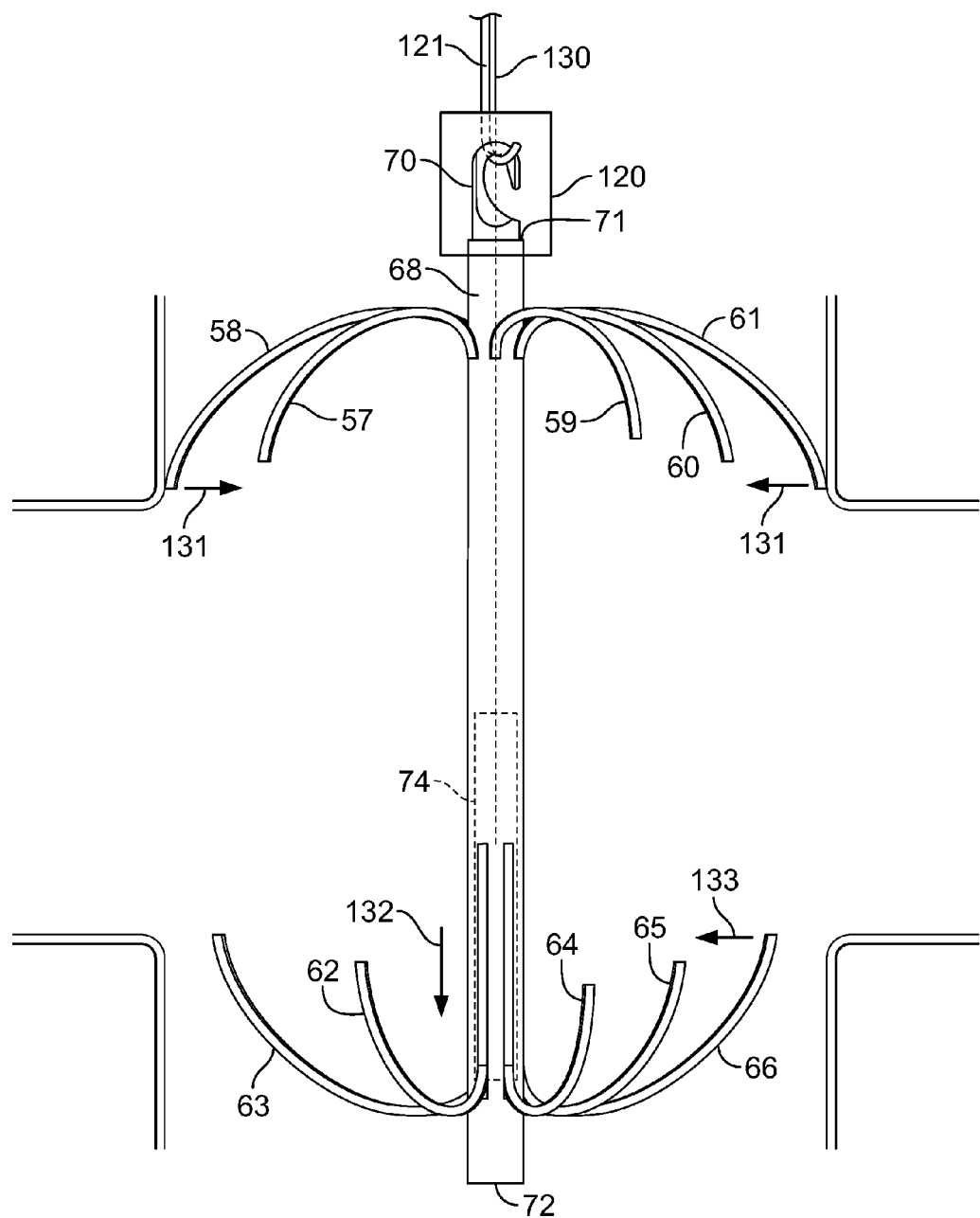

The filter shown in FIG. 6 can be retrieved by a method shown in FIG. 32. A catheter 120 is inserted to the vessel. A snare 121 is pushed through the catheter until the snare grabs the notch 70 at the end 71 on the first tube 68. A wire 130 is pushed through the catheter and the inner space of the first tube 68 until the wire reaches the second tube or pin 74. The catheter 120 is then pushed over each expandable leg of the first set 57, 58, 59, 60, 61 until each expandable leg of the first set moves inwards 131 and retracts from the vessel wall 122. In the mean time, the wire 130 is pushed to force the second tube or pin 74 to move downwards 132 toward end 72 to exert tension on the second set of expandable legs 62, 63, 64, 65, 66 until the second set of expendable legs move inwards 133 and retract from vessel wall 122, The catheter 120, which encompasses the refracted filter, is then withdrawn from the vessel.

Figure 33:
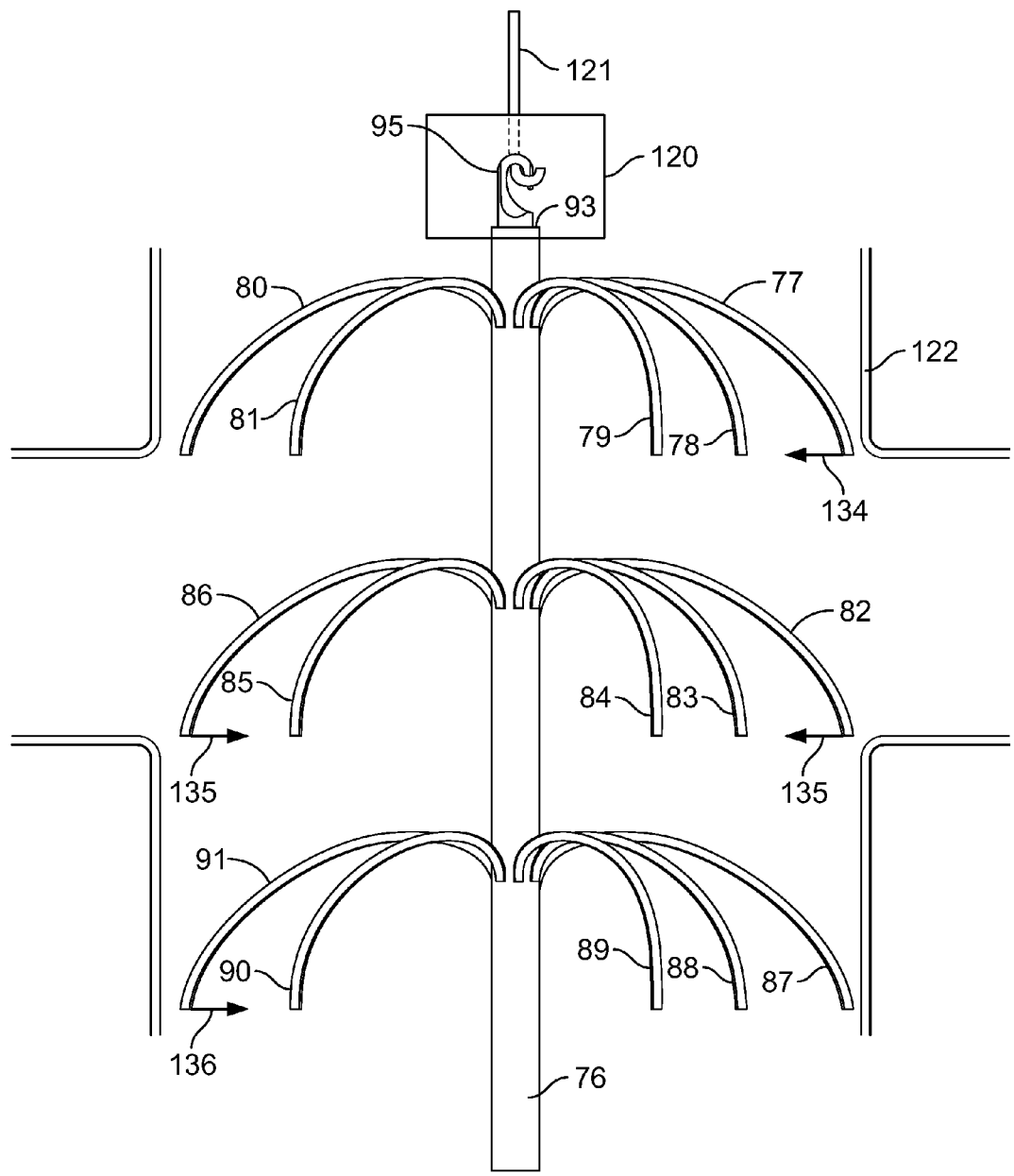

The filter shown in FIG. 8 can be retrieved by a method shown in FIG. 33. A catheter 120 is inserted into a vessel, a snare 121 is pushed through the catheter until the snare grabs the notch 95 on the tube 76 closest to the end 93. The snare 121 is pulled back, while the catheter 120 is pushed over each expandable leg of the first set 77, 78, 79, 80, 81 until each expandable leg retracts 134 from the vessel wall. The catheter 120 is pushed further to exert tension on the second set of expandable legs 82, 83, 84, 85, 86 until the second set of legs retract 135 from the vessel wall and closed. The catheter is pushed over the third expandable legs 87, 88, 89, 91 until the third set of legs retract 136 from the vessel wall. The catheter 120, which encompasses the retracted filter, is then withdrawn from the vessel.

Figure 34:
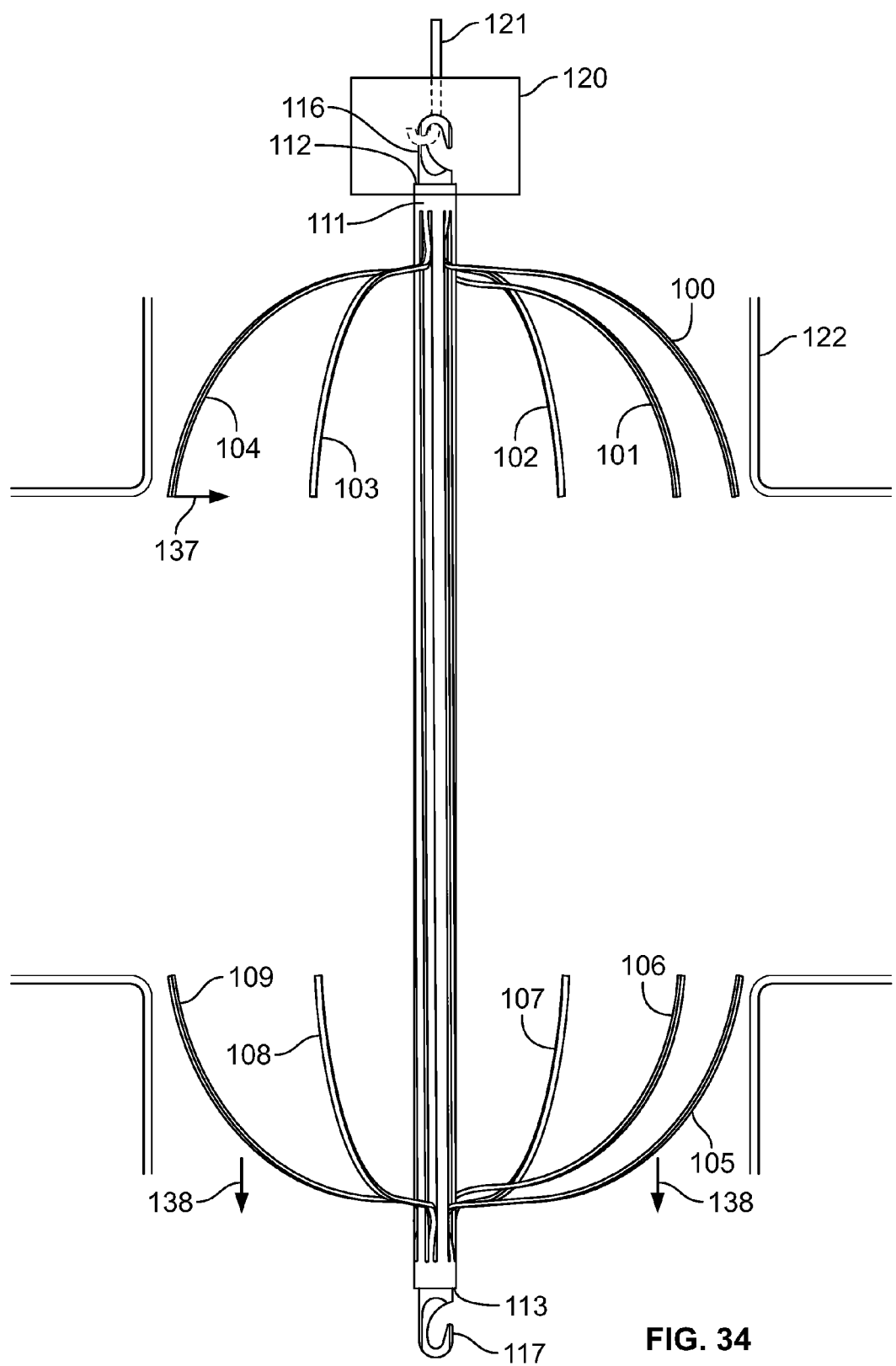

The filter shown in FIG. 9 can be retrieved by a method shown in FIG. 34. A catheter 120 is inserted into a vessel. A snare 121 is pushed through the catheter 120 until the snare grabs the notch 116 closest to the end 112 on the tube 111. The catheter 120 is pushed over each leg of the first set of expandable legs 101, 102, 103, 104, 105, until each expandable leg refracts from the wall 122 of vena cava. As each leg of the first set is bent inward at its end, the legs easily move inwards 137 when the catheter 120 is pushed over each leg of the first set. After the first set of legs closed, the catheter is further pushed down over each leg of the second set of expandable legs 105, 106, 107, 108, 109. Because each leg of the second set is bent inward at its end, the legs easily invert 138 as the catheter pushes over it. The catheter 120, which encompasses the refracted filter, is then withdrawn from the vessel.

The filter in FIG. 9 may also be retrieved from the other end 113 of the filter. The method of retrieving the filter from the other end 113 is similar as set forth except that a snare 121 is pushed through the catheter 120 until the snare grabs the notch 117 closest to the end 113. The catheter is pushed over the second set 105, 106, 107, 108, 109 of expandable legs. The second set of expandable legs 105, 106, 107, 108, 109 retract from the vessel wall. The catheter is further pushed over the first set of expandable legs until the first set of legs invert. The catheter 120, which encompasses the retracted filter, is then withdrawn from the vessel.

Figure 35:
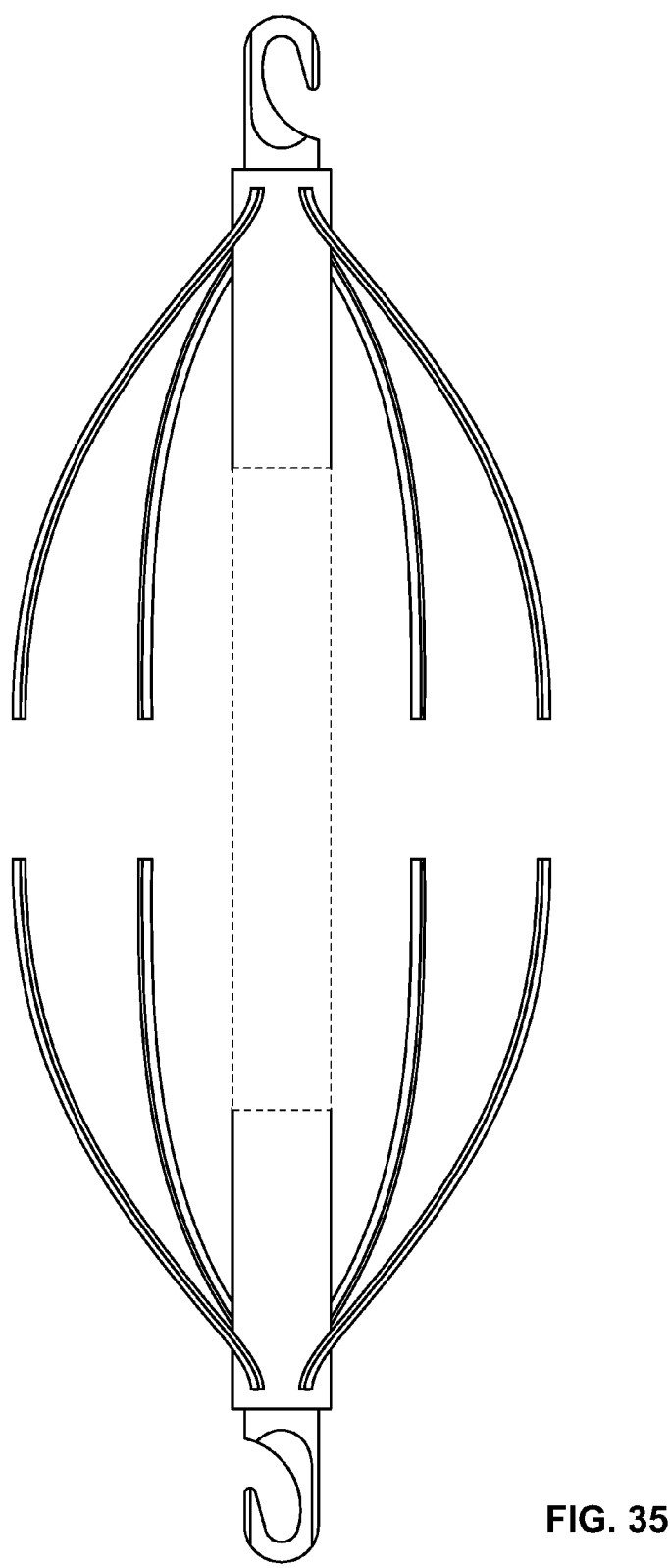
FIG. 35 shows an embodiment of the filter where the tube can elongate during retrieval.

FIG. 35 shows an embodiment of the filter where the tube can elongate during retrieval. The filter has a hook on both ends. The hook is tilted backwards so as to pull into catheter with snare during retrieval. During retrieval of the filter, the tube elongates when snared and pulled. As it elongates, it pulls legs inward.

The filter may be made of laser cut, self-expanding nitinol. The filter may also be made of any metal, such as titanium, platinum, gold, a metal alloy, such as stainless steel, or a memory metal. In one embodiment, each of the expandable legs of the first and second sets comprise memory metal. In another embodiment, the expandable segment of the expandable legs of the third and the fourth set comprises memory metal. The filter may further be made of any biocompatible material that is durable and non-corrosive. Examples of biocompatible material include a synthetic material such as polyurethanes, segmented polyurethane-urea/heparin, poly-L-lactic acid, cellulose ester, polyethylene glycol, polyvinyl acetate, dextran and gelatin, a naturally-occurring material such as basement membrane components such as collagen, elastin, laminin, fibronectin, vitronectin; fibrin, cellulose, and amorphous carbon, or fullerenes. In some embodiments of the invention, the filter is made of biodegradable, bioabsorbable, bioerodable material and/or a mixture thereof. Examples of bioabsorbable material include copolymers of glycolide with lactide or ϵ-caprolactone, and poly(p-dixanone). The filter may be made of a single material or different materials. U.S. Patent Publication No. 20070191932. U.S. Pat. No. 7,147,649.

The filter of the present invention may be manufactured in numerous ways. The filter may be formed from a single piece of material by removing various portions of a tube or pipe's wall to form the configurations described herein. The filter may also be manufactured by connecting various segments together. Material from the tube wall may be removed using various techniques including laser (e.g. YAG laser), electrical discharge machining, mechanical machining, chemical etching (e.g. photo-fabrication), metal cutting, a combination thereof, or other well known techniques. See U.S. Pat. Nos. 7,329,277, 5,879,381, and 6,117,165.

While the vena cava filters are preferred embodiments of the present invention, filters within the scope of the invention may be placed in any desired blood vessel or endovascular structure. The filter may be placed via a femoral access point, jugular access point or any desired intravascular route. The filter may be placed in the body of the patient permanently or temporarily before being retrieved.

After the vena cava filter is deployed, the vascular endothelial cells or other tissues grow where the filter and vessel wall contact. When the filter is retrieved later, severe damage may occur resulting in laceration or rupture of the vena cava, or at the very least, a focal disruption of the endothelial lining which may predispose to caval stenosis, thrombosis or occlusion. To reduce the risk of complications, the free ends of the legs, other parts of the filter, or the entire filter can be coated with an antiproliferative agent to prohibit the tissue ingrowth, an anti-inflammatory agent or any desired pharmaceutically active agents. Examples of anti-proliferative agents include paclitaxel (taxol), paclitaxel derivatives, rapamycin (sirolimus), rapamycin derivatives (including everolimus, zotarolimus, biolimus and biolimus A-9), 5-fluorouracil, cisplatin, vinblastine, vincristine, epothilones, endostatin, angiostatin and thymidine kinase inhibitors or a combination thereof. Examples of the anti-inflammatory agent include dexamethasone, corticosterone and prednisolone. Examples of pharmaceutically active agents that prevent or reduce thrombus formation include anticoagulants, antiplatelets and fibrinolytics. The pharmaceutically active agents include therapeutic agents and/or diagnostic agents. The therapeutic agents may comprise drugs that are used in the treatment of vascular disease, including artherosclerosis, restenosis, thrombosis. The pharmaceutically active agent may be antibiotics/antimicrobials, antiproliferatives, antineoplastics, antioxidants, endothelial cell growth factors, thrombin inhibitors, immunosuppressants, anti-platelet aggregation agents, collagen synthesis inhibitors, therapeutic antibodies, nitric oxide donors, antisense oligonucleotides, wound healing agents, therapeutic gene transfer constructs, peptides, proteins, extracellular matrix components, vasodialators, thrombolytics, anti-metabolites, growth factor agonists, antimitotics, stating, steroids, steroidal and non-steroidal anti-inflammatory agents, angiotensin converting enzyme (ACE) inhibitors, free radical scavengers, PPAR-gamma agonists and anti-cancer chemotherapeutic agents. Examples of the pharmaceutically active agents in the present invention also include rosuvastatin, cyclosporin A (CSA), mycophenolic acid (MPA), retinoic acid, n-butyric acid, butyric acid derivatives, vitamin E, probucol, L-arginine-L-glutamate, tacrolimus (FK-506), puerarin, platelet factor 4, basic fibroblast growth factor (bFGF), fibronectin, simvastatin, fluvastatin, ABT-578, interferon, dexamethasone, dihydroepiandrosterone (DHEA) and estradiol.

Any part of the filter or the entire filter can be coated with any desired pharmaceutically active agents. An excipient may be coated on the filter together with the pharmaceutically active agent. The examples of the excipient include binder, matrix, carrier, polymer, hydrogel and nanoparticle. The coating on the filter may be smooth, semi-porous or porous. The coating may be one layer or multiple layers. A pharmaceutically active agent or excipient may also be deposited in a defined structure of the filter, such as tubes, grooves, wells, bells, baskets, etc. A pharmaceutically active agent may also be incorporated into a biocompatible polymer matrix. Polymer matrices include polymers such as poly(lactide-co-glycolide); poly-DL-lactide, poly-L-lactide, and/or mixtures thereof and can be of various inherent viscosities and molecular weights. In one embodiment, poly(DL lactide-co-glycolide) (DLPLG, Birmingham Polymers Inc.) can be used. U.S. Patent Publication No. 20070141107. The pharmaceutically active agent may be released in a sustained, delayed, spiked, controlled or any desired manner.

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

What is claimed is:

1. A filter comprising,
   a proximal end member comprising a first cylindrical portion;
   a first notch extending inwardly from a wall of the first cylindrical portion;
   a distal end member comprising a second cylindrical portion;
   a second notch extending inwardly from a wall of the second cylindrical portion;
   a first plurality of expandable legs, wherein each leg of the first plurality of expandable legs extends from a proximal end coupled to the proximal end member to an apex of a first plurality of apices such that the first plurality of legs forms a first generally conical shape between the proximal end member and the first plurality of apices;
   a second plurality of expandable legs, wherein each leg of the second plurality of expandable legs extends from a distal end coupled to the distal end member to an apex of a second plurality of apices such that the second plurality of legs forms a second generally conical shape between the distal end and the second plurality of apices;
   a plurality of connectors, each connector coupled to, and extending between, an apex of the first plurality of apices and an apex of the second plurality of apices, wherein the apices of the first plurality of apices and the apices of the second plurality of apices all have substantially the same radial displacement from a longitudinal axis of the filter;

a first barb extending from a first leg of the first plurality of legs from a position proximal to a first apex of the first plurality of apices; and a second barb extending from a second leg of the second plurality of legs from a position distal to a second apex of the second plurality of apices;

wherein a connector of the plurality of connectors is coupled to the first leg and the second leg and wherein the first barb is disposed on an opposite lateral side of the connector from the second barb.

2. The filter of claim 1, wherein the filter is encased in a catheter in an undeployed state.

3. The filter of claim 1, wherein each connector extends a distance along the longitudinal axis of the filter creating a longitudinal offset between the first plurality of apices and the second plurality of apices.

4. The filter of claim 1, wherein a portion of the first barb and a portion of the second barb extend longitudinally toward each other.

5. The filter of claim 1, wherein the number of expandable legs in the first plurality is five, and the number of legs in the second plurality is five.

6. The filter of claim 1, wherein the first barb extends from a position radially inward from the first apex and wherein the second barb extends from a position radially inward from the second apex.

7. The filter of claim 6, wherein a free end of the first barb extends to a position radially outward from the first apex and wherein a free end of the second barb extends to a position radially outward from the second apex.

8. A filter comprising:

a proximal end member, a distal end member, and a longitudinal axis between the proximal and distal end members;

a first set of expandable legs, each leg of the first set of legs having a proximal end coupled to the proximal end member of the filter;

a second set of expandable legs, each leg of the second set of legs having a distal end coupled to the distal end member of the filter;

the filter configured such that the legs of the first set extend toward the second set of legs and the legs of the second set extend toward the first set of legs, and each leg of the first set of legs continuously extends radially and longitudinally from the proximal end of the filter to a first set of apices such that the first set of legs forms a first generally conical shape and each leg of the second set of legs continuously extends radially and longitudinally from the distal end of the filter to a second set of apices such that the second set of legs forms a second generally conical shape and wherein the apices of the first set of apices and the apices of the second set of apices all have substantially the same radial displacement from the longitudinal axis of the filter, and a plurality of connectors, each connector disposed between, and coupled to, one leg of the first set of legs and one leg of the second set of legs wherein each connector extends a distance along the longitudinal axis of the filter creating a longitudinal offset between the first set of apices and the second set of apices, and a first barb coupled to a first leg of the first set of legs at a position proximal to a first apex of the first set of apices and a second barb coupled to a second leg of the second set of legs at a position distal to a second apex of the second set of apices wherein a first connector of the plurality of connectors is coupled to the first leg and the second leg and wherein the first barb and the second barb are disposed on opposite lateral sides of the first connector, and wherein the filter is integrally formed.

9. The filter of claim 8, wherein the connectors are coupled to distal ends of the first set of legs and to proximal ends of the second set of legs.

10. The filter of claim 8, wherein the filter is integrally formed from a single tube of material.

11. The filter of claim 8, wherein the legs of the second set of legs are circumferentially offset from the legs of the first set of legs.

12. The filter of claim 8, wherein the proximal end member comprises a cylindrical portion and the filter further comprises a notch extending radially inward from a wall of the cylindrical portion.

13. The filter of claim 8, wherein a cage is formed comprising expandable legs from the first and second sets of legs.

14. The filter of claim 8, wherein the number of expandable legs in the first set is five, and the number of legs in the second set is five.

15. The filter of claim 8, wherein the first barb and the second barb extend longitudinally toward each other.

16. The filter of claim 8, wherein a free end of the first barb extends to a position distal of the first apex and wherein a free end of the second barb extends to a position proximal of the second apex.

* * * * *